(12) United States Patent
Tsunoda et al.

(10) Patent No.: US 11,547,723 B2
(45) Date of Patent: Jan. 10, 2023

(54) KOC1-DERIVED PEPTIDE AND VACCINE INCLUDING SAME

(71) Applicant: ONCOTHERAPY SCIENCE, INC., Kawasaki (JP)

(72) Inventors: Takuya Tsunoda, Kawasaki (JP); Ryuji Osawa, Kawasaki (JP); Sachiko Yamashita, Kawasaki (JP); Tomohisa Watanabe, Kawasaki (JP); Tetsuro Hikichi, Kawasaki (JP)

(73) Assignee: ONCOTHERAPY SCIENCE, INC., Kawasaki (JP)

( * ) Notice: Subject to any disclaimer, the term of this patent is extended or adjusted under 35 U.S.C. 154(b) by 334 days.

(21) Appl. No.: 16/773,487

(22) Filed: Jan. 27, 2020

(65) Prior Publication Data
US 2020/0155596 A1 May 21, 2020

Related U.S. Application Data

(62) Division of application No. 15/501,125, filed as application No. PCT/JP2015/071829 on Jul. 31, 2015, now Pat. No. 10,576,102.

(30) Foreign Application Priority Data

| Aug. 4, 2014 | (JP) | 2014-158919 |
| Aug. 4, 2014 | (JP) | 2014-158920 |
| Aug. 4, 2014 | (JP) | 2014-158921 |

(51) Int. Cl.

| A61K 38/00 | (2006.01) |
| A61K 35/14 | (2015.01) |
| A61K 39/00 | (2006.01) |
| A61K 48/00 | (2006.01) |
| C07K 16/18 | (2006.01) |
| C07K 7/06 | (2006.01) |
| C07K 7/08 | (2006.01) |
| C12N 5/10 | (2006.01) |
| C12N 15/09 | (2006.01) |
| A61K 35/12 | (2015.01) |

(52) U.S. Cl.
CPC .............. *A61K 35/14* (2013.01); *A61K 35/12* (2013.01); *A61K 39/00* (2013.01); *A61K 48/00* (2013.01); *C07K 7/06* (2013.01); *C07K 7/08* (2013.01); *C07K 16/18* (2013.01); *C12N 5/10* (2013.01); *C12N 15/09* (2013.01)

(58) Field of Classification Search
None
See application file for complete search history.

(56) References Cited

U.S. PATENT DOCUMENTS

| 2002/0061543 A1 | 5/2002 | Ross |
| 2003/0236209 A1 | 12/2003 | Foy et al. |
| 2006/0024692 A1 | 2/2006 | Nakamura et al. |
| 2008/0050378 A1 | 2/2008 | Nakamura et al. |
| 2009/0202576 A1 | 8/2009 | Tahara et al. |
| 2009/0208514 A1 | 8/2009 | Nakamura et al. |
| 2009/0317392 A1 | 12/2009 | Nakamura et al. |
| 2010/0173317 A1 | 7/2010 | Nakamura et al. |
| 2011/0027302 A1 | 2/2011 | Tahara et al. |
| 2011/0223687 A1 | 9/2011 | Nakamura et al. |
| 2012/0021946 A1 | 1/2012 | Nakamura et al. |
| 2012/0308590 A1 | 12/2012 | Nishimura et al. |
| 2016/0114018 A1 | 4/2016 | Nishimura et al. |

FOREIGN PATENT DOCUMENTS

| JP | 2004-000216 A | 1/2004 |
| JP | 2005-522209 A | 7/2005 |
| JP | 2008-530975 A | 8/2008 |
| JP | 2013-511958 A | 4/2013 |
| RU | 2012/127358 A | 1/2014 |
| WO | 1999/046594 A | 9/1999 |
| WO | 02/20036 A | 3/2002 |
| WO | 2003/086175 A2 | 10/2003 |
| WO | 2004/031413 A | 4/2004 |
| WO | 2005/090603 A | 9/2005 |
| WO | 2006/090810 A | 8/2006 |
| WO | 2007/013665 A | 2/2007 |
| WO | 2007/013671 A | 2/2007 |

(Continued)

OTHER PUBLICATIONS

Johnson, Clin Microbiol Rev, 7:277-289, 1994.*
Adams, H. et al., "Prediction of binding to MHC class I molecules," J. Immunol. Methods, 185(2):181-90, Sep. 25, 1995.
Belli, F. et al., "Vaccination of metastatic melanoma patients with autologous tumor-derived heat shock protein gp96-peptide complexes: clinical and immunologic findings," J. Clin. Oncol., 20(20):4169-80, Oct. 15, 2002.
Boon, T., "Tumor antigens recognized by cytolytic T lymphocytes: present perspectives for specific immunotherapy," Int. J. Cancer, 54(2):177-80, May 8, 1993.
Boon, T. et al., "Human tumor antigens recognized by T lymphocytes," J. Exp. Med., 183(3):725-9, Mar. 1, 1996.
Butterfield, Lisa H. et al., "Generation of human T-cell responses to an HLA-A2.1-restricted peptide epitope derived from a-fetoprotein," Cancer Res., 59(13):3134-42, Jul. 1, 1999.

(Continued)

*Primary Examiner* — Mark Halvorson
(74) *Attorney, Agent, or Firm* — Kilpatrick Townsend & Stockton LLP

(57) ABSTRACT

The present invention provides KOC1-derived epitope peptides having the ability to induce cytotoxic T cells. The present invention further provides polynucleotides encoding the peptides, antigen-presenting cells presenting the peptides, and cytotoxic T cells targeting the peptides, as well as methods of inducing the antigen-presenting cells or CTLs. The present invention also provides compositions and pharmaceutical compositions containing them as an active ingredient. Further, the present invention provides methods of treating and/or preventing cancer, and/or preventing postoperative recurrence thereof, using the peptides, polynucleotides, antigen-presenting cells, cytotoxic T cells or pharmaceutical compositions of the present invention. Methods of inducing an immune response against cancer are also provided.

7 Claims, 16 Drawing Sheets

Specification includes a Sequence Listing.

(56) References Cited

FOREIGN PATENT DOCUMENTS

| WO | 2007/097469 A | 8/2007 |
|---|---|---|
| WO | 2008/007711 A | 1/2008 |
| WO | 2011/067920 A | 6/2011 |
| WO | 2014/188721 A | 11/2014 |

OTHER PUBLICATIONS

Chujoh, Y., et al.; The role of anchor residues in the binding of peptides to HLA-A 1101 molecules; Tissue Antigens; Dec. 1998.; 52(6):501-9.

Coulie, P. et al., "Cytolytic T-cell responses of cancer patients vaccinated with a MAGE antigen," Immunol. Rev., 188:33-42, Oct. 2002.

Dionne, S. et al., "Functional characterization of CTL against gp100 altered peptide ligands," Cancer Immunol. Immunother., 52(4):199-206, Apr. 2003, Epub: Feb. 18, 2003.

Dionne, S. et al., "Her-2/neu altered peptide ligand-induced CTL responses: implications for peptides with increased HLA affinity and T-cell-receptor interaction," Cancer Immunol. Immunother. 53(4):307-14, Apr. 2004, Epub: Nov. 5, 2003.

Falk, K. et al., "Allele-specific motifs revealed by sequencing of self-peptides eluted from MHC molecules," Nature, 351(6324):290-6, May 23, 1991.

Falk, K., et al.; Peptide motifs of HLA-A1, -A11, -A31, and -A33 molecules; Immunogenetics (1994); 40:238-241.

Fujie, T. et al., "A MAGE-1-encoded HLA-A24-binding synthetic peptide induces specific anti-tumor cytotoxic T lymphocytes," Int. J. Cancer, 80(2):169-72, Jan. 18, 1999.

Harris, C., "Structure and function of the p53 tumor suppressor gene: clues for rational cancer therapeutic strategies," J. Natl. Cancer Inst., 88(20):1442-55, Oct. 16, 1996.

Hoffmann, T., et al., "The ability of variant peptides to reverse the nonresponsiveness of T lymphocytes to the wild-type sequence $P53_{264-272}$ epitope," J. Immunol., 168(3):1338-47, Feb. 1, 2002.

International Search Report; International Patent Application No. PCT/JP2015/071829; ISA-Japan Patent Office; dated Oct. 20, 2015.

Kikuchi, M. et al., "Identification of a SART-1-derived peptide capable of inducing HLA-A24-restricted and tumor-specific cytotoxic T lymphocytes," Int. J. Cancer, 81(3):459-66, May 5, 1999.

Kikuchi, T. et al., "Expression profiles of non-small cell lung cancers on cDNA microarrays: identification of genes for prediction of lymph-node metastasis and sensitivity to anti-cancer drugs," Oncogene, 22(14):2192-2205, Apr. 10, 2003.

Kubo, R. et al., "Definition of specific peptide motifs for four major HLA-A alleles," J. Immunol., 152(8):3913-24, Apr. 15, 1994.

Müeller-Pillasch, F. et al., "Cloning of a gene highly overexpressed in cancer coding for a novel KH-domain containing protein," Oncogene, 14(22):2729-33, Jun. 5, 1997.

Nishimura, et al.; IMP-3 Epitope Peptides for Th1 Cells and Vaccines Containing the Same; U.S. Appl. No. 15/692,145, filed Aug. 31, 2017; U.S. Patent and Trademark Office.

Oiso, M. et al., "A newly identified MAGE-3-derived epitope recognized by HLA-A24-restricted cytotoxic T lymphocytes," Int. J. Cancer, 81(3):387-94, May 5, 1999.

Rammensee, H. et al., "MHC ligands and peptide motifs: first listing," Immunogenetics, 41(4):178-228, 1995.

Rosenberg, S. et al., "Cancer immunotherapy: moving beyond current vaccines," Nat Med., 10(9):909-15, Sep. 2004.

Schueler-Furman, O. et al., "Structure-based prediction of binding peptides to MHC class I molecules: application to a broad range of MHC alleles," Protein Sci., 9(9):1838-46, Sep. 2000.

Suda, T. et al., "Identification of human leukocyte antigen-A24-restricted epitope peptides derived from gene products upregulated in lung and esophageal cancers as novel targets for immunotherapy," Cancer Sci., 98(11):1803-8, Nov. 2007.

Tanaka, F. et al., "Induction of antitumor cytotoxic T lymphocytes with a MAGE-3-encoded synthetic peptide presented by human leukocytes antigen-A24," Cancer Res., 57(20):4465-8, Oct. 15, 1997.

Tomita, Y. et al., "Peptides derived from human insulin-like growth factor-ll mRNA binding protein 3 can induce human leukocyte antigen-A2-restricted cytotoxic T lymphocytes reactive to cancer cells," Cancer Sci., 102(1):71-78, Jan. 2011; doi: 10.1111 /j.1349-7006.2010.01780.x; Epub: Nov. 19, 2010.

Van Der Burg, S. et al., "Immunogenicity of peptides bound to MHC class I molecules depends on the MHC-peptide complex stability," J. Immunol., 156(9):3308-14, May 1, 1996.

Vissers, J. et al., "The renal cell carcinoma-associated antigen G250 encodes a human leukocyte antigen (HLA)-A2.1-restricted epitope recognized by cytotoxic T lymphocytes," Cancer Res., 59(21):5554-9, Nov. 1, 1999.

Wang, T. et al., "Identification of genes differentially over-expressed in lung squamous cell carcinoma using combination of cDNA subtraction and microarray analysis," Oncogene, 19(12):1519-28, Mar. 16, 2000.

Zaremba, S. et al., "Identification of an enhancer agonist cytotoxic T lymphocyte peptide from human carcinoembryonic antigen," Cancer Res., 57(20):4570-7, Oct. 15, 1997.

* cited by examiner

KOC1-DERIVED PEPTIDE AND VACCINE INCLUDING SAME

CROSS-REFERENCE TO RELATED APPLICATIONS

The present application is a divisional of U.S. application Ser. No. 15/501,125, filed Feb. 1, 2017, which application is a § 371 National Phase Application of PCT/JP2015/071829, filed Jul. 31, 2015, which application claims priority to JP 2014-158919, filed Aug. 4, 2014, JP 2014-158920, filed Aug. 4, 2014, and JP 2014-158921, filed Aug. 4, 2014, the disclosures of which are hereby incorporated by reference in their entireties for all purposes.

REFERENCE TO A SEQUENCE LISTING

The Substitute Sequence Listing written in file SubstituteSequenceListing_087331-029800US-1036284.tx created on Apr. 19, 2017, 39,504 bytes, machine format IBM-PC, MS-Windows operating system, is hereby incorporated by reference in its entirety for all purposes.

TECHNICAL FIELD

The present invention relates to the field of biological science, more specifically to the field of cancer therapy. In particular, the present invention relates to novel peptides that are effective as cancer vaccines, methods for either or both of treating and preventing tumors using the peptide(s), and pharmaceutical compositions comprising the peptide(s).

The present application claims the benefit of Japanese patent applications filed on Aug. 4, 2014 (Japanese Patent Application Nos. 2014-158919, 2014-158920, and 2014-158921), the entire contents of which are incorporated by reference herein.

BACKGROUND ART

Cytotoxic T lymphocytes (CTLs) have been shown to recognize epitope peptides derived from the tumor-associated antigens (TAAs) found on the major histocompatibility complex (MHC) class I molecule, and then kill the tumor cells. Since the discovery of the melanoma antigen (MAGE) family, many other TAAs have been discovered through immunological approaches (NPL1: Boon T, Int J Cancer 1993 May 8, 54(2): 177-80; NPL2: Boon T & van der Bruggen P, J Exp Med 1996 Mar. 1, 183(3): 725-9). Some of these TAAs are currently undergoing clinical development as immunotherapeutic targets.

In several of these TAAs, epitope peptides that can be recognized by CTLs are identified and their application in immunotherapy for various types of cancer is anticipated (NPL3: Harris C C, J Natl Cancer Inst 1996 Oct. 16, 88(20): 1442-55; NPL4: Butterfield L H et al., Cancer Res 1999 Jul. 1, 59(13): 3134-42; NPLS: Vissers J L et al., Cancer Res 1999 Nov. 1, 59(21): 5554-9; NPL6: van der Burg S H et al., J Immunol 1996 May 1, 156(9) 3308-14; NPL7: Tanaka F et al., Cancer Res 1997 Oct. 15, 57(20): 4465-8; NPL8: Fujie T et al., Int J Cancer 1999 Jan. 18, 80(2): 169-72; NPL9: Kikuchi M et al., Int J Cancer 1999 May 5, 81(3): 439-66; NPL10: Oiso M et al., Int J Cancer 1999 May 5, 81(3): 387-94). Until now, several clinical trials using these TAA-derived CTL epitope peptides have been reported. Unfortunately, many of these clinical trials show a low objective response rate (NPL11: Belli F et al., J Clin Oncol 2002 Oct. 15, 20(20): 4169-80; NPL12: Coulie P G et al., Immunol Rev 2002 October, 188: 33-42; NPL13: Rosenberg S A et al., Nat Med 2004 September, 10(9): 909-15). Therefore, there is still demand for identification of novel CTL epitopes that can be used in cancer immunotherapy.

KOC1 (insulin-like growth factor II mRNA binding protein 3 also described as IGF2BP3 or IMP-3; reference sequence: GeneBank Accession Number NM_006547.2 (SEQ ID NO: 109)) is identified as a gene up-regulated in lung cancer by gene expression profile analysis using a genome-wide cDNA microarray containing 23,040 genes (NPL14: Kikuchi T et al., Oncogene. 2003 Apr. 10; 22(14): 2192-205; PTL1: WO2004/031413). The KOC1 expression is observed to be up-regulated specifically in tumor cells in over 90% of lung cancer patients, but it is not expressed in other normal important organs except the testis and placenta. Further, it is shown that cell proliferation in KOC1-expressing cancer cell lines is suppressed as a result of down-regulation of the KOC1 expression by RNA interference.

Recently, KOC1-derived HLA-A24-restricted CTL epitope peptides (PTL2: WO2006/090810; NPL15: Suda T et al., Cancer Sci. 2007 November; 98(11): 1803-8) and HLA-A2-restricted CTL epitope peptides (PTL3: WO2011/067920; NPL16: Tomita Y et al., Cancer Sci. 2011 January; 102(1): 71-8) have been identified. These peptides are effective in cancer patients having the HLA-A24 type or HLA-A2 type, but cannot be expected to have effect on cancer patients who do not have these HLA types.

CITATION LIST

Patent Literature

[PTL 1] WO2004/031413
[PTL2] WO2006/090810
[PTL3] WO2011/067920

Non Patent Literature

[NPL 1] Boon T, Int J Cancer 1993 May 8, 54(2): 177-80
[NPL 2] Boon T & van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8
[NPL 8] Fujie T et al., Int J Cancer 1999 Jan. 18, 80(2): 169-72
[NPL 9] Kikuchi M et al., Int J Cancer 1999 May 5, 81(3): 459-66
[NPL 10] Oiso M et al., Int J Cancer 1999 May 5, 81(3): 387-94
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15
[NPL 14] Kikuchi T et al., Oncogene. 2003 Apr. 10; 22(14): 2192-205
[NPL 15] Suda T et al., Cancer Sci. 2007 November; 98(11): 1803-8

[NPL 16] Tomita Y et al., Cancer Sci. 2011 January; 102(1): 71-8

SUMMARY OF THE INVENTION

The present invention relates to peptides that can induce CTLs specific to KOC1-expressing cells. When these peptides are presented on antigen-presenting cells (APCs) by the human leukocyte antigen (HLA), CTLs that show a specific cytotoxic activity against KOC1-expressing cells are induced. KOC1-derived peptides that have been identified so far to have CTL-inducing ability (CTL inducibility) are either HLA-A2-restricted or HLA-A24-restricted peptides, and cannot induce CTLs against cells that do not express these HLAs. Therefore, conventional peptides are not suitable for performing immunotherapy in subjects that do not have these HLAs. HLA-A11 and HLA-A33 are alleles commonly seen in Asians (Sette A, Sidney J., Immunogenetics 1999, 50: 201-12), and HLA-A03 and HLA-A01 are alleles commonly seen in Caucasians (Cao et al., Hum Immunol 2001; 62(9): 1009-30). It is desirable to administer HLA-A11-restricted peptides to HLA-A11-positive subjects, HLA-A33-restricted peptides to HLA-A33-positive subjects, HLA-A03-restricted peptides to HLA-A03-positive subjects, and HLA-A01-restricted peptides to HLA-A01-positive subjects. Hence, the present invention relates to KOC1-derived peptides with CTL-inducing ability that are restrictive to HLA-A11, HLA-A33, HLA-A03, or HLA-A01. Based on results disclosed herein, the peptides of the present invention have been proven to be epitope peptides that can induce a potent and specific immune response against cells expressing KOC1 and HLA-A11, HLA-A33, HLA-A03, or HLA-A01.

Therefore, one of the objectives of the present invention is to provide KOC1-derived peptides that can induce CTLs in an HLA-A11-, HLA-A33-, HLA-A03- or HLA-A01-restrictive manner. These peptides can be used to induce CTLs in vitro, ex vivo or in vivo, or can be used to administer to subjects for the purpose of inducing an immune response against KOC1-expressing cancer cells. Preferable peptides are peptides comprising the amino acid sequence selected from among SEQ ID NOs: 5, 28, 30, 32, 61, 62, 63, 64, 67, 74, 77, 52, 79, 80, 85, 27, 86, 87, 90, 92, 46, 95 and 41; more preferable peptides are nonapeptides or decapeptides; and even more preferable peptides are peptides consisting of the amino acid sequence selected from among SEQ ID NOs: 5, 28, 30, 32, 61, 62, 63, 64, 67, 74, 77, 52, 79, 80, 85, 27, 86, 87, 90, 92, 46, 95 and 41. The peptides of the present invention encompass peptides in which one, two or more amino acid(s) is/are substituted, deleted, inserted and/or added, as long as the resultant modified peptides retain the CTL-inducing ability of the original peptide.

The present invention further provides isolated polynucleotides encoding any one of the peptides of the present invention. Similar to the peptides of the present invention, these polynucleotides can be used for inducing APCs with CTL-inducing ability, and can be administered to subjects for inducing an immune response against KOC1-expressing cancer cells.

The present invention also provides compositions comprising one or more types of peptides of the present invention, one or more types of polynucleotides encoding one or more types of peptides of the present invention, APCs of the present invention, exosomes presenting peptides of the present invention, and/or CTLs of the present invention. The compositions of the present invention are preferably pharmaceutical compositions. The pharmaceutical compositions of the present invention can be used for treating and/or preventing cancer, as well as preventing postoperative recurrence thereof. They can also be used for inducing an immune response against cancer. When administered to a subject, a peptide of the present invention is presented on the surface of an APC, and as a result CTLs targeting the peptide are induced. Therefore, another objective of the present invention is to provide compositions for inducing CTLs, wherein the compositions comprise one or more types of peptides of the present invention, one or more types of polynucleotides encoding one or more types of peptides of the present invention, APCs of the present invention, and/or exosomes presenting peptides of the present invention.

A further objective of the present invention is to provide methods of inducing APCs having CTL-inducing ability, wherein the methods comprise a step of contacting one or more types of peptides of the present invention with an APC, or a step of introducing a polynucleotide encoding any one peptide of the present invention into an APC.

The present invention further provides a method of inducing CTLs, comprising a step of co-culturing a CD8-positive T cell with an APC that presents on its surface a complex of an HLA antigen and a peptide of the present invention, a step of co-culturing a CD8-positive T cell with an exosome that presents on its surface a complex of an HLA antigen and a peptide of the present invention, or a step of introducing into a CD8-positive T cell a vector comprising a polynucleotide encoding each subunit of a T cell receptor (TCR) capable of binding to a peptide of the present invention presented by an HLA antigen on a cell surface. The preferred HLA antigen in the present invention is HLA-A11, HLA-A33, HLA-A03 or HLA-A01.

A further objective of the present invention is to provide isolated APCs that present on their surface a complex of an HLA antigen and a peptide of the present invention. The present invention further provides isolated CTLs targeting a peptide of the present invention. These APCs and CTLs can be used in immunotherapy for KOC1-expressing cancers. In the present invention, the cancer to be subjected to immunotherapy is, for example, a cancer present in patients who have a homozygote or heterozygote of HLA-A11, HLA-A33, HLA-A03 or HLA-A01. That is, the present invention provides immunotherapy for cancers expressing KOC1 and at least one HLA antigen selected from HLA-A11, HLA-A33, HLA-A03 and HLA-A01.

Another objective of the present invention is to provide methods of inducing an immune response against cancer in a subject, wherein the methods comprise a step of administering to the subject a peptide(s) of the present invention, a polynucleotide(s) encoding the peptide(s), an APC(s) of the present invention, an exosome(s) presenting a peptide(s) of the present invention, and/or a CTL(s) of the present invention. Another objective of the present invention is to provide methods of treating and/or preventing cancer, as well as preventing postoperative recurrence thereof in a subject, wherein the methods comprise a step of administering to the subject a peptide(s) of the present invention, a polynucleotide(s) encoding the peptide(s), an APC(s) of the present invention, an exosome(s) presenting a peptide(s) of the present invention, and/or a CTL(s) of the present invention.

In addition to the above, other objects and features of the present invention will become more fully apparent when the following detailed description is read in conjunction with the accompanying figures and examples. However, it is to be understood that both the foregoing summary of the present invention and the following detailed description are of exemplified embodiments, and not restrictive of the present invention or other alternate embodiments of the present invention. In particular, while the present invention is described herein with reference to a number of specific embodiments, it will be appreciated that the description is illustrative of the present invention and is not constructed as limiting of the present invention. Various modifications and applications may occur to those who are skilled in the art, without departing from the spirit and the scope of the present invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

MODE FOR CARRYING OUT THE INVENTION

Description of Embodiments

Figure 1:
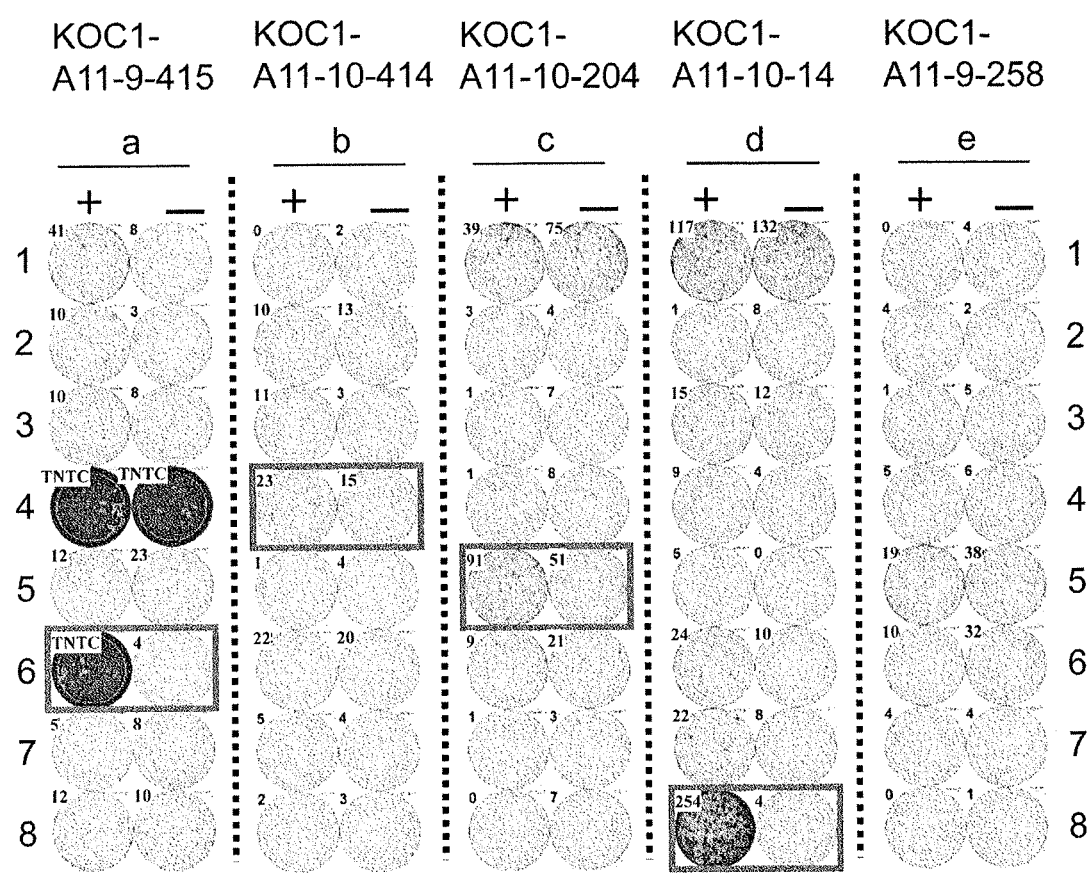
FIG. 1 consists of photos (a) to (e) showing results of an interferon (IFN)-gamma enzyme-linked immunospot (ELISPOT) assay in CTLs induced using peptides derived from KOC1. In comparison with the control, CTLs in Well #6 with KOC1-A11-9-415 (SEQ ID NO: 5) (a), Well #4 with KOC1-A11-10-414 (SEQ ID NO: 28) (b), Well #5 with KOC1-A11-10-204 (SEQ ID NO: 30) (c), and Well #8 with KOC1-A11-10-14 (SEQ ID NO: 32) (d) showed potent IFN-gamma production. In these photos, the square on the wells show that cells from the respective wells were propagated for the establishment of CTL lines. In contrast, KOC1-A11-9-258 (SEQ ID NO: 1) (e) is shown as an example of typical negative data where there was no specific IFN-gamma production. In the figure, "+" shows IFN-gamma production against target cells pulsed with an appropriate peptide; and "−" shows IFN-gamma production against target cells that have not been pulsed with any peptides.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

I. Definitions

The words "a", "an", and "the" as used herein mean "at least one" unless otherwise specifically indicated.

The terms "isolated" and "purified" used in relation with a substance (for example, peptide, antibody, polynucleotide or such) indicate that the substance does not substantially contain at least one substance that may else be included in a natural source. Thus, an isolated or purified peptide refers to a peptide that does not substantially contain another cellular material, for example, carbohydrate, lipid and other contaminating proteins from the cell or tissue source from which the peptide is derived. When the peptide is chemically synthesized, an isolated or purified peptide refers to a peptide that does not substantially contain a precursor substance or another chemical substance. The phrase "does not substantially contain a cellular material" includes peptide preparations in which the peptide is separated from cellular components of the cells from which it is isolated or recombinantly produced. Thus, a peptide that does not substantially contain a cellular material encompasses peptide preparations that contain less than about 30%, 20%, 10%, 5%, 3%, 2% or 1% (dry weight basis) of other cellular materials. When the peptide is recombinantly produced, an isolated or purified peptide does not substantially contain culture medium, which encompasses peptide preparations that contain culture medium less than about 20%, 10%, or 5%, 3%, 2% or 1% (dry weight basis) of the volume of the peptide preparation. When the peptide is chemically synthesized, an isolated or purified peptide does not substantially contain a precursor substance or other chemical substances, which encompasses peptide preparations that contain a precursor substance or other chemical substances less than about 30%, 20%, 10%, 5%, 3%, 2% or 1% (dry weight basis) of the volume of the peptide preparation. That a particular peptide preparation is an isolated or purified peptide can be confirmed, for example, by the appearance of a single band following sodium dodecyl sulfate (SDS)-polyacrylamide gel electrophoresis and Coomassie Brillliant Blue staining or such of the gel. In a preferred embodiment, the peptides and polynucleotides of the present invention are isolated or purified.

The terms "polypeptide", "peptide" and "protein" are used interchangeably herein, and refer to polymers of amino acid residues. These terms are applied to also non-naturally occurring amino acid polymers comprising one or more non-naturally occurring amino acid residues, in addition to naturally occurring amino acid polymers. Non-naturally occurring amino acids include amino acid analogs, amino acid mimetics, and such.

The term "amino acid" as used herein refers to naturally occurring amino acids, as well as amino acid analogs and amino acid mimetics that functions similarly to the naturally occurring amino acids. Naturally occurring amino acids are those encoded by the genetic code, as well as those modified after translation in cells (e.g., hydroxyproline, gamma-carboxyglutamate, and O-phosphoserine, etc.). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine sulfoxide, methionine methyl sulfonium, and such). The phrase "amino acid mimetic" refers to chemical compounds that have different structures but similar functions to general amino acids. Amino acids can be either L-amino acids or D-amino acids, and the peptides of the present invention are preferably L-amino acid polymers.

The terms "polynucleotide" and "nucleic acid" are used interchangeably herein, and refer to a polymer of nucleotides.

The term "composition" used in the present specification is intended to encompass products that include specified ingredients in specified amounts, and any products generated directly or indirectly from combination of specified ingredients in the specified amounts. When the composition is a pharmaceutical composition, the term "composition" is intended to encompass products including active ingredient(s) and inert ingredient(s), as well as any products generated directly or indirectly from combination, complexation or aggregation of any two or more ingredients, from dissociation of one or more ingredients, or from other types of reactions or interactions of one or more ingredients. Thus, the pharmaceutical compositions of the present invention encompass any compositions made by admixing compounds or cells of the present invention with a pharmaceutically or physiologically acceptable carrier. Without being limited thereto, the terms "pharmaceutically acceptable carrier" or "physiologically acceptable carrier" used in the present specification include liquid or solid bulking agents, diluents, excipients, solvents, and encapsulation materials; and mean pharmaceutically or physiologically acceptable materials, compositions, substances or media.

Unless otherwise specified, the term "cancer" refers to a cancer that overexpresses the KOC1 gene; and examples thereof include bladder cancer, cervical cancer, cholangiocellular cancer, chronic myeloid leukemia (CML), colon cancer, rectum cancer, esophagus cancer, diffuse gastric cancer, non-small-cell lung cancer, small-cell lung cancer, lymphoma, osteosarcoma, ovarian cancer, kidney cancer, head and neck cancer, soft tissue tumor, testis cancer and such, without being limited thereto. In an exemplary embodiment, the "cancer" is a cancer that expresses KOC1 and HLA-A11, HLA-A33, HLA-A03 and/or HLA-A01.

Unless otherwise specified, the terms "cytotoxic T lymphocyte" and "cytotoxic T cell" and "CTL" are used interchangeably herein. Unless otherwise specifically indicated, they refer to a sub-group of T lymphocytes that can recognize non-self cells (for example, tumor/cancer cells, virus-infected cells) and induce the death of such cells.

Unless otherwise specified, the term "HLA-A11" refers to the HLA-A11 type which includes subtypes such as HLA-A*1101, HLA-A*1102, HLA-A*1103, and HLA-A*1104.

Unless otherwise specified, the term "HLA-A33" refers to the HLA-A33 type which includes subtypes such as HLA-A*3303, HLA-A*3301, and HLA-A*3304.

Unless otherwise specified, the term "HLA-A03" refers to the HLA-A03 type which includes subtypes such as HLA-A*0301, HLA-A*0302, and HLA-A*0305.

Unless otherwise specified, the term "HLA-A01" refers to the HLA-A01 type which includes subtypes such as HLA-A*0101, HLA-A*0102, HLA-A*0103, and HLA-A*0104.

In the context of a subject or patient, the phrase "HLA antigen of a subject (or patient) is HLA-A11" used herein refers to that a subject or patient has the HLA-A11 antigen gene homozygously or heterozygously as the MHC (Major Histocompatibility Complex) Class I molecule, and that the HLA-A11 antigen is expressed in the cells of the subject or patient as the HLA antigen. Similarly, the phrases "HLA antigen of a subject (or patient) is HLA-A33", "HLA antigen of a subject (or patient) is HLA-A03" and "HLA antigen of a subject (or patient) is HLA-A01" used herein refer to, respectively, that a subject or patient has the HLA-A33 antigen gene homozygously or heterozygously as the MHC (Major Histocompatibility Complex) Class I molecule and that the HLA-A33 antigen is expressed as the HLA antigen in the cells of the subject or patient; that a subject or patient has the HLA-A03 antigen gene homozygously or heterozygously as the MHC (Major Histocompatibility Complex) Class I molecule and that the HLA-A03 antigen is expressed as the HLA antigen in the cells of the subject or patient; and that a subject or patient has the HLA-A01 antigen gene homozygously or heterozygously as the MHC (Major Histocompatibility Complex) Class I molecule and that the HLA-A01 antigen is expressed as the HLA antigen in the cells of the subject or patient.

As long as the methods and compositions of the present invention are useful in the context of cancer "treatment", the treatment is considered "efficacious" when it achieves clinical advantages, for example, reduction in the size, spreading or metastatic ability of cancer, retardation of cancer progression, alleviation of clinical symptoms of cancer, prolongation of survival period, suppression of postoperative recurrence in a subject. When the treatment is applied prophylactically, "efficacious" means that the treatment retards or prevents cancer formation, or prevents or alleviates clinical symptoms of cancer. Effectiveness is determined in relation to any publicly known method for diagnosing or treating a specific tumor type.

As long as the methods and compositions of the present invention are useful in the context of cancer "prevention (prophylaxis)", the term "prevention (prophylaxis)" herein includes any work that eases the load of cancer-associated mortality or morbidity. Prevention (Prophylaxis) can be carried out at the "primary, secondary and tertiary prevention (prophylaxis) levels". Whereas the primary prevention (prophylaxis) avoids the development of a disease, prevention (prophylaxis) at the secondary and tertiary levels encompasses prevention (prophylaxis) of disease progression and appearance of symptoms, as well as workings intended to reduce adverse effects of the existing disease by restoring functions and reducing disease-associated complications. Alternately, prevention (prophylaxis) can include alleviation of severity of a specific disorder, for example, extensive preventive therapy intended to reduce tumor growth and metastasis.

In the context of the present invention, the treatment and/or prevention (prophylaxis) of cancer and/or prevention (prophylaxis) of postoperative recurrence thereof include either of the events such as inhibition of cancer cell proliferation, tumor involution or regression, induction of remission and suppression of cancer development, tumor regression, as well as reduction or inhibition of metastasis, suppression of postoperative recurrence of cancer, and prolongation of survival period. Effective treatment and/or prevention (prophylaxis) of cancer reduce mortality, improve prognosis of an individual with cancer, reduce the blood levels of tumor markers, and alleviate detectable symptoms associated with cancer. For example, alleviation or improvement of symptoms constitutes effective treatment and/or prevention (prophylaxis), and includes a condition in which the symptoms are stable or alleviated by 10%, 20%, 30% or more.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an "antibody" herein is used in the broadest sense and specifically covers intact monoclonal antibodies, polyclonal antibodies, multispecific antibodies (e.g., bispecific antibodies) formed from two or more intact antibodies, and antibody fragments so long as they exhibit the desired biological activity. An "antibody" may be antibodies of all classes (e.g., IgA, IgD, IgE, IgG and IgM).

Unless otherwise specified, the technical terms and scientific terms used herein all have the same meanings as terms commonly understood by one of ordinary skill in the art to which the present invention belongs.

II. Peptides

HLA-A11 and HLA-A33 are alleles commonly seen in Asians (Sette A, Sidney J., Immunogenetics 1999, 50: 201-12), and HLA-A03 and HLA-A01 are alleles commonly seen in Caucasians (Cao et al., Hum Immunol 2001; 62(9): 1009-30). Thus, an effective method of treating KOC1-expressing cancers for a great population of Asians or Caucasians can be provided by providing KOC1-derived CTL-inducing peptides restricted to HLA-A11, HLA-A33, HLA-A03, or HLA-A01. Thus, the present invention provides KOC1-derived peptides that are capable of inducing CTLs in an HLA-A11-, HLA-A33-, HLA-A03-, or HLA-A01-restrictive manner.

The peptides of the present invention are KOC1-derived peptides that are capable of inducing CTLs in an HLA-A11-, HLA-A33-, HLA-A03-, or HLA-A01-restrictive manner. Peptides capable of inducing CTLs in an HLA-A11-restrictive manner include peptides having the amino acid sequence selected from among SEQ ID NOs: 5, 28, 30 and 32. Similarly, peptides capable of inducing CTLs in an HLA-A33-restrictive manner include peptides having the amino acid sequence selected from among SEQ ID NOs: 61, 62, 63, 64, 67, 74, 77, 52, 79, 80 and 85. Similarly, peptides capable of inducing CTLs in an HLA-A03-restrictive manner include peptides having the amino acid sequence selected from among SEQ ID NOs: 27, 30 and 52. Similarly, peptides capable of inducing CTLs in an HLA-A01-restrictive manner include peptides having the amino acid sequence selected from among SEQ ID NOs: 86, 87, 90, 92, 46, 95, and 41.

CTLs having a cytotoxic activity specific to these peptides can be established by in vitro stimulation of T cells by dendritic cells (DCs) pulsed with these peptides. The established CTLs show a specific cytotoxic activity against target cells pulsed with each of the peptides.

The KOC1 gene is overexpressed in cancer cells such as cancer cells in, for example, bladder cancer, cervical cancer, cholangiocellular cancer, chronic myeloid leukemia (CML), colon cancer, rectum cancer, esophagus cancer, diffuse gastric cancer, non-small-cell lung cancer, small-cell lung cancer, lymphoma, osteosarcoma, ovarian cancer, kidney cancer, head and neck cancer, soft tissue tumor, testis cancer and such, but is not expressed in most normal organs. It is thus an excellent target for immunotherapy. Therefore, the peptides of the present invention can be suitably used for cancer immunotherapy. A preferred peptide is a nonapeptide (a peptide consisting of 9 amino acid residues) or a decapeptide (a peptide consisting of 10 amino acid residues), and it is more preferably a peptide consisting of the amino acid sequence selected from among SEQ ID NOs: 5, 28, 30, 32, 61, 62, 63, 64, 67, 74, 77, 52, 79, 80, 85, 27, 86, 87, 90, 92, 46, 95, and 41. For example, a peptide having the amino acid sequence of SEQ ID NO: 32 is suitable for induction of CTLs that show a specific cytotoxic activity against cells expressing HLA-A11 and KOC1, and can be suitably used for cancer immunotherapy for HLA-A11-positive patients. Furthermore, for example, a peptide having the amino acid sequence selected from among SEQ ID NOs: 64, 67 and 77 is suitable for induction of CTLs that show a specific cytotoxic activity against cells expressing HLA-A33 and KOC1, and can be suitably used for cancer immunotherapy for HLA-A33-positive patients. In addition, for example, a peptide having the amino acid sequence of SEQ ID NO: 27 is suitable for induction of CTLs that show a specific cytotoxic activity against cells expressing HLA-A03 and KOC1, and can be suitably used for cancer immunotherapy for HLA-A03-positive patients. Additionally, for example, a peptide having the amino acid sequence of SEQ ID NO: 86 is suitable for induction of CTLs that show a specific cytotoxic activity against cells expressing HLA-A01 and KOC1, and can be suitably used for cancer immunotherapy for HLA-A01-positive patients. In a more preferred embodiment, the peptide of the present invention is a peptide consisting of the amino acid sequence selected from among SEQ ID NOs: 32, 64, 67, 77, 27, and 86.

For the peptides of the present invention, an additional amino acid residue(s) can be made to adjoin the amino acid sequence of the peptide of the present invention, as long as the resultant peptides retain the CTL-inducing ability of the original peptide. The additional amino acid residue(s) may be composed of any types of amino acid(s), as long as they do not impair the CTL-inducing ability of the original peptide. Therefore, the peptides of the present invention encompass peptides having CTL-inducing ability, comprising the amino acid sequence selected from among SEQ ID NOs: 5, 28, 30, 32, 61, 62, 63, 64, 67, 74, 77, 52, 79, 80, 85, 27, 86, 87, 90, 92, 46, 95, and 41. Such peptides are, for example, less than about 40 amino acids, in many cases less than about 20 amino acids, and usually less than about 15 amino acids. Therefore, if the original peptide is a nonapeptide, the peptide of the present invention encompasses peptides that are 10 amino-acid long or 11-40 amino-acid long, which are produced by adjoining additional amino acid(s) to the peptide. Furthermore, if the original peptide is a decapeptide, the peptide of the present invention encompasses peptides that are 11-40 amino-acid long, which are produced by adjoining additional amino acid(s) to the peptide. Such a peptide can be, for example, a peptide that is 11-20 amino-acid long or a peptide that is 11-15 amino-acid long. A preferred example of an additional amino acid residue(s) is an amino acid residue(s) adjacent to the amino acid sequence of the peptide of the present invention in the full-length amino acid sequence of KOC1 (for example, SEQ ID NO: 110). Therefore, the peptides of the present invention encompass peptides comprising the amino acid sequence selected from among SEQ ID NOs: 5, 28, 30, 32, 61, 62, 63, 64, 67, 74, 77, 52, 79, 80, 85, 27, 86, 87, 90, 92, 46, 95, and 41, and wherein the peptides are peptide fragments of KOC1 and have CTL-inducing ability.

In general, modifications of one, two or more amino acids in a certain peptide do not affect the functions of the peptide, or in some cases even enhance the desired functions of the original peptide. In fact, modified peptides (i.e., peptides composed of the amino acid sequence in which one, two or several amino acid residues are modified (i.e., substituted, deleted, inserted, and/or added) compared to the original reference sequence) are known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention can be peptides comprising the amino acid sequence in which one, two or several amino acids are substituted, deleted, inserted and/or added to the amino acid sequence selected from among SEQ ID NOs: 5, 28, 30, 32, 61, 62, 63, 64, 67, 74, 77, 52, 79, 80, 85, 27, 86, 87, 90, 92, 46, 95, and 41 and having CTL-inducing ability.

On skilled in the art can recognize that individual substitutions to an amino acid sequence that alter a single amino acid or a small percentage of amino acids tend to result in the conservation of the properties of the original amino acid side chain(s). Those are frequently referred to as "conservative substitutions" or "conservative modifications"; and modification of a protein by "conservative substitution" or "conservative modification" may result in a modified protein that has similar functions as the original protein. Tables of conservative substitutions presenting functionally similar amino acids are well known in the art. Examples of amino acid side chain characteristics that functionally resemble include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also encompassed in peptides of the present invention. However, peptides of the present invention are not restricted thereto and can include non-conservative modifications, so long as the modified peptide retains the CTL-inducing ability of the original peptide. Furthermore, modified peptides do not exclude CTL inducible peptides derived from polymorphic variants, interspecies homologues, and alleles of KOC1.

So long as a peptide retains the CTL-inducing ability of an original peptide, one can modify (i.e., substitute, delete, insert and/or add) a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably 15% or less, even more preferably 10% or less or 1 to 5%.

When used in the context of immunotherapy, peptides of the present invention are presented on the surface of a cell or exosome, preferably as a complex with an HLA antigen. Therefore, it is preferable that the peptides of the present invention possess high binding affinity to the HLA antigen. To that end, the peptides can be modified by substitution, deletion, insertion, and/or addition of the amino acid residues to yield a modified peptide having improved binding affinity. Since the regularity of the sequences of peptides displayed by binding to HLA antigens is already known (Falk, et al., Immunogenetics 1994 40 232-41; Chujoh, et al., Tissue Antigens 1998: 52: 501-9; Takiguchi, et al., Tissue Antigens 2000: 55: 296-302.), modifications based on such regularity can be introduced into the peptides of the present invention.

For example, in peptides having binding affinity for HLA Class I, the second amino acid from the N terminus and the C-terminal amino acid are generally anchor residues involved in the binding to HLA Class I (Rammensee H G, et al., Immunogenetics. 1995; 41(4): 178-228.). For example, for HLA-A11, threonine, valine, isoleucine, leucine, phenylalanine, and tyrosine for the second amino acid from the N terminus, and lysine and arginine for the C-terminal amino acid are known as anchor residues with high binding affinity for HLA-A11 (Falk, et al., Immunogenetics 1994, 40: 232-41; Chujoh, et al., Tissue Antigens 1998: 52: 501-9). Further, in HLA-A11, there is auxiliary anchor residues at positions 3 and 7 from the N terminus; and it is known that leucine, phenylalanine, tyrosine, isoleucine, and alanine are preferred as the third amino acid from the N terminus, and that leucine, isoleucine, tyrosine, valine and phenylalanine are preferred as the seventh amino acid from the N terminus (Falk, et al., Immunogenetics 1994, 40: 232-41; Chujoh, et al., Tissue Antigens 1998: 52: 501-9). Thus, to maintain or enhance the HLA-A11-binding affinity, there is a possibility that it is desirable to substitute the second amino acid from the N terminus with threonine, valine, isoleucine, leucine, phenylalanine, or tyrosine, and/or to substitute the C-terminal amino acid with lysine or arginine. Further, there is a possibility that it is also desirable to substitute the third amino acid from the N terminus with leucine, phenylalanine, tyrosine, isoleucine, or alanine, and/or to substitute the seventh amino acid from the N terminus with leucine, isoleucine, tyrosine, valine or phenylalanine. Thus, peptides with CTL-inducing ability, comprising an amino acid sequence in which, in the amino acid sequence selected from among SEQ ID NOs: 5, 28, 30 and 32, the second amino acid from the N terminus is substituted with threonine, valine, isoleucine, leucine, phenylalanine, or tyrosine; the third amino acid from the N terminus is substituted with leucine, phenylalanine, tyrosine, isoleucine, or alanine; the seventh amino acid from the N terminus is substituted with leucine, isoleucine, tyrosine, valine or phenylalanine; and/or the C-terminal amino acid is substituted with lysine or arginine are encompassed by the peptides of the present invention. In a preferred embodiment, the peptide of the present invention can be a peptide having CTL-inducing ability that consists of an amino acid sequence in which, in the amino acid sequence selected from among SEQ ID NOs: 5, 28, 30 and 32, the second amino acid from the N terminus is substituted with threonine, valine, isoleucine, leucine, phenylalanine, or tyrosine; the third amino acid from the N terminus is substituted with leucine, phenylalanine, tyrosine, isoleucine, or alanine; the seventh amino acid from the N terminus is substituted with leucine, isoleucine, tyrosine, valine or phenylalanine; and/or the C-terminal amino acid is substituted with lysine or arginine. That is, the peptides of the present invention encompass peptides having CTL-inducing ability, which comprise an amino acid sequence in which one or more substitutions selected from (a) to (d) below are introduced into the amino acid sequence selected from among SEQ ID NOs: 5, 28, 30 and 32:

(a) the second amino acid from the N terminus is substituted with threonine, valine, isoleucine, leucine, phenylalanine, or tyrosine;
(b) the third amino acid from the N terminus is substituted with leucine, phenylalanine, tyrosine, isoleucine, or alanine;
(c) the seventh amino acid from the N terminus is substituted with leucine, isoleucine, tyrosine, valine or phenylalanine; and
(d) the C-terminal amino acid is substituted with lysine or arginine.

In a preferred embodiment, the peptide of the present invention may be a peptide having CTL-inducing ability that consists of an amino acid sequence in which one or more substitutions selected from (a) to (d) above are introduced into the amino acid sequence selected from among SEQ ID NOs: 5, 28, 30 and 32. In the present invention, the preferred number of substitutions is 1, 2, 3 or 4 substitutions selected from (a) to (d) above.

The peptide of the present invention may be a peptide having CTL-inducing ability, which comprises an amino acid sequence in which, in the amino acid sequence selected from among SEQ ID NOs: 5, 28, 30, and 32, the second amino acid from the N terminus is substituted with threonine, valine, isoleucine, leucine, phenylalanine, or tyrosine, and/or the C-terminal amino acid is substituted with lysine or arginine. Preferably, the peptide of the present invention may be a peptide having CTL-inducing ability, which consists of an amino acid sequence in which, in the amino acid sequence selected from among SEQ ID NOs: 5, 28, 30 and 32, the second amino acid from the N terminus is substituted with threonine, valine, isoleucine, leucine, phenylalanine, or tyrosine, and/or the C-terminal amino acid is substituted with lysine or arginine. That is, the peptide of the present invention may be a peptide having CTL-inducing ability, which comprises an amino acid sequence in which one or more substitutions selected from (a) and (b) below are introduced into the amino acid sequence selected from among SEQ ID NOs: 5, 28, 30 and 32:

(a) the second amino acid from the N terminus is substituted with threonine, valine, isoleucine, leucine, phenylalanine, or tyrosine; and
(b) the C-terminal amino acid is substituted with lysine or arginine.

In a preferred embodiment, the peptide of the present invention may be a peptide having CTL-inducing ability, which consists of an amino acid sequence in which one or more substitutions selected from (a) to (b) above are introduced into the amino acid sequence selected from among SEQ ID NOs: 5, 28, 30 and 32. In a more preferred embodiment, the second amino acid from the N terminus is substituted with threonine, valine, isoleucine, or leucine.

In HLA-A33, phenylalanine, tyrosine, alanine, isoleucine, leucine, and valine for the second amino acid from the N terminus, and lysine and arginine for the C-terminal amino acid are known as anchor residues with high binding affinity for HLA-A33 (Falk, et al., Immunogenetics 1994, 40: 232-41; Takiguchi, et al., Tissue Antigens 2000, 55: 296-302). Further, in HLA-A33, the first amino acid residue from the N terminus is also known to function as an anchor residue, and it is known that aspartic acid and glutamic acid is preferred as the first amino acid from the N terminus (Falk, et al., Immunogenetics 1994, 40: 232-41; Takiguchi, et al., Tissue Antigens 2000: 55: 296-302). Thus, to maintain or enhance the HLA-A33-binding affinity, there is a possibility that it is desirable to substitute the first amino acid from the N terminus with aspartic acid or glutamic acid, the second amino acid from the N terminus with phenylalanine, tyrosine, alanine, isoleucine, leucine, or valine, and/or the C-terminal amino acid with lysine or arginine. Therefore, peptides having CTL-inducing ability, which comprise an amino acid sequence in which, in the amino acid sequence selected from among SEQ ID NOs: 61, 62, 63, 64, 67, 74, 77, 52, 79, 80, and 85, the first amino acid from the N terminus is substituted with aspartic acid or glutamic acid, the second amino acid from the N terminus is substituted with phenylalanine, tyrosine, alanine, isoleucine, leucine, or valine, and/or the C-terminal amino acid is substituted with lysine or arginine are encompassed by the peptides of the present invention. In a preferred embodiment, the peptide of the present invention may be a peptide having CTL-inducing ability, which consists of an amino acid sequence in which, in the amino acid sequence selected from among SEQ ID NOs: 61, 62, 63, 64, 67, 74, 77, 52, 79, 80, and 85, the first amino acid from the N terminus is substituted with aspartic acid or glutamic acid, the second amino acid from the N terminus is substituted with phenylalanine, tyrosine, alanine, isoleucine, leucine, or valine, and/or the C-terminal amino acid is substituted with lysine or arginine. That is, the peptides of the present invention encompass a peptide having CTL-inducing ability, which comprises an amino acid sequence in which one or more substitutions selected from (a) to (c) below are introduced into the amino acid sequence selected from among SEQ ID NOs: 61, 62, 63, 64, 67, 74, 77, 52, 79, 80, and 85:

(a) the first amino acid from the N terminus is substituted with aspartic acid or glutamic acid;
(b) the second amino acid from the N terminus is substituted with phenylalanine, tyrosine, alanine, isoleucine, leucine, or valine; and
(c) the C-terminal amino acid is substituted with arginine or lysine.

In a preferred embodiment, the peptide of the present invention may be a peptide having CTL-inducing ability, which consists of an amino acid sequence in which one or more substitutions selected from (a) to (c) above are introduced into the amino acid sequence selected from among SEQ ID NOs: 61, 62, 63, 64, 67, 74, 77, 52, 79, 80, and 85. In the present invention, the preferred number of substitutions is 1, 2 or 3 substitutions selected from (a) to (c) above.

Furthermore, the peptide of the present invention can be a peptide having CTL-inducing ability, which comprises an amino acid sequence in which, in the amino acid sequence selected from among SEQ ID NOs: 61, 62, 63, 64, 67, 74, 77, 52, 79, 80, and 85, the second amino acid from the N terminus is substituted with phenylalanine, tyrosine, alanine, isoleucine, leucine, or valine, and/or the C-terminal amino acid is substituted with arginine or lysine. Preferably, the peptide of the present invention can be a peptide having CTL-inducing ability, which consists of an amino acid sequence in which, in the amino acid sequence selected from among SEQ ID NOs: 61, 62, 63, 64, 67, 74, 77, 52, 79, 80, and 85, the second amino acid from the N terminus is substituted with phenylalanine, tyrosine, alanine, isoleucine, leucine, or valine, and/or the C-terminal amino acid is substituted with arginine or lysine. That is, the peptide of the present invention can be a peptide having CTL-inducing ability, which comprises an amino acid sequence in which one or more substitutions selected from (a) and (b) below are introduced into the amino acid sequence selected from among SEQ ID NOs: 61, 62, 63, 64, 67, 74, 77, 52, 79, 80, and 85:

(a) the second amino acid from the N terminus is substituted with phenylalanine, tyrosine, alanine, isoleucine, leucine, or valine; and
(b) the C-terminal amino acid is substituted with arginine or lysine.

In a preferred embodiment, the peptide of the present invention may be a peptide having CTL-inducing ability, which consists of an amino acid sequence in which one or more substitutions selected from (a) and (b) above are introduced into the amino acid sequence selected from among SEQ ID NOs: 61, 62, 63, 64, 67, 74, 77, 52, 79, 80, and 85. In a more preferred embodiment, the second amino acid from the N terminus is substituted with phenylalanine or tyrosine.

In HLA-A03, leucine, methionine, valine, alanine, isoleucine, serine, and threonine for the second amino acid from the N terminus, and arginine, lysine, tyrosine, and phenylalanine for the C-terminal amino acid are known as anchor residues with high binding affinity for HLA-A03 (Kubo R T. et al., J Immunol. 1994 Apr. 15; 152(8): 3913-24; Sidney J et al., Hum Immunol. 1996 February; 45(2): 79-93; Gambacorti-Passerini C et al., Clin Cancer Res. 1997 May; 3(5): 675-83). Thus, to maintain or enhance the HLA-A03-binding affinity, there is a possibility that it is preferable to substitute the second amino acid from the N terminus with leucine, methionine, valine, alanine, isoleucine, serine or threonine, and/or the C-terminal amino acid with arginine, lysine, tyrosine or phenylalanine. Therefore, peptides having CTL-inducing ability, which comprise an amino acid sequence in which, in the amino acid sequence selected from among SEQ ID NOs: 27, 30, and 52, the second amino acid from the N terminus is substituted with leucine, methionine, valine, alanine, isoleucine, serine or threonine, and/or the C-terminal amino acid is substituted with arginine, lysine, tyrosine or phenylalanine are encompassed by the peptides of the present invention. In a preferred embodiment, the peptides of the present invention may be a peptide having CTL-inducing ability, which consists of an amino acid sequence in which, in the amino acid sequence selected from among SEQ ID NOs: 27, 30, and 52, the second amino acid from the N terminus is substituted with leucine, methionine, valine, alanine, isoleucine, serine or threonine, and/or the C-terminal amino acid is substituted with arginine, lysine, tyrosine or phenylalanine. That is, the peptides of the present invention encompass a peptide having CTL-inducing ability, which comprises an amino acid sequence in which one or more substitutions selected from (a) and (b) below are introduced into the amino acid sequence selected from among SEQ ID NOs: 27, 30, and 52:

(a) the second amino acid from the N terminus is substituted with leucine, methionine, valine, alanine, isoleucine, serine or threonine; and
(b) the C-terminal amino acid is substituted with arginine, lysine, tyrosine or phenylalanine.

In a preferred embodiment, the peptide of the present invention may be a peptide having CTL-inducing ability, which consists of an amino acid sequence in which one or more substitutions selected from (a) and (b) above are introduced into the amino acid sequence selected from among SEQ ID NOs: 27, 30, and 52. In a more preferred embodiment, the second amino acid from the N terminus is substituted with leucine, methionine or valine. In the present invention, the preferred number of substitutions is 1 or 2 substitutions selected from (a) and (b) above.

In HLA-A01, aspartic acid and glutamic acid for the third amino acid from the N terminus, and tyrosine for the C-terminal amino acid are known as anchor residues with high binding affinity for HLA-A01. Further, it is known that there are auxiliary anchor residues at position 2 from the N terminus for HLA-A01 and that threonine and serine are preferred as the second amino acid from the N terminus (Kubo, R. T Journal of Immunology 1994, 152: 3913; Gambacorti-Passerini, C. Clinical Cancer Research 1997, 3: 675-83; Falk, K. Immunogenetics 1994, 40: 238-41). Thus, to maintain or enhance the HLA-A01-binding affinity, there is a possibility that it is desirable to substitute the third amino acid from the N terminus with aspartic acid or glutamic acid, and/or the C-terminal amino acid with tyrosine. Another possibility is that it is desirable to substitute the second amino acid from the N terminus with threonine or serine. Therefore, peptides having CTL-inducing ability, which comprise an amino acid sequence in which, in the amino acid sequence selected from among SEQ ID NOs: 86, 87, 90, 92, 46, 95 and 41, the second amino acid from the N terminus is substituted with threonine or serine, the third amino acid from the N terminus is substituted with aspartic acid or glutamic acid, and/or the C-terminal amino acid is substituted with tyrosine are encompassed by the peptides of the present invention. In a preferred embodiment, the peptide of the present invention may be a peptide having CTL-inducing ability, which consists of an amino acid sequence in which, in the amino acid sequence selected from among SEQ ID NOs: 86, 87, 90, 92, 46, 95 and 41, the second amino acid from the N terminus is substituted with threonine or serine, the third amino acid from the N terminus is substituted with aspartic acid or glutamic acid, and/or the C-terminal amino acid is substituted with tyrosine. That is, the peptides of the present invention encompass a peptide having CTL-inducing ability, which comprises an amino acid sequence in which one or more substitutions selected from (a) to (c) below are introduced into the amino acid sequence selected from among SEQ ID NOs: 86, 87, 90, 92, 46, 95 and 41:
  (a) the second amino acid from the N terminus is substituted with threonine or serine;
  (b) the third amino acid from the N terminus is substituted with aspartic acid or glutamic acid; and
  (c) the C-terminal amino acid is substituted with tyrosine.

In a preferred embodiment, the peptide of the present invention can be a peptide having CTL-inducing ability, which consists of an amino acid sequence in which one or more substitutions selected from (a) to (c) above are introduced into the amino acid sequence selected from SEQ ID NOs: 86, 87, 90, 92, 46, 95 and 41. In the present invention, the preferred number of substitutions is 1, 2 or 3 substitutions selected from (a) to (c) above.

Furthermore, the peptide of the present invention may be a peptide having CTL-inducing ability, which comprises an amino acid sequence in which, in the amino acid sequence selected from among SEQ ID NOs: 86, 87, 90, 92, 46, 95 and 41, the third amino acid from the N terminus is substituted with aspartic acid or glutamic acid, and/or the C-terminal amino acid is substituted with tyrosine. Preferably, the peptide of the present invention may be a peptide having CTL-inducing ability, which consists of an amino acid sequence in which, in the amino acid sequence selected from among SEQ ID NOs: 86, 87, 90, 92, 46, 95 and 41, the third amino acid from the N terminus is substituted with aspartic acid or glutamic acid, and/or the C-terminal amino acid is substituted with tyrosine. That is, the peptide of the present invention can be a peptide having CTL-inducing ability, which comprises an amino acid sequence in which one or more substitutions selected from (a) and (b) below are introduced into the amino acid sequence selected from among SEQ ID NOs: 86, 87, 90, 92, 46, 95 and 41:
  (a) the third amino acid from the N terminus is substituted with aspartic acid or glutamic acid; and
  (b) the C-terminal amino acid is substituted with tyrosine.

In a preferred embodiment, the peptide of the present invention may be a peptide having CTL-inducing ability, which consists of an amino acid sequence in which one or more substitutions selected from (a) to (b) above are introduced into the amino acid sequence selected from among SEQ ID NOs: 86, 87, 90, 92, 46, 95 and 41.

Substitution(s) may be introduced into amino acid(s) not only at the anchor site(s), but also at a position(s) of potential T cell receptor (TCR) recognition site(s) of the peptides. Several research studies have demonstrated that a peptide that has amino acid substitutions, such as CAP1, $p53_{(264-272)}$, Her-2/neu$_{(369-377)}$ or $gp100_{(209-217)}$, may have equal to or better activity than that of the original peptide (Zaremba et al. Cancer Res. 57, 4570-7, 1997; T. K. Hoffmann et al. J Immunol. (2002) February 1, 168(3): 1338-47.; S. O. Dionne et al. Cancer Immunol immunother. (2003) 52: 199-206; and S. O. Dionne et al. Cancer Immunology, Immunotherapy (2004) 53, 307-14).

The present invention also contemplates that one, two or several amino acids can be added to the N terminus and/or C terminus of the peptides of the present invention (for example, peptides consisting of the amino acid sequence selected from among SEQ ID NOs: 5, 28, 30, 32, 61, 62, 63, 64, 67, 74, 77, 52, 79, 80, 85, 27, 86, 87, 90, 92, 46, 95 and 41). Such modified peptides that retain CTL-inducing ability are also included in the present invention. For example, when a peptide in which one, two or several amino acids are added to the N terminus and/or C terminus of a peptide consisting of the amino acid sequence selected from among SEQ ID NOs: 32, 64, 67, 77, 27 and 86 is contacted with an APC(s), it is incorporated into the APC(s) and processed to become a peptide consisting of the amino acid sequence selected from among SEQ ID NOs: 32, 64, 67, 77, 27 and 86. It can then induce CTLs through presentation on the cell surface of an APC via the antigen presentation pathway. More specifically, peptides of the present invention can be peptides in which one, two or several amino acids are added to either or both of the N terminus and C terminus.

However, when the amino acid sequence of a peptide is identical to a portion of the amino acid sequence of an endogenous or exogenous protein having a different function, side effects such as autoimmune disorders and/or allergic symptoms against specific substances may be induced. Therefore, it is preferable to perform homology searches using available databases to avoid situations in which the amino acid sequence of the peptide matches the amino acid sequence of another protein. When it becomes clear from the homology searches that no peptide exists with as few as 1 or 2 amino acid differences as compared to the objective peptide, the objective peptide can be modified in order to increase its binding affinity with HLA antigens, and/or increase its CTL-inducing ability without danger of such side effects.

Peptides in which one, two or several amino acids of a peptide of the present invention are modified are predicted to be able to retain CTL-inducing ability of the original peptide; however, it is preferable to verify the CTL-inducing ability of the modified peptides. Herein, the "peptide having CTL-inducing ability (CTL inducibility)" refers to a peptide that induces CTLs through APCs stimulated with the peptide. "CTL induction" includes induction of differentiation into CTLs, induction of CTL activation, induction of CTL proliferation, induction of CTL's cytotoxic activity, induction of CTL-mediated dissolution of target cells, and induction of increase of IFN-gamma production of CTLs.

The CTL-inducing ability can be confirmed by inducing and stimulating APCs that retain an HLA antigen (for example, B lymphocytes, macrophages, and dendritic cells) with a peptide, and mixing it with CD8-positive T cells; and then measuring IFN-gamma released by CTLs against the target cells. For the APCs, human peripheral blood mononuclear leukocyte-derived dendritic cells can be preferably used. As a reaction system, transgenic animals generated to express an HLA antigen can be used. Alternatively, for example, the target cells may be radio-labelled with $^{51}Cr$ or such, and the cytotoxic activity of the peptide-induced CTLs may be calculated from the radioactivity emitted from the target cells. Alternatively, in the presence of peptide-stimulated APCs, it is possible to evaluate the CTL-inducing ability by measuring the IFN-gamma produced and released by CTLs, and visualizing the inhibition zone on the media using anti-IFN-gamma monoclonal antibodies.

In addition to the modifications above, the peptides of the present invention can be linked to other peptides as long as the resultant linked peptide retains the CTL-inducing ability. An example of an appropriate peptide to be linked with the peptides of the present invention includes a TAA-derived CTL-inducing peptide. Further, the peptides of the present invention can also be linked with each other. Suitable linkers for use in linking peptides are known in the art, and for example, linkers such as AAY (P. M. Daftarian et al., J Trans Med 2007, 5:26), AAA, NKRK (SEQ ID NO: 111) (R. P. M. Sutmuller et al., J Immunol. 2000, 165: 7308-15), or K (S. Ota et al., Can Res. 62, 1471-6, K. S. Kawamura et al., J Immunol. 2002, 168: 5709-15) can be used. Peptides can be linked in various arrangements (for example, catenulate, repeated, etc.), and one can also link three or more peptides.

The peptides of the present invention can also be linked to other substances as long as the resultant linked peptide retains the CTL-inducing ability. Examples of an appropriate substance to be linked with a peptide of the present invention include, for example, a peptide, a lipid, a sugar or sugar chain, an acetyl group, and a naturally-occurring or synthetic polymer. The peptides of the present invention can be modified by glycosylation, side-chain oxidation, phosphorylation or such, as long as their CTL-inducing ability is not impaired. One can also perform such types of modifications to confer additional functions (for example, targeting function and delivery function) or to stabilize the peptide.

For example, to increase the in vivo stability of a peptide, it is known in the art to introduce D-amino acids, amino acid mimetics or non-naturally occurring amino acids, and this concept may also be applied to peptides of the present invention. Peptide stability can be assayed by several methods. For example, stability can be tested by using a peptidase as well as various biological media such as human plasma and serum (see, e.g., Verhoef et al., Eur J Drug Metab Pharmacokin 1986, 11: 291-302).

Further, as stated above, among the modified peptides in which one, two, or several amino acid residues have been substituted, deleted, inserted and/or added, those having the same or higher activity as compared to original peptides can be screened for or selected. Thus, the present invention also provides methods of screening for or selecting modified peptides that have the same or higher activity than that of the original peptide. Specifically, the present invention provides a method of screening for a peptide having CTL-inducing ability, wherein the method comprises the steps of:

(a) generating candidate sequences consisting of an amino acid sequence in which one, two, or several amino acid residues are substituted, deleted, inserted and/or added to the original amino acid sequence consisting of the amino acid sequence selected from among SEQ ID NOs: 5, 28, 30, 32, 61, 62, 63, 64, 67, 74, 77, 52, 79, 80, 85, 27, 86, 87, 90, 92, 46, 95 and 41;
(b) selecting from among the candidate sequences generated in (a), a candidate sequence that does not have a significant homology (sequence identity) with any known human gene product other than KOC1;
(c) contacting a peptide consisting of the candidate sequence selected in (b) with APCs;
(d) contacting the APCs of (c) with CD8-positive T cells; and
(e) selecting a peptide that has an equal to or higher CTL-inducing ability than that of a peptide consisting of the original amino acid sequence.

Herein, the peptide of the present invention is also described as a "KOC1 peptide(s)" or a "KOC1 polypeptide(s)".

III. Preparation of Peptides of the Present Invention

Well known techniques can be used to prepare peptides of the present invention. For example, recombinant DNA technology or chemical synthesis can be used to prepare peptides of the present invention. Peptides of the present invention can be synthesized individually, or as longer polypeptides including two or more peptides. Peptides of the present invention can be isolated from host cells or synthesis reaction products after they are produced in the host cells using recombinant DNA technology or after they are chemically synthesized. That is, peptides of the present invention can be purified or isolated so as not to substantially contain other host-cell proteins and fragments thereof, or any other chemical substances.

The peptides of the present invention may contain modifications, such as glycosylation, side chain oxidation, or phosphorylation provided such modifications do not destroy the biological activity of the original peptide. Other illustrative modifications include incorporation of D-amino acids or other amino acid mimetics that may be used, for example, to increase the serum half life of the peptides.

A peptide of the present invention can be obtained through chemical synthesis based on the selected amino acid sequence. Examples of conventional peptide synthesis methods that can be adapted to the synthesis include the methods described in the documents below:

(i) Peptide Synthesis, Interscience, New York, 1966;
(ii) The Proteins, Vol. 2, Academic Press, New York, 1976;
(iii) "Peptide Synthesis" (in Japanese), Maruzen Co., 1975;
(iv) "Basics and Experiment of Peptide Synthesis" (in Japanese), Maruzen Co., 1985;
(v) "Development of Pharmaceuticals" (in Japanese), Continued Vol. 14 (peptide synthesis), Hirokawa, 1991;
(vi) WO99/67288; and
(vii) Barany G. & Merrifield R. B., Peptides Vol. 2, Solid Phase Peptide Synthesis, Academic Press, New York, 1980, 100-118.

Alternatively, the peptides of the present invention can be obtained adapting any known genetic engineering methods for producing peptides (e.g., Morrison J, J Bacteriology 1977, 132: 349-51; Clark-Curtiss & Curtiss, Methods in Enzymology (Wu et al.) 1983, 101: 347-62). For example, first, a suitable vector harboring a polynucleotide encoding the peptide of the present invention in an expressible form (e.g., downstream of a regulatory sequence corresponding to a promoter sequence) is prepared and transformed into a suitable host cell. The host cell is then cultured to produce the peptide of the present invention. The peptide of the present invention can also be produced in vitro using an in vitro translation system.

IV. Polynucleotides

The present invention also provides a polynucleotide which encodes any of the peptides of the present invention. These include polynucleotides derived from the naturally occurring KOC1 gene (e.g., GenBank Accession No. NM_006547 (SEQ ID NO: 109)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described above without altering the encoded polypeptide. Such nucleic acid variations are "silent variations", which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (e.g., plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer RP, Tetrahedron 1992, 48: 2223-311; Matthes et al., EMBO J 1984, 3: 801-5.

V. Exosomes

The present invention further provides intracellular vesicles, referred to as exosomes, that present complexes formed between the peptides of the present invention and HLA antigens on their surface. Exosomes can be prepared, for example, using the methods detailed in JPH11-510507 and WO99/03499, and can be prepared using APCs obtained from patients who are subject to treatment and/or prevention (prophylaxis). The exosomes of the present invention can be inoculated as vaccines, in a fashion similar to the peptides of the present invention.

The type of the HLA antigens included in the above-described complexes must match that of the subject in need of treatment and/or prevention (prophylaxis). For example, in Asian populations, HLA-A11 (for example, HLA-A*1101) and HLA-A33 (for example, HLA-A*3303) are alleles widely and generally seen in Asian populations, and these HLA antigen types are considered to be suitable for treatment in Asian patients. Further, HLA-A03 (for example, HLA-A*0301) and HLA-A01 (for example, HLA-A*0101) are alleles widely and generally seen in Caucasian populations, and these HLA antigen types are considered to be suitable for treatment in Caucasian patients. Typically in clinical practice, it is possible to select an appropriate peptide that has a high level of binding affinity for a specific HLA antigen or that has CTL-inducing ability by antigen presentation mediated by a specific HLA antigen, by studying in advance the HLA antigen type of the patient in need of treatment.

The exosomes of the present invention present on their surface a complex of a peptide of the present invention and HLA-A11, HLA-A33, HLA-A03 or HLA-A01. When the HLA that forms a complex with a peptide of the present invention is HLA-A11, the peptide of the present invention is preferably a peptide having the amino acid sequence selected from among SEQ ID NOs: 5, 28, 30 and 32 or a modified peptide thereof, and more preferably a peptide consisting of the amino acid sequence selected from among SEQ ID NOs: 5, 28, 30 and 32 or a modified peptide thereof. Further, when the HLA that forms a complex with a peptide of the present invention is HLA-A33, the peptide of the present invention is preferably a peptide having the amino acid sequence selected from among SEQ ID NOs: 61, 62, 63, 64, 67, 74, 77, 52, 79, 80 and 85 or a modified peptide thereof, and more preferably a peptide consisting of the amino acid sequence selected from among SEQ ID NOs: 61, 62, 63, 64, 67, 74, 77, 52, 79, 80 and 85 or a modified peptide thereof. Further, when the HLA that forms a complex with a peptide of the present invention is HLA-A03, the peptide of the present invention is preferably a peptide having the amino acid sequence selected from among SEQ ID NOs: 27, 30 and 52 or a modified peptide thereof, and more preferably a peptide consisting of the amino acid sequence selected from among SEQ ID NOs: 27, 30 and 52 or a modified peptide thereof. Further, when the HLA that forms a complex with a peptide of the present invention is HLA-A01, the peptide of the present invention is preferably a peptide having the amino acid sequence selected from among SEQ ID NOs: 86, 87, 90, 92, 46, 95 and 41 or a modified peptide thereof, and more preferably a peptide consisting of the amino acid sequence selected from among SEQ ID NOs: 86, 87, 90, 92, 46, 95 and 41 or a modified peptide thereof.

VI. Antigen-Presenting Cells (APCs)

The present invention further provides APCs that present on their surface complexes formed between HLA antigens and peptides of the present invention. Alternatively, the present invention provides APCs having on their cell surface complexes formed between HLA antigens and peptides of the present invention. The APCs of the present invention can be isolated APCs. When used in the context of cells (APCs, CTLs, etc.), the term "isolated" means that the cells are separated from another type of cells. The APCs of the present invention may be APCs induced from APCs derived from the patient to be subjected to treatment and/or prevention (prophylaxis), and can be administered as a vaccine by themselves or in combination with other drugs including a peptide(s), an exosome(s) or a CTL(s) of the present invention.

The APCs of the present invention are not limited to specific types of cells, and include cells known to present proteinaceous antigens on their cell surface so as to be recognized by lymphocytes, for example, dendritic cells (DCs), Langerhans cells, macrophages, B cells, and activated T cells. Since DC is a representative APC that has the strongest CTL-inducing activity among APCs, DCs can be preferably used as the APCs of the present invention. In the present invention, the preferable DC is an isolated DC derived from human. Further, it is not necessary for the APCs of the present invention to be homogeneous, and they can be mixtures of multiple types of cells having an antigen-presenting function and can be mixtures of APCs each of which presents different types of the peptides of the present invention.

For example, APCs of the present invention can be obtained by isolating DCs from peripheral blood mononuclear cells and then stimulating them in vitro with the peptides of the present invention. When the peptide of the present invention is administered to a subject, APCs presenting the peptide of the present invention are induced in the body of the subject. Therefore, after the peptides of the present invention are administered to a subject, the APCs of the present invention can be obtained by collecting APCs from the subject. Alternatively, the APCs of the present invention can be obtained by contacting APCs collected from a subject with a peptide of the present invention.

In order to induce an immune response against KOC1-expressing cancer cells in a subject, the APCs of the present invention can be administered to the subject by themselves or in combination with other drugs including peptide(s), exosome(s) or CTL(s) of the present invention. For example, the ex vivo administration can comprise the following steps of:
(a) collecting APCs from a first subject;
(b) contacting the APCs of step (a) with a peptide; and
(c) administering the APCs of step (b) to a second subject.

The first subject and the second subject may be the same individual, or may be different individuals. When the first subject and the second subject are different individuals, it is preferable that the HLAs of the first subject and the second subject are of the same type. The APC obtained in step (b) above can be a vaccine for cancer treatment and/or prevention (prophylaxis).

The APCs of the present invention obtained by a method such as described above have CTL-inducing ability. The term "CTL-inducing ability (CTL inducibility)" used in the context of an APC(s) refers to the ability of the APC to be able to induce a CTL(s) when placed in contact with a CD8-positive T cell(s). Further, the "CTL-inducing ability (CTL inducibility)" includes the ability of an APC to induce CTL activation, the ability of an APC to induce CTL proliferation, the ability of an APC to facilitate CTL-mediated dissolution of target cells, and the ability of an APC to increase CTL-mediated IFN-gamma production. The CTL(s) induced by the APC of the present invention is a CTL(s) specific to KOC1 and demonstrates a specific cytotoxic activity against KOC1-expressing cells.

In addition to the above-described methods, the APCs of the present invention can be prepared by introducing a polynucleotide encoding a peptide of the present invention into APCs in vitro. The polynucleotide to be introduced can be in the form of DNA or RNA. The method of introduction is not particularly limited, and examples thereof include various methods conventionally performed in the art such as lipofection, electroporation and the calcium phosphate method. More specifically, methods described in Cancer Res 1996, 56: 5672-7; J Immunol 1998, 161: 5607-13; J Exp Med 1996, 184: 465-72, and JP2000-509281 can be used. By introducing a polynucleotide encoding a peptide of the present invention into an APC, the polynucleotide is transcribed and translated in the cell, and then the produced peptide is processed by MHC Class I and proceeds through a presentation pathway to present the peptide of the present invention on the cell surface of the APC.

In a preferred embodiment, the APC of the present invention presents on its cell surface a complex formed between a peptide of the present invention and HLA-A11 (more preferably HLA-A*1101), HLA-A33 (more preferably HLA-A*3303), HLA-A03 (more preferably HLA-A*0301) or HLA-A01 (more preferably HLA-A*0101). When the HLA that forms a complex with a peptide of the present invention is HLA-A11, the peptide of the present invention is preferably a peptide having the amino acid sequence selected from among SEQ ID NOs: 5, 28, 30 and 32 or a modified peptide thereof, and more preferably a peptide consisting of the amino acid sequence selected from among SEQ ID NOs: 5, 28, 30 and 32. When the HLA that forms a complex with a peptide of the present invention is HLA-A33, the peptide of the present invention is preferably a peptide having the amino acid sequence selected from among SEQ ID NOs: 61, 62, 63, 64, 67, 74, 77, 52, 79, 80 and 85 or a modified peptide thereof, and more preferably a peptide consisting of the amino acid sequence selected from among SEQ ID NOs: 61, 62, 63, 64, 67, 74, 77, 52, 79, 80 and 85. When the HLA that forms a complex with a peptide of the present invention is HLA-A03, the peptide of the present invention is preferably a peptide having the amino acid sequence selected from among SEQ ID NOs: 27, 30 and 52 or a modified peptide thereof, and more preferably a peptide consisting of the amino acid sequence selected from among SEQ ID NOs: 27, 30 and 52. When the HLA that forms a complex with a peptide of the present invention is HLA-A01, the peptide of the present invention is preferably a peptide having the amino acid sequence selected from among SEQ ID NOs: 86, 87, 90, 92, 46, 95 and 41 or a modified peptide thereof, and more preferably a peptide consisting of the amino acid sequence selected from among SEQ ID NOs: 86, 87, 90, 92, 46, 95 and 41.

The APC(s) of the present invention is preferably an APC(s) induced by a method comprising a step described (a) or (b) below:

(a) contacting an APC(s) expressing at least one HLA selected from among HLA-A11 (more preferably HLA-A*1101), HLA-A33 (more preferably HLA-A*3303), HLA-A03 (more preferably HLA-A*0301) and HLA-A01 (more preferably HLA-A*0101) with a peptide of the present invention; or
(b) introducing a polynucleotide encoding a peptide of the present invention into an APC(s) expressing at least one HLA selected from among HLA-A11 (more preferably HLA-A*1101), HLA-A33 (more preferably HLA-A*3303), HLA-A03 (more preferably HLA-A*0301) and HLA-A01 (more preferably HLA-A*0101).

The peptide of the present invention to be contacted with the HLA-A11-expressing APC(s) is preferably a peptide having the amino acid sequence selected from among SEQ ID NOs: 5, 28, 30 and 32 or a modified peptide thereof, and more preferably a peptide consisting of the amino acid sequence selected from among SEQ ID NOs: 5, 28, 30 and 32.

The peptide of the present invention to be contacted with the HLA-A33-expressing APC(s) is preferably a peptide having the amino sequence selected from among SEQ ID NOs: 61, 62, 63, 64, 67, 74, 77, 52, 79, 80 and 85 or a modified peptide thereof, and more preferably a peptide consisting of the amino sequence selected from among SEQ ID NOs: 61, 62, 63, 64, 67, 74, 77, 52, 79, 80 and 85.

The peptide of the present invention to be contacted with the HLA-A03-expressing APC(s) is preferably a peptide having the amino acid sequence selected from among SEQ ID NOs: 27, 30 and 52 or a modified peptide thereof, and more preferably a peptide consisting of the amino acid sequence selected from among SEQ ID NOs: 27, 30 and 52.

The peptide of the present invention to be contacted with the HLA-A01-expressing APC(s) is preferably a peptide having the amino acid sequence selected from among SEQ ID NOs: 86, 87, 90, 92, 46, 95 and 41 or a modified peptide thereof, and more preferably a peptide consisting of the amino acid sequence selected from among SEQ ID NOs: 86, 87, 90, 92, 46, 95 and 41.

The present invention provides use of a peptide of the present invention for the manufacture of a pharmaceutical composition that induces an APC(s) having CTL-inducing ability. In addition, the present invention provides a method or process of manufacturing a pharmaceutical composition that induces an APC(s) having CTL-inducing ability. Further, the present invention provides a peptide of the present invention for inducing an APC(s) having CTL-inducing ability.

VII. Cytotoxic T Lymphocytes (CTLs)

The CTL induced by a peptide of the present invention can be used as a vaccine in a similar manner to the peptide of the present invention for enhancing an immune response targeting KOC1-expressing cell in vivo. Thus, the present invention provides CTLs that are induced or activated by a peptide of the present invention. The CTLs of the present invention are CTLs that target a peptide of the present invention, and are capable of binding to a complex of a peptide of the present invention and an HLA antigen. Binding of a CTL to the complex is mediated via a T cell receptor (TCR) present on the cell surface of the CTL. The CTLs of the present invention can be isolated CTLs. The preferable CTLs are isolated CTLs of human origin. The CTLs of the present invention do not have to be homogeneous, and can be mixtures of CTLs each of which targets different types of peptides of the present invention.

The CTLs of the present invention can be obtained by (1) administering a peptide of the present invention to a subject, (2) stimulating APCs and CD8-positive T cells, or peripheral blood mononuclear cells (PBMCs) derived from a subject with a peptide of the present invention in vitro, (3) contacting in vitro CD8-positive T cells or PBMCs with APCs or exosomes that present on their surface a complex of an HLA antigen and a peptide of the present invention, or (4) introducing into CD8-positive T cells a vector comprising a polynucleotide encoding each subunit of a T cell receptor (TCR) capable of binding to a peptide of the present invention presented on cell surface via an HLA antigen. The exosomes and APCs used in the method of (2) or (3) above can be prepared by methods described in the "V. Exosomes" and "VI. Antigen-presenting cells (APCs)" sections, respectively, and the details of the method of (4) above will be described in the "VIII. T cell receptor (TCR)" section.

The CTLs of the present invention can be administered by themselves to patients who are subject to treatment and/or prevention (prophylaxis), or in combination with other drugs including peptide(s), APC(s) or exosome(s) of the present invention for the purpose of regulating effects. Further, the CTLs of the present invention can be CTLs induced from CD8-positive T cells derived from the patients who are subject to administration of the CTLs. The CTLs of the present invention act specifically on target cells that present the peptides of the present invention, for example, the same peptides used to induce the CTLs of the present invention. The target cells may be cells that endogenously express KOC1, such as cancer cells, or cells transfected with the KOC1 gene. Cells that present a peptide of the present invention on their cell surface due to stimulation by the peptide can become a target of attack by the CTLs of the present invention. The cells targeted by the CTLs of the present invention are preferably cells that are positive for at least one of HLA-A11 (more preferably HLA-A*1101), HLA-A33 (more preferably HLA-A*3303), HLA-A03 (more preferably HLA-A*0301), and HLA-A01 (more preferably HLA-A*0101).

In a preferred embodiment, the CTLs of the present invention target specifically cells that express both KOC1 and at least one HLA selected from among HLA-A11 (more preferably HLA-A*1101), HLA-A33 (more preferably HLA-A*3303), HLA-A03 (more preferably HLA-A*0301), and HLA-A01 (more preferably HLA-A*0101). In the present invention, the cells targeted by the CTLs can be cells that have any of the alleles of HLA-A11, HLA-A33, HLA-A03, and HLA-A01 homozygously or heterozygously.

Herein, that the CTL "targets" cells refers to CTL recognition of cells that present on their cell surface a complex of HLA and a peptide of the present invention and demonstration of a cytotoxic activity against the cells. Further, "specifically target" refers to that the CTLs demonstrate a cytotoxic activity against those cells, but do not show a damaging activity to other cells. The expression "recognize cells" used in the context of CTLs refers to binding to a complex of HLA and a peptide of the present invention presented on cell surface via its TCR, and demonstrating a specific cytotoxic activity against the cell. Therefore, the CTLs of the present invention are preferably CTLs that can bind via TCR to a complex formed between a peptide of the present invention and HLA-A11 (more preferably HLA-A*1101), HLA-A33 (more preferably HLA-A*3303), HLA-A03 (more preferably HLA-A*0301) or HLA-A01 (more preferably HLA-A*0101) presented on cell surface.

Furthermore, the CTLs of the present invention are preferably CTLs induced by a method comprising a step described in (a) or (b) below:
(a) contacting in vitro CD8-positive T cells with APCs or exosomes that present on their surface a complex of a peptide of the present invention and HLA-A11 (more preferably HLA-A*1101), HLA-A33 (more preferably HLA-A*3303), HLA-A03 (more preferably HLA-A*0301) or HLA-A01 (more preferably HLA-A*0101); or
(b) introducing into CD8-positive T cells a polynucleotide encoding each subunit of a TCR capable of binding to a peptide of the present invention presented on cell surface by HLA-A11 (more preferably 14LA-A*1101), HLA-A33 (more preferably HLA-A*3303), HLA-A03 (more preferably HLA-A*0301) or HLA-A01 (more preferably HLA-A*0101).

VIII. T Cell Receptors (TCRs)

The present invention also provides compositions comprising a polynucleotide encoding each subunit of a TCR capable of binding to a peptide of the present invention presented on cell surface by an HLA antigen, and methods of using the same. The polynucleotide confers CD8-positive T cells with specificity against KOC1-expressing cancer cells through expression of a TCR capable of binding to a peptide of the present invention presented on cell surface by an HLA antigen. Polynucleotides encoding an alpha chain(s) and a beta chain(s) can be identified as the TCR subunit of the CTL induced by a peptide of the present invention by using known methods in the art (WO2007/032255 and Morgan et al., J Immunol, 171, 3288 (2003)). For example, PCR methods are preferred for TCR analysis. Without being limited thereto, PCR primers for analysis may be, for example, a primer set(s) for amplification by combining the 5' side primer and the 3' side primer(s) below:

```
5' side primer:
5'-R Primer
                                          (SEQ ID NO: 105)
(5'-gtctaccaggcattcgcttcat-3')

3' side primers:
TCR-alpha-chain C-region-specific
3-TRa-C Primer
                                          (SEQ ID NO: 106)
(5'-tcagctggaccacagccgcagcgt-3')

TCR-beta-chain C1-region-specific
3-TRb-C1 Primer
                                          (SEQ ID NO: 107)
(5'-tcagaaatcctttctcttgac-3')
or TCR-beta-chain C2-region-specific
3-TR-beta-C2 Primer
                                          (SEQ ID NO: 108)
(5'-ctagcctctggaatcctttctctt-3')
```

The TCRs formed by introducing the identified polynucleotides into CD8-positive T cells can bind with high binding affinity to the target cells that present a peptide of the present invention, and mediates efficient killing of the target cells presenting a peptide of the present invention in vivo and in vitro.

A polynucleotide encoding each TCR subunit can be incorporated into an appropriate vector, for example, retrovirus vector. These vectors are well known in the art. The polynucleotide or a vector comprising thereof in an expressible form can be introduced into a CD8-positive T cell, for example, a CD8-positive T cell derived from a patient. The present invention provides off-the-shelf compositions that allow rapid and easy production of modified T cells that have superior cancer cell-killing properties by rapid modification of the patient's own T cells (or T cells derived from another subject).

Herein, a specific TCR is a TCR that can confer a specific cytotoxic activity against target cells by specifically recognizing a complex of a peptide of the present invention and an HLA antigen presented on the surface of the target cell when the TCR is present on the surface of a CD8-positive T cell. Specific recognition of the above-described complex can be confirmed by any known method, and preferable examples thereof include HLA multimer staining analysis using HLA molecules and peptides of the present invention and ELISPOT assay methods. Specific TCR-mediated recognition of target cell by T cell introduced with the above-described polynucleotide and signal transduction in the cell can be confirmed by carrying out an ELISPOT assay. When the above-described TCR is present on the surface of a CD8-positive T cell, whether the TCR can confer a target cell-specific cytotoxic activity against the CD8-positive T cell can also be confirmed by known methods. Preferable methods include, for example, measuring the cytotoxic activity against target cells by a chrome release assay method or such.

The present invention provides, in the context of HLA-A11, CTLs prepared by transforming CD8-positive T cells with a polynucleotide encoding each subunit of TCR that binds to, for example, a peptide having the amino acid sequence selected from among SEQ ID NOs: 5, 28, 30 and 32.

The present invention provides, in the context of HLA-A33, CTLs prepared by transforming CD8-positive T cells with a polynucleotide encoding each subunit of TCR that binds to, for example, a peptide having the amino acid sequence selected from among SEQ ID NOs: 61, 62, 63, 64, 67, 74, 77, 52, 79, 80 and 85.

The present invention provides, in the context of HLA-A03, CTLs prepared by transforming CD8-positive T cells with a polynucleotide encoding each subunit of TCR that binds to, for example, a peptide having the amino acid sequence selected from among SEQ ID NOs: 27, 30 and 52.

The present invention provides, in the context of HLA-A01, CTLs prepared by transforming CD8-positive T cells with a polynucleotide encoding each subunit of TCR that binds to, for example, a peptide having the amino acid sequence selected from among SEQ ID NOs: 86, 87, 90, 92, 46, 95 and 41.

The transformed CTLs are capable of homing in vivo and may be propagated by a well-known in vitro culturing method (for example, Kawakami et al., J Immunol., 142, 3452-61 (1989)). The CTLs of the present invention can be used to form an immunogenic composition useful for disease treatment or prevention (prophylaxis) in a patient in need of treatment or prevention (prophylaxis) (the contents are incorporated herein for reference WO2006/031221).

IX. Pharmaceutical Compositions

The present invention further provides compositions or pharmaceutical compositions, comprising at least one active ingredient selected from below:
(a) a peptide of the present invention;
(b) a polynucleotide encoding a peptide of the present invention in an expressible form;

(c) an APC of the present invention;
(d) an exosome of the present invention; and
(e) a CTL of the present invention.

The pharmaceutical compositions of the present invention can comprise as needed a carrier(s), an excipient(s) or such commonly used in pharmaceuticals without particular limitations, in addition to the active ingredient(s) described above. An example of a carrier that can be used in a pharmaceutical composition of the present invention includes sterilized water, physiological saline, phosphate buffer, culture fluid and such. Therefore, the present invention also provides pharmaceutical compositions, comprising at least one active ingredient selected from (a) to (e) below and a pharmaceutically acceptable carrier:

(a) a peptide of the present invention;
(b) a polynucleotide encoding a peptide of the present invention in an expressible form;
(c) an APC of the present invention;
(d) an exosome of the present invention; and
(e) a CTL of the present invention.

Further, the pharmaceutical compositions of the present invention can comprise, as needed, stabilizers, suspensions, preservatives, surfactants, solubilizing agents, pH adjusters, aggregation inhibitors and such.

The KOC1 expression significantly up-regulates in cancer cells compared with normal tissues. Thus, a peptide of the present invention or a polynucleotide encoding the peptide can be used to treat and/or prevent cancer, and/or prevent postoperative recurrence thereof. Therefore, the present invention provides pharmaceutical compositions for treating and/or preventing cancer, and/or preventing postoperative recurrence thereof, comprising one or more types of peptides or polynucleotides of the present invention as an active ingredient. Alternatively, the peptides of the present invention can be made to be presented on the surface of exosomes or APCs for use as pharmaceutical compositions. In addition, CTLs of the present invention targeting any one of the peptides of the present invention can also be used as an active ingredient of the pharmaceutical compositions of the present invention. The pharmaceutical compositions of the present invention may comprise a therapeutically effective amount or a pharmaceutically effective amount of the above-described active ingredient.

The pharmaceutical compositions of the present invention may also be used as a vaccine. In the context of the present invention, the term "vaccine" (also called "immunogenic composition") refers to a composition that has a function of inducing an immune response that leads to antitumor action when inoculated into an animal. Thus, a pharmaceutical composition of the present invention can be used to induce an immune response that leads to antitumor action. The immune response induced by a peptide, a polynucleotide, an APC, a CTL and a pharmaceutical composition of the present invention is not particularly limited as long as it is an immune response that leads to antitumor action, and examples include induction of cancer cell-specific CTLs and induction of cancer cell-specific cytotoxic activity.

The pharmaceutical compositions of the present invention can be used to treat and/or prevent cancer, and/or prevent postoperative recurrence thereof in human subjects or patients. The pharmaceutical compositions of the present invention can be used preferably to a subject positive for at least one HLA selected from among HLA-A11, HLA-A33, HLA-A03 and HLA-A01. Further, the pharmaceutical compositions of the present invention can be used preferably to treat and/or prevent cancers expressing KOC1 and at least one HLA selected from among HLA-A11, HLA-A33, HLA-A03 and HLA-A01, and/or prevent postoperative recurrence thereof.

In another embodiment, the present invention provides use of an active ingredient selected from below in the manufacture of a pharmaceutical composition for treating or preventing cancer:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

Alternatively, the present invention further provides an active ingredient selected from below for use in treating or preventing cancer:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

Alternatively, the present invention further provides a method or process for manufacturing a pharmaceutical composition for treating or preventing cancer, wherein the method or process comprises a step of formulating at least one active ingredient selected from below with a pharmaceutically or physiologically acceptable carrier:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In another embodiment, the present invention further provides a method or process for manufacturing a pharmaceutical composition for treating or preventing cancer, wherein the method or process comprises a step of mixing an active ingredient selected from below with a pharmaceutically or physiologically acceptable carrier:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In another embodiment, the present invention further provides a method for treating or preventing cancer, which comprises a step of administering to a subject at least one active ingredient selected from below:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In the present invention, peptides having the amino acid sequence selected from among SEQ ID NOs: 5, 28, 30 and 32 are identified as HLA-A11-restricted epitope peptides that can induce a potent and specific immune response. Therefore, pharmaceutical compositions of the present invention comprising at least one peptide having the amino acid sequence selected from among SEQ ID NOs: 5, 28, 30 and 32 are suitable particularly for administration to a subject having HLA-A11 (for example, HLA-A*1101) as an HLA antigen. The same applies to pharmaceutical compositions comprising a polynucleotide encoding any of these peptides (i.e., polynucleotides of the present invention), an APC or exosome that presents these peptides (i.e., APCs or exosomes of the present invention), or a CTL targeting these peptides (i.e., CTLs of the present invention). That is, pharmaceutical compositions comprising an active ingredient in association with a peptide having the amino acid sequence selected from among SEQ ID NOs: 5, 28, 30 and 32 are suitable for administration to subjects having HLA-A11 (i.e., HLA-A11-positive subjects). In a more preferred embodiment, the pharmaceutical composition of the present invention is a pharmaceutical composition that comprises a peptide having the amino acid sequence of SEQ ID NO: 32.

Similarly, in the present invention, peptides having the amino acid sequence selected from among SEQ ID NOs: 61, 62, 63, 64, 67, 74, 77, 52, 79, 80 and 85 are identified as HLA-A33-restricted epitope peptides that can induce a potent and specific immune response. Therefore, pharmaceutical compositions of the present invention comprising at least one peptide having the amino acid sequence selected from among SEQ ID NOs: 61, 62, 63, 64, 67, 74, 77, 52, 79, 80 and 85 are suitable particularly for administration to a subject having HLA-A33 (for example, HLA-A*3303) as an HLA antigen. The same applies to pharmaceutical compositions comprising a polynucleotide encoding any of these peptides (i.e., polynucleotides of the present invention), an APC or exosome that presents these peptides (i.e., APCs or exosomes of the present invention), or a CTL targeting these peptides (i.e., CTLs of the present invention). That is, pharmaceutical compositions comprising an active ingredient in association with a peptide having the amino acid sequence selected from among SEQ ID NOs: 61, 62, 63, 64, 67, 74, 77, 52, 79, 80 and 85 are suitable for administration to subjects having HLA-A33 (i.e., HLA-A33-positive subjects). In a more preferred embodiment, the pharmaceutical composition of the present invention is a pharmaceutical composition that comprises at least one peptide having the amino acid sequence selected from among SEQ ID NOs: 64, 67, and 77.

Similarly, in the present invention, peptides having the amino acid sequence selected from among SEQ ID NOs: 27, 30 and 52 are identified as HLA-A03-restricted epitope peptides that can induce a potent and specific immune response. Therefore, pharmaceutical compositions of the present invention comprising at least one peptide having the amino acid sequence selected from among SEQ ID NOs: 27, 30 and 52 are suitable particularly for administration to a subject having HLA-A03 (for example, HLA-A*0301) as an HLA antigen. The same applies to pharmaceutical compositions comprising a polynucleotide encoding any of these peptides (i.e., polynucleotides of the present invention), an APC or exosome that presents these peptides (i.e., APCs or exosomes of the present invention), or a CTL targeting these peptides (i.e., CTLs of the present invention). That is, pharmaceutical compositions comprising an active ingredient in association with a peptide having the amino acid sequence selected from among SEQ ID NOs: 27, 30 and 52 are suitable for administration to subjects having HLA-A03 (i.e., HLA-A03-positive subjects). In a more preferred embodiment, the pharmaceutical composition of the present invention is a pharmaceutical composition that comprises a peptide having the amino acid sequence of SEQ ID NO: 27.

Similarly, in the present invention, peptides having the amino acid sequence selected from among SEQ ID NOs: 86, 87, 90, 92, 46, 95 and 41 are identified as HLA-A01-restricted epitope peptides that can induce a potent and specific immune response. Therefore, pharmaceutical compositions of the present invention comprising at least one peptide having the amino acid sequence selected from among SEQ ID NOs: 86, 87, 90, 92, 46, 95 and 41 are suitable particularly for administration to a subject having HLA-A01 (for example, HLA-A*0101) as an HLA antigen. The same applies to pharmaceutical compositions comprising a polynucleotide encoding any of these peptides (i.e., polynucleotides of the present invention), an APC or exosome that presents these peptides (i.e., APCs or exosomes of the present invention), or a CTL targeting these peptides (i.e., CTLs of the present invention). That is, pharmaceutical compositions comprising an active ingredient in association with a peptide having the amino acid sequence selected from among SEQ ID NOs: 86, 87, 90, 92, 46, 95 and 41 are suitable for administration to subjects having HLA-A01 (i.e., HLA-A01-positive subjects). In a more preferred embodiment, the pharmaceutical composition of the present invention is a pharmaceutical composition that comprises a peptide having the amino acid sequence of SEQ ID NO: 86.

Cancers to be treated and/or prevented by pharmaceutical compositions of the present invention are not particularly limited as long as they are cancers that express KOC1, and include bladder cancer, cervical cancer, cholangiocellular cancer, chronic myeloid leukemia (CML), colon cancer, rectum cancer, esophagus cancer, diffuse gastric cancer, non-small-cell lung cancer, small-cell lung cancer, lymphoma, osteosarcoma, ovarian cancer, kidney cancer, head and neck cancer, soft tissue tumor, testis cancer and such. It is preferable to use the pharmaceutical composition of the present invention in subjects that homozygously or heterozygously have an HLA allele selected from among HLA-A11, HLA-A33, HLA-A03 and HLA-A01.

In addition to the active ingredients described above, the pharmaceutical compositions of the present invention can comprise the other peptides that have the ability to induce CTLs against cancer cells (for example, the other TAA-derived CTL-inducing peptides), the other polynucleotides encoding the other peptides, the other cells that present the other peptides, or such.

The pharmaceutical compositions of the present invention may also optionally comprise the other therapeutic substances as an active ingredient, as long as they do not inhibit the anti-tumor effects of the above-described active ingredients such as peptides of the present invention. For example, the pharmaceutical compositions of the present invention may optionally comprise anti-inflammatory compositions, analgesics, chemotherapeutics and the like. In addition to including the other therapeutic substances to a pharmaceutical composition of the present invention itself, one can also administer the pharmaceutical composition of the present invention sequentially or concurrently with one or more other pharmaceutical compositions. The dose of the pharmaceutical composition of the present invention and the other pharmaceutical compositions depend on, for example, the type of pharmaceutical composition used and the disease being treated, as well as the scheduling and routes of administration.

It should be understood that in consideration of the formulation type, the pharmaceutical composition of the present invention may include other components conventional in the art, in addition to the ingredients specifically mentioned herein.

The present invention also provides articles of manufacture or kits that comprise a pharmaceutical composition of the present invention. The articles of manufacture or kits of the present invention can include a container that houses the pharmaceutical composition of the present invention. An example of an appropriate container includes a bottle, a vial or a test tube, but is not limited thereto. The container may be formed of various materials such as glass or plastic. A label may be attached to the container, and the disease or disease state to which the pharmaceutical composition of the present invention should be used may be described in the label. The label may also indicate directions for administration and such.

The articles of manufacture or kits of the present invention may further comprise a second container that houses pharmaceutically acceptable diluents optionally, in addition to the container that houses the pharmaceutical composition of the present invention. The articles of manufacture or kits of the present invention may further comprise the other materials desirable from a commercial standpoint and the user's perspective, such as the other buffers, diluents, filters, injection needles, syringes, package inserts with instructions for use.

As needed, the pharmaceutical composition of the present invention can be provided in a pack or dispenser device that can contain one or more units of dosage forms containing active ingredients. The pack can include, for example, a metallic foil or a plastic foil such as a blister pack. Instructions for administration can be attached to the pack or dispenser device.

(1) Pharmaceutical Compositions Comprising Peptide(s) as an Active Ingredient

The pharmaceutical composition comprising a peptide of the present invention can be formulated by conventional formulation methods as needed. The pharmaceutical compositions of the present invention may comprise as needed in addition to the peptide of the present invention, carriers, excipients and such commonly used in pharmaceuticals without particular limitations. Examples of carriers that can be used in pharmaceutical compositions of the present invention include sterilized water (for example, water for injection), physiological saline, phosphate buffer, phosphate buffered saline, Tris buffered saline, 0.3% glycine, culture fluid, and such. Further, the pharmaceutical compositions of the present invention may comprise as needed stabilizers, suspensions, preservatives, surfactants, solubilizing agents, pH adjusters, aggregation inhibitors, and such. The pharmaceutical compositions of the present invention can induce specific immunity against KOC1-expressing cancer cells, and thus can be applied for the purpose of cancer treatment or prevention (prophylaxis).

For example, the pharmaceutical compositions of the present invention can be prepared by dissolving in pharmaceutically or physiologically acceptable water-soluble carriers such as sterilized water (for example, water for injection), physiological saline, phosphate buffer, phosphate buffered saline, and Tris buffered saline and adding, as needed, stabilizers, suspensions, preservatives, surfactants, solubilizing agents, pH adjusters, aggregation inhibitors and such, and then sterilizing the peptide solution. The method of sterilizing a peptide solution is not particularly limited, and is preferably carried out by filtration sterilization. Filtration sterilization can be performed using, for example, a filtration sterilization filter of 0.22 micro-m or less in pore diameter. The filtration-sterilized peptide solution can be administered to a subject, for example, as an injection, without being limited thereto. The pharmaceutical compositions of the present invention may be prepared as a freeze-dried formulation by freeze-drying the above-described peptide solution. The freeze-dried formulation can be prepared by filling the peptide solution prepared as described above into an appropriate container such as an ampule, a vial or a plastic container, followed by freeze drying and encapsulation into the container with a wash-sterilized rubber plug or such after pressure recovery. The freeze-dried formulation can be administered to a subject after it is re-dissolved in pharmaceutically or physiologically acceptable water-soluble carriers such as sterilized water (for example, water for injection), physiological saline, phosphate buffer, phosphate buffered saline, Tris buffered saline and such before administration. Preferred examples of pharmaceutical compositions of the present invention include injections of such a filtration-sterilized peptide solution, and freeze-dried formulations that result from freeze-drying the peptide solution. The present invention further encompasses kits comprising such a freeze-dried formulation and re-dissolving solution. The present invention also encompasses kits comprising a container that houses the freeze-dried formulation, which is a pharmaceutical composition of the present invention, and a container that houses a re-dissolving solution thereof.

The pharmaceutical compositions of the present invention can comprise a combination of two or more types of the peptides of the present invention. The combination of peptides can take a cocktail form of mixed peptides, or can be conjugated with each other using standard techniques. For example, peptides can be chemically linked or expressed as single fusion polypeptide sequences. By administering a peptide of the present invention, the peptide is presented on APCs by an HLA antigen at a high density, and then subsequently CTLs that react specifically to a complex formed between the presented peptide and the HLA antigen are induced. Alternatively, APCs (for example, DCs) are removed from a subject, and subsequently stimulated with peptides of the present invention to obtain APCs that present any of the peptides of the present invention on their cell surface. These APCs are re-administered to a subject to induce CTLs in the subject, and as a result, the aggressiveness towards KOC1-expressing cancer cells can be increased.

The pharmaceutical compositions of the present invention may also comprise an adjuvant known for effectively establishing cellular immunity. An adjuvant refers to a compound that enhances the immune response against an antigen that has immunological activity when administered together (or successively) with the antigen. Known adjuvants described in literatures, for example, Clin Microbiol Rev 1994, 7: 277-89, can be used. Examples of a suitable adjuvant include aluminum salts (aluminum phosphate, aluminum hydroxide, aluminum oxyhydroxide and such), alum, cholera toxin, *Salmonella* toxin, Incomplete Freund's adjuvant (IFA), Complete Freund's adjuvant (CFA), ISCOMatrix, GM-CSF and other immunostimulatory cytokines, oligodeoxynucleotide containing the CpG motif (CpG7909 and such), oil-in-water emulsions, Saponin or its derivatives (QS21 and such), lipopolysaccharide such as Lipid A or its derivatives (MPL, RC529, GLA, E6020 and such), lipopeptides, lactoferrin, flagellin, double-stranded RNA or its derivatives (poli IC and such), bacterial DNA, imidazoquinolines (Imiquimod, R848 and such), C-type lectin ligand (trehalose-6,6'-dibehenate (TDB) and such), CD1d ligand (alpha-galactosylceramide and such), squalene emulsions (MF59, AS03, AF03 and such), PLGA, and such, without being limited thereto. The adjuvant may be contained in another container separate from the pharmaceutical composition comprising a peptide of the present invention in the kits comprising the pharmaceutical composition of the present invention. In this case, the adjuvant and the pharmaceutical composition may be administered to a subject in succession, or mixed together immediately before administration to a subject. Such kits comprising a pharmaceutical composition comprising a peptide of the present invention and an adjuvant are also provided by the present invention. When the pharmaceutical composition of the present invention is a freeze-dried formulation, the kit can further comprise a re-dissolving solution. Further, the present invention provides kits comprising a container that houses a pharmaceutical composition of the present invention and a container that stores an adjuvant. The kit can further comprise as needed a container that stores the re-dissolving solution.

When an oil adjuvant is used as an adjuvant, the pharmaceutical composition of the present invention may be prepared as an emulsion. Emulsions can be prepared, for example, by mixing and stirring the peptide solution prepared as described above and an oil adjuvant. The peptide solution may be one that has been re-dissolved after freeze-drying. The emulsion may be either of the W/O-type emulsion and O/W-type emulsion, and the W/O-type emulsion is preferred for obtaining a high immune response-enhancing effect. IFA can be preferably used as an oil adjuvant, without being limited thereto. Preparation of an emulsion can be carried out immediately before administration to a subject, and in this case, the pharmaceutical composition of the present invention may be provided as a kit comprising the peptide solution of the present invention and an oil adjuvant. When the pharmaceutical composition of the present invention is a freeze-dried formulation, the kit can further comprise a re-dissolving solution.

Further, the pharmaceutical composition of the present invention may be a liposome formulation within which a peptide of the present invention is encapsulated, a granular formulation in which a peptide is bound to beads with several micrometers in diameter, or a formulation in which a lipid is bound to a peptide.

In another embodiment of the present invention, the peptide of the present invention may also be administered in the form of a pharmaceutically acceptable salt. Preferred examples of salts include salts with alkali metals (lithium, potassium, sodium and such), salts with alkaline-earth metals (calcium, magnesium and such), salts with other metals (copper, iron, zinc, manganese and such), salts with organic bases, salts with amines, salts with organic acids (acetic acid, formic acid, propionic acid, fumaric acid, maleic acid, succinic acid, tartaric acid, citric acid, malic acid, oxalic acid, benzoic acid, methanesulfonic acid and such), and salts with inorganic acids (hydrochloric acid, phosphoric acid, hydrobromic acid, sulfuric acid, nitric acid and such). The phrase "pharmaceutically acceptable salt" used herein refers to a salt that retains the biological, physiological, pharmacological and pharmaceutical efficacy and property of the compound. Therefore, pharmaceutical compositions comprising a pharmaceutically acceptable salt of a peptide of the present invention are also encompassed by the present invention. Further, the "peptide of the present invention" also encompasses, in addition to the free peptide, pharmaceutically acceptable salts thereof.

In some embodiments, the pharmaceutical compositions of the present invention may further include a component which primes CTLs. Lipids have been identified as substances capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, E. coli lipoproteins, such as tripalmitoyl-S-glycerylcysteinyl-seryl-serine (P3CSS) can be used to prime CTLs when covalently attached to an appropriate peptide (see, e.g., Deres et al., Nature 1989, 342: 561-4).

Examples of suitable methods for administering the peptides or pharmaceutical compositions of the present invention include oral, epidermal, subcutaneous, intramuscular, intraosseous, peritoneal, and intravenous injections, as well as systemic administration or local administration to the vicinity of the targeted sites, but are not limited thereto. A preferred administration method includes subcutaneous injection to the vicinity of lymph nodes such as the armpit or groin. The administration can be performed by single administration or boosted by multiple administrations. The peptides of the present invention can be administered to a subject in a therapeutically or pharmaceutically effective amount for treating cancer or in a therapeutically or pharmaceutically effective amount for inducing immunity (more specifically CTLs) against KOC1-expressing cancer cells. The dose of the peptides of the present invention can be appropriately adjusted according to the disease to be treated, the patient's age and weight, the method of administration and such. For each of the peptides of the present invention, the dose is usually 0.001 mg-1000 mg, for example, 0.01 mg-100 mg, for example, 0.1 mg-30 mg, for example, 0.1 mg-10 mg, for example, 0.5 mg-5 mg. The dosing interval can be once every several days to several months, and for example, the dosing can be done in a once-per-week interval. A skilled artisan can appropriately select a suitable dose (dosage).

In a preferred embodiment, the pharmaceutical compositions of the present invention comprise a therapeutically effective amount of a peptide of the present invention and a pharmaceutically or physiologically acceptable carrier. In another embodiment, the pharmaceutical compositions of the present invention comprise a therapeutically effective amount of a peptide of the present invention, a pharmaceutically or physiologically acceptable carrier, and an adjuvant. The pharmaceutical compositions of the present invention can comprise 0.001 mg-1000 mg, preferably 0.01 mg-100 mg, more preferably 0.1 mg-30 mg, even more preferably 0.1 mg-10 mg, for example, 0.5 mg-5 mg of a peptide of the present invention. When a pharmaceutical composition of the present invention is an injection, it can comprise a peptide of the present invention at a concentration of 0.001 mg/ml-1000 mg/ml, preferably 0.01 mg/ml-100 mg/ml, more preferably 0.1 mg/ml-30 mg/ml, even more preferably 0.1 mg/ml-10 mg/ml, for example, 0.5 mg/ml-5 mg/ml. In this case, for example, 0.1 to 5 ml, preferably 0.5 ml to 2 ml of the pharmaceutical composition of the present invention can be administered to a subject by injection.

Further, the present invention provides methods of treating and/or preventing cancer and/or preventing postoperative recurrence thereof, which comprise administering to a subject a therapeutically effective amount of a peptide of the present invention or a pharmaceutical composition of the present invention. As described above, the peptides of the present invention can be administered to a subject in a single dose of usually 0.001 mg-1000 mg, for example, 0.01 mg-100 mg, for example, 0.1 mg-30 mg, for example, 0.1 mg-10 mg, or for example, 0.5 mg-5 mg. In a preferred embodiment, the peptides of the present invention are administered to a subject together with an adjuvant. Further, the dosing interval can be once every several days to several months, preferably once every several days to every month, for example, once every week or once every two weeks.

(2) Pharmaceutical Compositions Containing Polynucleotides as the Active Ingredient The pharmaceutical compositions of the present invention can also contain polynucleotides encoding the peptides of the present invention in an expressible form. Herein, the phrase "in an expressible form" means that the polynucleotide, when introduced into a cell, will be expressed as a peptide of the present invention. In an exemplified embodiment, the sequence of the polynucleotide of the present invention includes regulatory elements necessary for expression of the peptide of the present invention. The polynucleotide(s) of the present invention can be equipped with a sequence necessary to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859, 5,589,466, 5,804,566, 5,739,118, 5,736,524, 5,679,647; and WO98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. For example, as a vector to express the peptide of the present invention, vaccinia virus can be used. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide of the present invention into a patient can be either direct, in which case the patient can be directly exposed to a vector harboring the polynucleotide of the present invention, or indirect, in which case, cells are first transformed with the vector harboring the polynucleotide of the present invention in vitro, then the cells are transplanted into the patient. These two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215. Methods commonly known in the art of recombinant DNA technology which can also be used for the present invention are described in Ausubel et al., Current Protocols in Molecular Biology, John Wiley & Sons, N Y, 1993; and Krieger, Gene Transfer and Expression, A Laboratory Manual, Stockton Press, N Y, 1990.

Similar to peptide administration, administration of polynucleotides may be performed by oral, intradermal, subcutaneous, intravenous, intramuscular, intraosseous and/or peritoneal injection, and such. Polynucleotide administration can be a systemic administration or a local administration to the vicinity of the targeted sites. The administration can be performed by single administration or boosted by multiple administrations. The polynucleotides of the present invention can be administered to a subject in a therapeutically or pharmaceutically effective dose for inducing immunity (more specifically CTLs) against KOC1-expressing cancer cells, or in a therapeutically or pharmaceutically effective dose for treating cancer. The dose of a polynucleotide in a suitable carrier or the dose of a polynucleotide in cells transformed with a polynucleotide encoding a peptide of the present invention can be appropriately adjusted according to the disease to be treated, the patient's age and weight, the method of administration and such, and this may be usually 0.001 mg-1000 mg, for example, 0.01 mg-100 mg, for example, 0.1 mg-30 mg, for example, 0.1 mg-10 mg, or for example, 0.5 mg-5 mg. The dosing interval can be once every several days to several months, and for example, the dosing can be done in a once-per-week interval. A skilled artisan can appropriately select a suitable dose (dosage).

X. Methods of Using Peptides, Exosomes, APCs and CTLs

The peptides and polynucleotides of the present invention can be used to induce APCs and CTLs. CTLs can also be induced using the exosomes and APCs of the present invention. The peptides, polynucleotides, exosomes, and APCs can be used in combination with any other compound(s) as long as their CTL-inducing ability is not inhibited. Therefore, CTLs of the present invention can be induced using a pharmaceutical composition comprising any of the peptides, polynucleotides, APCs and exosomes of the present invention. Further, APCs of the present invention can be induced using a pharmaceutical composition comprising a peptide or polynucleotide of the present invention.

(1) Methods of Inducing APCs

The present invention provides methods of inducing APCs having CTL-inducing ability, using a peptide(s) or polynucleotide(s) of the present invention.

The methods of the present invention comprise a step of contacting an APC with a peptide of the present invention in vitro, ex vivo, or in vivo. For example, a method of contacting APCs with the peptide ex vivo may comprise the steps below:

(a) collecting APCs from a subject; and
 (b) contacting the APCs of step (a) with a peptide of the present invention.

The above-described APCs are not limited to a particular type of cell, and cells known to present a proteinaceous antigen on their cell surface to be recognized by lymphocytes, for example, DCs, Langerhans cells, macrophages, B cells, and activated T cells can be used. DCs have the most potent CTL-inducing ability among APCs, and thus it is preferable to use DCs. Any peptides of the present invention can be used by themselves or in combination with other peptides of the present invention. Further, peptides of the present invention can be used in combination with other CTL-inducing peptides (for example, other TAA-derived CTL-inducing peptides).

Meanwhile, when a peptide of the present invention is administered to a subject, APCs are contacted with the peptide in vivo, and as a result, APCs having a high CTL-inducing ability are induced in the body of the subject. Therefore, the methods of the present invention may comprise a step of administering a peptide of the present invention to a subject. Similarly, when a polynucleotide of the present invention is administered to a subject in an expressible form, a peptide of the present invention is expressed in vivo, the expressed peptide is contacted with APCs in vivo, and as a result APCs having a high CTL-inducing ability are induced in the body of the subject. Therefore, the present invention may also comprise a step of administering a polynucleotide of the present invention to a subject.

In order to induce APCs having CTL-inducing ability, the present invention may comprise a step of introducing a polynucleotide of the present invention into APCs. For example, the method may comprise the steps below:
 (a) collecting APCs from a subject; and
 (b) introducing a polynucleotide encoding a peptide of the present invention into the APCs of step (a).
Step (b) can be performed as described in the above "VI. Antigen-presenting cells (APCs)" section.

Thus, in one embodiment, the present invention provides a method of inducing APCs having CTL-inducing ability, which comprises the step (a) or (b) below:
(a) contacting APCs with a peptide of the present invention; and
(b) introducing a polynucleotide encoding a peptide of the present invention into APCs.

Furthermore, the present invention provides a method of preparing APCs having CTL-inducing ability, which comprises the step (a) or (b) below:
 (a) contacting APCs with a peptide of the present invention; or
 (b) introducing a polynucleotide encoding a peptide of the present invention into APCs.

The above-described methods can be performed in vitro, ex vivo, or in vivo, and it is preferable to perform them in vitro or ex vivo. APCs used in the above-described methods may be derived from a subject scheduled for administration of the induced APCs, or they may be derived from a different subject. When APCs derived from a subject (donor) different from the subject scheduled for administration are used, the subject of administration and the donor must have the identical HLA type. In the methods of the present invention, when a peptide having the amino acid sequence selected from among SEQ ID NOs: 5, 28, 30 and 32 or a modified peptide thereof is used as a peptide of the present invention, the HLA type is preferably HLA-A11 (more preferably HLA-A*1101) in both the subject of administration and the donor. Alternatively, APCs used in the above-described methods are preferably APCs that express HLA-A11 (more preferably HLA-A*1101). Similarly, when a peptide having the amino acid sequence selected from among SEQ ID NOs: 61, 62, 63, 64, 67, 74, 77, 52, 79, 80 and 85 or a modified peptide thereof is used as a peptide of the present invention, the HLA is preferably HLA-A33 (more preferably HLA-A*3303) in both the subject of administration and the donor. Alternatively, APCs used in the above-described methods are preferably APCs that express HLA-A33 (more preferably HLA-A*3303). Similarly, when a peptide having the amino acid sequence selected from among SEQ ID NOs: 27, 30 and 52 or a modified peptide thereof is used as a peptide of the present invention, the HLA type is preferably HLA-A03 (more preferably HLA-A*0301) in both the subject of administration and the donor. Alternatively, APCs used in the above-described methods are preferably APCs that express HLA-A03 (more preferably HLA-A*0301). Similarly, when a peptide comprising the amino acid sequence selected from among SEQ ID NOs: 86, 87, 90, 92, 46, 95 and 41 or a modified peptide thereof is used as a peptide of the present invention, the HLA type is preferably HLA-A01 (more preferably HLA-A*0101) in both the subject of administration and the donor. Alternatively, APCs used in the above-described methods are preferably APCs that express HLA-A01 (more preferably HLA-A*0101). The APCs can be prepared using known methods from PBMCs after PBMCs are separated from blood collected from a donor by a specific gravity centrifugal method or such.

In another embodiment, the present invention also provides pharmaceutical compositions that comprise a peptide of the present invention or a polynucleotide encoding the peptide for inducing an APC(s) having CTL-inducing ability.

Alternatively, the present invention further provides use of a peptide of the present invention or a polynucleotide encoding the peptide in the manufacture of a pharmaceutical composition for inducing an APC(s) having CTL-inducing ability.

Alternatively, the present invention further provides peptides of the present invention or polynucleotides encoding the peptides for use in the induction of an APC(s) having CTL-inducing ability.

Alternatively, the present invention further provides methods or processes of manufacturing a pharmaceutical composition for inducing an APC(s), wherein the method or process comprises a step of formulating a peptide of the present invention or a polynucleotide encoding the peptide with a pharmaceutically or physiologically acceptable carrier.

In another embodiment, the present invention further provides methods or processes of manufacturing a pharmaceutical composition for inducing an APC(s) having CTL-inducing ability, wherein the method or process comprises a step of mixing a peptide of the present invention or a polynucleotide encoding the peptide with a pharmaceutically or physiologically acceptable carrier.

APCs induced by the methods of the present invention can induce CTLs specific to KOC1 (i.e., CTLs of the present invention).

(2) Methods of Inducing CTLs

The present invention also provides methods of inducing CTLs using peptides, polynucleotides, exosomes or APCs of the present invention. The present invention further provides methods of inducing CTLs using one or more polynucleotides encoding a polypeptide(s) that can form a T cell receptor (TCR) (i.e., TCR subunit) capable of recognizing a complex of a peptide of present invention and an HLA antigen. Preferably, the methods of inducing CTLs comprise at least one steps selected from below:
 (a) contacting CD8-positive T cells with antigen-presenting cells that present on their surface a complex of an HLA antigen and a peptide of present invention;
 (b) contacting CD8-positive T cells with exosomes that present on its surface a complex of an HLA antigen and a peptide of present invention; and
 (c) introducing into CD8-positive T cells one or more polynucleotides encoding a polypeptide(s) that can form a TCR capable of recognizing a complex of a peptide of present invention and an HLA antigen.

When a peptide(s), a polynucleotide(s), an exosome(s) or an APC(s) of the present invention is administered to a subject, CTLs are induced in the body of the subject and the strength of the immune response targeting KOC1-expressing cancer cells is enhanced. Therefore, the methods of the present invention may comprise a step of administering a peptide(s), a polynucleotide(s), an APC(s) or an exosome(s) of the present invention to a subject.

Alternatively, CTLs can be induced by using them in vitro or ex vivo. For example, the methods of the present invention may include the following steps:
(a) collecting APCs from a subject;
(b) contacting the APCs of step (a) with a peptide of the present invention; and
(c) co-culturing the APCs of step (b) with CD8-positive T cells.

The induced CTLs may be returned to the subject afterwards.

The APCs to be co-cultured with the CD8-positive T cells in step (c) above can also be prepared by introducing into APCs a polynucleotide encoding a peptide of the present invention as described above in the "VI. Antigen-presenting cells (APCs)" section. However, the APCs to be used in the methods of the present invention are not limited thereto, and any APCs that present on their surface a complex of an HLA antigen and a peptide of the present invention can be used.

In the methods of the present invention, instead of such APCs, exosomes that present on their surface a complex of an HLA antigen and a peptide of the present invention can also be used. That is, the methods of the present invention can comprise a step of co-culturing with exosomes that present on their surface a complex of an HLA antigen and a peptide of the present invention. Such exosomes can be prepared by the above-described methods in the "V. Exosomes" section.

Further, CTLs can also be induced by introducing into a CD8-positive T cell a vector comprising a polynucleotide encoding each subunit of a TCR capable of binding to a peptide of the present invention presented by an HLA antigen on the cell surface. Such transformation can be carried out as described above in the "VIII. T cell receptors (TCRs)" section.

Accordingly, in one embodiment, the present invention provides methods of inducing CTLs, comprising a step selected from below:
(a) co-culturing CD8-positive T cells with APCs that present on their surface a complex of an HLA antigen and a peptide of present invention;
(b) co-culturing CD8-positive T cells with exosomes that present on their surface a complex of an HLA antigen and a peptide of present invention; and
(c) introducing into CD8-positive T cells, a vector comprising a polynucleotide encoding each subunit of a TCR capable of binding to a peptide of the present invention presented by an HLA antigen on a cell surface.

The above-described methods can be performed in vitro, ex vivo, or in vivo, and it is preferable to perform them in vitro or ex vivo. APCs or exosomes and CD8-positive T cells used in the above-described methods may be derived from a subject scheduled for administration of the induced CTLs, or they may be derived from a different subject. When APCs or exosomes and CD8-positive T cells derived from a subject (donor) different from the subject scheduled for administration are used, the subject of administration and the donor must have the identical HLA type. For example, when a peptide having the amino acid sequence selected from among SEQ ID NOs: 5, 28, 30 and 32 or a modified peptide thereof is used as peptides of the present invention, the HLA type in both the subject of administration and the donor is preferably HLA-A11 (more preferably HLA-A*1101). Alternatively, APCs or exosomes used in the above-described methods are preferably APCs or exosomes that present on their surface a complex of HLA-A11 (more preferably HLA-A*1101) and a peptide of the present invention (a peptide having the amino acid sequence selected from among SEQ ID NOs: 5, 28, 30 and 32 or a modified peptide thereof). In this case, the induced CTLs show a specific cytotoxic activity against cells that present a complex of HLA-A11 and a peptide of the present invention (for example, KOC1-expressing HLA-A11-positive cells). Alternatively, for example, when a peptide having the amino acid sequence selected from among SEQ ID NOs: 61, 62, 63, 64, 67, 74, 77, 52, 79, 80 and 85 or a modified peptide thereof is used as peptides of the present invention, the HLA in the subject of administration and the donor is preferably both HLA-A33 (more preferably HLA-A*3303). Alternatively, APCs or exosomes used in the above-described methods are preferably APCs or exosomes that present on their surface a complex of HLA-A33 (more preferably HLA-A*3303) and a peptide of the present invention (a peptide having the amino acid sequence selected from among SEQ ID NOs: 61, 62, 63, 64, 67, 74, 77, 52, 79, 80 and 85 or a modified peptide thereof). In this case, the induced CTLs show a specific cytotoxic activity against cells that present a complex of HLA-A33 and a peptide of the present invention (for example, KOC1-expressing HLA-A33-positive cells). Alternatively, for example, when a peptide having the amino acid sequence selected from among SEQ ID NOs: 27, 30 and 52 or a modified peptide thereof is used as peptides of the present invention, the HLA type in both the subject of administration and the donor is preferably HLA-A03 (more preferably HLA-A*0301). Alternatively, APCs or exosomes used in the above-described methods are preferably APCs or exosomes that present on their surface a complex of HLA-A03 (more preferably HLA-A*0301) and a peptide of the present invention (a peptide having the amino acid sequence selected from among SEQ ID NOs: 27, 30 and 52 or a modified peptide thereof). In this case, the induced CTLs show a specific cytotoxic activity against cells that present a complex of HLA-A03 and a peptide of the present invention (for example, KOC1-expressing HLA-A03-positive cells). Alternatively, for example, when a peptide having the amino acid sequence selected from among SEQ ID NOs: 86, 87, 90, 92, 46, 95 and 41 or a modified peptide thereof is used as peptides of the present invention, the HLA type in both the subject of administration and the donor is preferably HLA-A01 (more preferably HLA-A*0101). Alternatively, APCs or exosomes used in the above-described methods are preferably APCs or exosomes that present on their surface a complex of HLA-A01 (more preferably HLA-A*0101) and a peptide of the present invention (a peptide having the amino acid sequence selected from among SEQ ID NOs: 86, 87, 90, 92, 46, 95 and 41 or a modified peptide thereof). In this case, the induced CTLs show a specific cytotoxic activity against cells that present a complex of HLA-A01 and a peptide of the present invention (for example, KOC1-expressing HLA-A01-positive cells).

In another embodiment, the present invention also provides compositions or pharmaceutical compositions for inducing CTLs, comprising at least one active ingredient selected from below:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

In another embodiment, the present invention also provides use of an active ingredient selected from below in the manufacture of compositions or pharmaceutical compositions for inducing CTLs:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

Alternatively, the present invention further provides an active ingredient selected from below for use in inducing CTLs:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

Alternatively, the present invention further provides a method or process for manufacturing a composition or pharmaceutical composition for inducing CTLs, which is a method or process that comprises a step of formulating an active ingredient selected from below with a pharmaceutically or physiologically acceptable carrier:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

In another embodiment, the present invention further provides a method or process for manufacturing a composition or pharmaceutical composition for inducing CTLs, which is a method or process that comprises a step of mixing an active ingredient selected from below with a pharmaceutically or physiologically acceptable carrier:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

XI. Methods of Inducing an Immune Response

The present invention further provides methods of inducing an immune response against KOC1-expressing cancers. Applicable cancers include bladder cancer, cervical cancer, cholangiocellular cancer, chronic myeloid leukemia (CML), colon cancer, rectum cancer, esophagus cancer, diffuse gastric cancer, non-small-cell lung cancer, small-cell lung cancer, lymphoma, osteosarcoma, ovarian cancer, kidney cancer, head and neck cancer, soft tissue tumor, testis cancer and such, but are not limited thereto. It is preferable that the cancer expresses at least one HLA selected from among HLA-A11, HLA-A33, HLA-A03 and HLA-A01.

The present invention further provides methods of inducing an immune response against KOC1-expressing cancer cells. KOC1 is recognized to be overexpressed in various types of cancers described above. Thus, when an immune response against KOC1-expressing cancer cells is induced, proliferation of the cancer cells is inhibited as a result. Accordingly, the present invention further provides methods of inhibiting proliferation of KOC1-expressing cancer cells. The methods of the present invention are suitable, in particular, for inhibiting proliferation of cancer cells expressing KOC1 and at least one HLA selected from among HLA-A11, HLA-A33, HLA-A03 and HLA-A01.

The methods of the present invention may comprise a step of administering a composition comprising any of the peptides of the present invention or a polynucleotide(s) encoding the peptide(s). The methods of the present invention also contemplate administration of APCs or exosomes presenting any of the peptides of the present invention. The details can be referred to the "IX. Pharmaceutical compositions" section, particularly portions describing regarding use of the pharmaceutical compositions of the present invention as vaccines. In addition, exosomes and APCs that can be used in the methods of the present invention for inducing an immune response are described in detail in "V. Exosomes", "VI. Antigen-presenting cells (APCs)" and in Items (1) and (2) of "X. Methods of using peptides, exosomes, APCs and CTLs" described above.

In another embodiment, the present invention provides pharmaceutical compositions or vaccines for inducing an immune response against KOC1-expressing cancers, wherein the pharmaceutical composition or vaccine comprises an active ingredient selected from below:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention also provides pharmaceutical compositions or vaccines for inducing an immune response against KOC1-expressing cancer cells, wherein the pharmaceutical composition or vaccine comprises an active ingredient selected from below:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention further provides pharmaceutical compositions or vaccines for inhibiting proliferation of KOC1-expressing cancer cells, wherein the pharmaceutical composition or vaccine comprises an active ingredient selected from below:
(a) a peptide of the present invention;
(b) a polynucleotide encoding a peptide of the present invention in an expressible form;

(c) an APC that presents on its surface a peptide of the present invention;
(d) an exosome that presents on its surface a peptide of the present invention; and
(e) a CTL of the present invention.

In another embodiment, the present invention provides use of an active ingredient selected from below in the manufacture of pharmaceutical compositions or vaccines for inducing an immune response against KOC1-expressing cancers:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention also provides use of an active ingredient selected from below in the manufacture of pharmaceutical compositions or vaccines for inducing an immune response against KOC1-expressing cancer cells:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention further provides use of an active ingredient selected from below in the manufacture of pharmaceutical compositions or vaccines for inhibiting proliferation of KOC1-expressing cancer cells:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

The present invention further provides methods or processes for manufacturing pharmaceutical compositions that induce an immune response against KOC1-expressing cancers, which is a method that may comprise a step of mixing or formulating a peptide or polynucleotide of the present invention with a pharmaceutically acceptable carrier.

Alternatively, the present invention provides methods for inhibiting proliferation of KOC1-expressing cancer cells or methods of inducing an immune response against KOC1-expressing cancers, which comprises a step of administering to a subject vaccines or pharmaceutical compositions comprising an active ingredient selected from below:
  (a) a peptide of the present invention;
  (b) a polynucleotide encoding a peptide of the present invention in an expressible form;
  (c) an APC that presents a peptide of the present invention on its surface;
  (d) an exosome that presents a peptide of the present invention on its surface; and
  (e) a CTL of the present invention.

In the context of the present invention, KOC1-expressing cancers can be treated by administering a peptide, a polynucleotide, an APC, an exosome and/or a CTL of the present invention. Alternatively, an immune response against KOC1-expressing cancers can be induced by administering a peptide, a polynucleotide, an APC, an exosome and/or a CTL of the present invention. Examples of such cancers include bladder cancer, cervical cancer, cholangiocellular cancer, chronic myeloid leukemia (CML), colon cancer, rectum cancer, esophagus cancer, diffuse gastric cancer, non-small-cell lung cancer, small-cell lung cancer, lymphoma, osteosarcoma, ovarian cancer, kidney cancer, head and neck cancer, soft tissue tumor, testis cancer and such, but are not limited thereto. Further, an immune response against KOC1-expressing cancer cells can be induced by administering a peptide, a polynucleotide, an APC, an exosome and/or a CTL of the present invention. Therefore, before administering a vaccine or pharmaceutical composition comprising an active ingredient described above, it is preferable to confirm whether the level of KOC1 expression at a diseased site in the subject to be treated is augmented or not.

Thus, in one embodiment, the present invention provides a method of treating a KOC1-expressing cancer in a patient in need of the cancer treatment, wherein the method comprises the steps below:
(i) measuring the level of KOC1 expression in a biological sample collected from the diseased site of a subject with cancer;
(ii) identifying a subject with KOC1-expressing cancer based on the KOC1 expression level measured in (i); and
(iii) administering to the subject with KOC1-expressing cancer at least one ingredient selected from the group consisting of (a) to (e) above.

Alternatively, the present invention further provides vaccines and pharmaceutical compositions comprising at least one active ingredient selected from the group consisting of (a) to (e) above for administration to a subject with KOC1-expressing cancer. The present invention further provides a method of identifying or selecting a subject to be treated with at least one active ingredient selected from the group consisting of (a) to (e) above, wherein the method comprises the steps below:
(i) measuring the level of KOC1 expression in a biological sample collected from the diseased site of a subject with cancer;
(ii) identifying a subject with KOC1-expressing cancer based on the KOC1 expression level measured in (i); and
(iii) identifying or selecting the subject identified in (ii) as a subject who may be treated with at least one active ingredient selected from the group consisting of (a) to (e) above.

Biological samples collected from a subject for measuring the KOC1 expression level in the above-described methods are not particularly limited, and for example, tissue samples containing cancer cells collected by biopsy or such can be preferably used. The KOC1 expression level in a biological sample can be measured by known methods, and for example, methods that detect transcription products of the KOC1 gene by probes or PCR methods (for example, cDNA microarray method, Northern blot method, RT-PCR method or such), methods that detect translation products of the KOC1 gene by antibodies or such (for example, Western blot method, immunostaining method or such), and such can be used. Further, biological samples may be blood samples, and in this case, the blood level of an antibody against KOC1 is measured, and the KOC1 expression level at a diseased site may be assessed based on the blood level. The blood level of an antibody against KOC1 or a fragment thereof can be measured using known methods, and for example, enzyme immunoassay (EIA), enzyme-linked immunosorbent assay (ELISA), radioimmunoassay (RIA) and such using the KOC1 protein or a peptide of the present invention as an antigen can be used.

Normally, in tissues and cells that do not express KOC1, there is almost no detection of KOC1 transcription products and translation products. Thus, when a transcription product or a translation product of KOC1 is detected in cancer cells or a tissue sample containing cancer cells collected from a subject, one can determine that the subject's cancer expresses KOC1. In blood samples of a subject that does not have KOC1-expressing cancer, there is almost no detection of antibodies against KOC1 or fragments thereof. Thus, when antibodies against KOC1 or fragments thereof are detected in a blood sample collected from a subject, one can determine that the subject's cancer expresses KOC1. Whether a subject's cancer expresses KOC1 or not may also be determined by comparison with the measurement results of the same type of biological material collected from a non-cancerous site of the subject or the same type of biological material collected from a subject who does not have cancer (normal control sample). That is, in comparison with the level of the target of measurement in a normal control sample (normal control level), when the level in the biological sample of the test subject is elevated, the subject's cancer is assessed to be expressing KOC1. For example, when the amount of the target of measurement detected is increased by at least 10% or higher in comparison with the normal control level, the subject's cancer may be assessed to be expressing KOC1. It is desirable that the amount of the target of measurement detected is increased by preferably 25% or higher, and more preferably 50% or higher than the normal control level. Further, the amount of a transcription product or a translation product of KOC1 detected may be evaluated by normalizing against the detected amount of a known housekeeping gene such as beta-Actin, glyceraldehyde-3-phosphate dehydrogenase, or ribosomal protein P1.

In a preferred embodiment, it is preferable to confirm the HLA type of the subject before administering at least one active ingredient selected from the group consisting of (a) to (e) above. For example, for the subjects to be administered with an active ingredient in association with a peptide having the amino acid sequence selected from among SEQ ID NOs: 5, 28, 30 and 32, it is preferable to select HLA-A11-positive subjects. For the subjects to be administered with an active ingredient in association with a peptide having the amino acid sequence selected from among SEQ ID NOs: 61, 62, 63, 64, 67, 74, 77, 52, 79, 80 and 85, it is preferable to select HLA-A33-positive subjects. For the subjects to be administered with an active ingredient in association with a peptide having the amino acid sequence selected from among SEQ ID NOs: 27, 30 and 52, it is preferable to select HLA-A03-positive subjects. For the subjects to be administered with an active ingredient in association with a peptide having the amino acid sequence selected from among SEQ ID NOs: 86, 87, 90, 92, 46, 95 and 41, it is preferable to select HLA-A01-positive subjects.

The present invention further provides complexes of a peptide of the present invention and HLA. The complexes of the present invention described above may be monomers or multimers. When a complex of the present invention is a multimer, the number of polymerization is not particularly limited, and it can be a multimer of any number of polymerization. Examples include a tetramer, pentamer, hexamer and such, but are not limited thereto. The multimers of the present invention also encompass dextramers (WO2002/072631) and streptamers (Knabel M et al., Nat Med. 2002 June; 8(6): 631-7). Complexes of a peptide of the present invention and HLA can be prepared according to known methods (for example, Altman J D et al., Science. 1996, 274(5284): 94-6; WO2002/072631; WO2009/003492; Knabel M et al., Nat Med. 2002 June; 8(6): 631-7, and such). The complexes of the present invention, for example, can be used in the quantification of CTLs specific to a peptide of the present invention. For example, a blood sample is collected from a subject administered with a pharmaceutical composition of the present invention, and CD4-negative cells are prepared after separation of PBMCs and contacted with a fluorescent dye-conjugated complex of the present invention. Then, the percentage of CTLs specific to a peptide of the present invention can be measured by flow cytometry analysis. For example, immune response-inducing effects by a pharmaceutical composition of the present invention can be monitored by measuring the specific CTLs against a peptide of the present invention before, during and/or after administration of the pharmaceutical composition of the present invention.

XII. Antibodies

The present invention further provides antibodies that bind to the peptide of the present invention. Preferable antibodies bind specifically to a peptide of the present invention, but do not bind (or weakly bind) to one that is not the peptide of the present invention. In another embodiment, such an antibody may include an antibody that recognizes a peptide in the context of HLA molecules, i.e., an antibody that binds to a peptide-MHC complex. The binding specificity of an antibody can be confirmed by inhibition assay. That is, if the binding between an antibody to be analyzed and a full-length KOC1 polypeptide is inhibited in the presence of a peptide of the present invention, this antibody is shown to specifically bind to the peptide of the present invention. Antibodies against peptides of the present invention can be used in assays of disease diagnosis and prognosis, as well as subject selection for administration of the pharmaceutical compositions of the present invention and monitoring of the pharmaceutical compositions of the present invention.

The present invention also provides various immunological assays for detecting and/or quantifying peptides of the present invention or fragments thereof. Such immunological assays include radioimmunoassay, immunochromatography, enzyme-linked immunosorbent assay (ELISA), enzyme-linked immunofluorescence assay (ELIFA) and such, without being limited thereto, and are performed within the scope of the various immunological assay formats well known in the art.

The antibodies of the present invention can be used in immunological imaging methods that can detect KOC1-expressing cancers, and examples thereof include radioactive scintigraphic imaging using a labelled antibody of the present invention, without being limited thereto. Such assay methods are used clinically in the detection, monitoring, and prognosis of KOC1-expressing cancers; and examples of such cancer include bladder cancer, cervical cancer, cholangiocellular cancer, chronic myeloid leukemia (CML), colon cancer, rectum cancer, esophagus cancer, diffuse gastric cancer, non-small-cell lung cancer, small-cell lung cancer, lymphoma, osteosarcoma, ovarian cancer, kidney cancer, head and neck cancer, soft tissue tumor, testis cancer and such, without being limited thereto.

The antibodies of the present invention can be used in any arbitrary form such as monoclonal antibodies or polyclonal antibodies, and may further include anti-sera obtained by immunizing an animal such as a rabbit with a peptide of the present invention, all classes of polyclonal antibodies and monoclonal antibodies, human antibodies, as well as chimeric antibodies and humanized antibodies generated through gene recombination.

The peptide of the present invention or a fragment thereof used as an antigen for obtaining antibodies can be obtained by chemical synthesis or genetic engineering techniques based on the amino acid sequences disclosed herein.

The peptide used as an immunizing antigen may be a peptide of the present invention or a fragment of a peptide of the present invention. Further, the peptide may be bound to or conjugated with a carrier for increasing immunogenicity. Keyhole limpet hemocyanin (KLH) is well-known as a carrier. Methods for binding KLH to a peptide are also well known in the art.

Any mammal can be immunized with an antigen described above, and it is preferable to consider the compatibility with the parent cell used in cell fusion when generating a monoclonal antibody. Generally, animals of the order Rodentia, Lagomorpha or Primate can be used. Animals of the order Rodentia include, for example, mice, rats and hamsters. Animals of the order Lagomorpha include, for example, rabbits. Animals of the order Primate include, for example, Catarrhini monkeys (old world monkeys) such as cynomolgus monkey (*Macaca fascicularis*), rhesus monkeys, hamadryas, and chimpanzee.

Methods of immunizing animals with an antigen are known in the art. Intraperitoneal injection and subcutaneous injection of an antigen are standard methods for immunizing mammals. More specifically, an antigen is diluted and suspended in an appropriate amount of phosphate buffered saline (PBS), physiological saline, or such. As needed, an antigen suspension solution can be administered to mammals after being mixed with an appropriate amount of a standard adjuvant such as Freund's complete adjuvant and emulsified. Then, it is preferable to administer the antigen mixed with an appropriate amount of a Freund's incomplete adjuvant several times every 4 to 21 days. A suitable carrier may be used for immunization. After the above immunization, the serum can be examined by standard method with respect to increase in the quantity of the desired antibody.

Polyclonal antibodies against a peptide of the present invention can be prepared by collecting blood from mammals that have been confirmed with an increase in the serum level of the desired antibody after immunization, and separating the serum from blood by any conventional method. A polyclonal antibody may be a polyclonal antibody-containing serum, or a polyclonal antibody-containing fraction may be isolated from the serum. Immunoglobulin G or M can be prepared from fractions that recognize only a peptide of the present invention by, for example, using an affinity column conjugated with the peptide of the present invention, and then further purifying the fractions using a protein A or protein G column.

In order to prepare monoclonal antibodies, upon confirming an increase in the serum level of the desired antibody after immunization, immune cells are collected from the mammals and subjected to cell fusion. Immune cells used for cell fusion may be preferably obtained from the spleen. For the other parent cells fused with the above immune cells, for example, a mammalian myeloma cell, preferably a myeloma cell that has acquired a property for drug selection of fusion cells can be used.

The above immune cells can be fused with myeloma cells by following known methods, for example, the method of Milstein et al. (Galfre and Milstein, Methods Enzymol 73: 3-46 (1981)).

Hybridomas obtained by cell fusion can be selected by culturing them in a standard selection medium such as the HAT medium (a medium containing hypoxanthine, aminopterin and thymidine). Cell culturing is continued in the HAT medium for a sufficient period of time (for example, several days to several weeks) to allow death of all other cells (non-fused cells) besides the desired hybridomas. Then, hybridoma cells producing the desired antibody can be screened and cloned by performing a standard limiting dilution.

In addition to the above methods of immunizing a non-human animal with an antigen for hybridoma preparation, human lymphocytes such as EB virus-infected lymphocytes can be immunized in vitro with a peptide, cells expressing the peptide, or lysates thereof. Then, the immunized lymphocytes can be fused with immortalized human-derived myeloma cells such as U266 to obtain hybridomas producing a desired human antibody capable of binding to the peptide (JPS63-17688).

Next, the obtained hybridoma is transplanted into the abdominal cavity of a mouse, and the ascites is extracted. The obtained monoclonal antibody can be purified by, for example, ammonium sulfate precipitation, protein A or protein G column, DEAE ion-exchange chromatography, or affinity column conjugated with the peptide of the present invention.

Alternatively, antibody-producing immune cells such as the immunized lymphocytes can be immortalized by a cancer gene and used for the preparation of monoclonal antibodies.

The monoclonal antibodies obtained as such can also be prepared by recombination using genetic engineering techniques (see, e.g., Borrebaeck and Larrick, Therapeutic Monoclonal Antibodies published in United Kingdom by MacMillan Publishers LTD (1990)). For example, an antibody-encoding DNA can be cloned from immune cells such as antibody-producing hybridoma or immunized lymphocytes and inserted into a suitable vector, and then this is introduced into host cells to prepare a recombinant antibody. The present invention also provides recombinant antibodies prepared as described above.

Further, the antibodies of the present invention may be antibody fragments or modified antibodies, as long as they bind to the peptides of the present invention. For example, it is desirable that the antibody fragment contains an antigen-binding site(s) of the antibodies. Specifically, the antibody fragments may be Fab, F(ab')$_2$, Fv, or a single chain Fv(scFv) in which Fv fragments derived from an H chain and an L chain are linked with a suitable linker (Huston et al., Proc Natl Acad Sci USA 85: 5879-83 (1988)). More specifically, antibody fragments may be generated by treating an antibody with an enzyme such as papain or pepsin. Alternatively, a gene encoding an antibody fragment may be constructed, inserted into an expression vector, and expressed in an appropriate host cell (see, e.g., Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

Antibodies may be modified by conjugation with various molecules such as polyethyleneglycol (PEG). The present invention provides such modified antibodies. Modified antibodies can be obtained by chemically modifying the antibodies. These modification methods are conventional in the art.

Alternatively, the antibodies of the present invention can be obtained as chimeric antibodies of a non-human antibody-derived variable region and a human antibody-derived constant region, or as humanized antibodies comprising a non-human antibody-derived complementarity determining region (CDR) and a human antibody-derived framework region (FR) and constant region. Such antibodies can be prepared according to known techniques. Humanization can be carried out by substituting a human antibody sequence(s) with a corresponding non-human antibody CDR sequence(s) (see, e.g., Verhoeyen et al., Science 239: 1534-6 (1988)). Thus, such humanized antibodies are chimeric antibodies in which the substantially less than an intact human variable domain has been substituted with a corresponding sequence from a non-human species.

Intact human antibodies comprising a human variable region in addition to the human framework and constant regions can also be used. Such antibodies can be generated using various techniques known in the art. For example, in vitro methods include use of recombinant libraries of human antibody fragments presented on bacteriophages (for example, Hoogenboom & Winter, J. Mol. Biol. 227: 381 (1991)). Similarly, human antibodies can also be generated by introducing human immunoglobulin gene loci into transgenic animals, for example, mice, in which the endogenous immunoglobulin genes have been partially or completely inactivated. This approach is described in, for example, U.S. Pat. Nos. 6,150,584, 5,545,807, 5,545,806, 5,569,825, 5,625,126, 5,633,425 and 5,661,016.

Antibodies obtained as described above may be purified to homogeneity. For example, antibody separation and purification can be performed according to separation methods and purification methods used for general proteins. For example, an antibody can be separated and isolated by appropriately selecting and combining use of column chromatographies such as affinity chromatography, filter, ultrafiltration, salting-out, dialysis, SDS-polyacrylamide gel electrophoresis and isoelectric focusing electrophoresis (Antibodies: A Laboratory Manual. Ed Harlow and David Lane, Cold Spring Harbor Laboratory (1988)), but are not limited thereto. Protein A column and protein G column can be used as the affinity column. Exemplary protein A columns to be used include, for example, Hyper D, POROS and Sepharose F.F. (Pharmacia).

Besides affinity chromatography, exemplary chromatography includes, for example, ion-exchange chromatography, hydrophobic chromatography, gel filtration, reversed-phase chromatography, adsorption chromatography and such (Strategies for Protein Purification and Characterization: A Laboratory Course Manual. Ed Daniel R. Marshak et al., Cold Spring Harbor Laboratory Press (1996)). The chromatography procedures can be carried out by liquid-phase chromatography such as HPLC and FPLC.

The antigen-binding activity of an antibody of the present invention can be measured, for example, by using absorbance measurement, enzyme-linked immunosorbent assay (ELISA), enzyme immunoassay (EIA), radioimmunoassay (RIA), and/or immunofluorescence (IF). In the case of ELISA, an antibody of the present invention is immobilized onto a plate, a peptide of the present invention is applied to the plate, and then a sample containing the desired antibody, such as culture supernatant of antibody-producing cells or purified antibodies, is applied. Next, a secondary antibody that recognizes the primary antibody and is labelled with an enzyme such as alkaline phosphatase is applied and the plate is incubated. Then, after washing, an enzyme substrate such as p-nitrophenyl phosphate is applied to the plate, and the antigen-binding activity of the sample is evaluated by measuring absorbance. To assess the binding activity of an antibody, peptide fragments such as C-terminal or N-terminal fragments may be used as an antigen. BIAcore (Pharmacia) may be used to evaluate the activity of an antibody of the present invention.

It is possible to detect or measure a peptide of the present invention using the above methods, by exposing an antibody of the present invention to a sample assumed to contain the peptide of the present invention, and detecting or measuring an immune complex formed between the antibody and the peptide.

For example, an antibody of the present invention can be used to detect a peptide of the present invention present in the blood sample (for example, serum sample) of a subject. Alternatively, an antibody of the present invention present in the blood sample (for example, serum sample) of a subject can also be detected using a peptide of the present invention. The result of measuring a peptide of the present invention or an antibody of the present invention in the blood sample of a subject can be utilized to the subject selection for administration of the pharmaceutical compositions of the present invention or monitoring of the efficacy of the pharmaceutical compositions of the present invention. In addition, it has been reported that patients having an antibody against a peptide administered as vaccine may have high responsiveness to the vaccine. Therefore, the peptide of the present invention can be utilized as an immunoassay antigen for selecting a patient with high responsiveness when the peptide is administered as a vaccine using an antibody of the patient as an index.

XIII. Vectors and Host Cells

The present invention provides vectors comprising a polynucleotide encoding a peptide of the present invention and host cells introduced with the vectors. A vector of the present invention may be used to keep a polynucleotide of the present invention in a host cell, to express a peptide of the present invention in a host cell, or to administer a polynucleotide of the present invention for gene therapy.

When *E. coli* is a host cell and a vector is amplified and produced in a large amount in *E. coli* (for example, JM109, DH5-alpha, HB101 or XL1-Blue), the vector needs to have a "replication origin" for amplification in *E. coli* and a marker gene for selection of transformed *E. coli* (for example, a drug resistance gene selected by a drug such as ampicillin, tetracycline, kanamycin, chloramphenicol). For example, the M13-series vectors, pUC-series vectors, pBR322, pBluescript, pCR-Script and such can be used. In addition, pGEM-T, pDIRECT and pT7 can be used for cloning as well as the above vectors. When a vector is used in the production of a peptide of the present invention, an expression vector can be used. For example, an expression vector for expression in *E. coli* needs to have the above features for amplification in *E. coli*. When *E. coli* such as JM109, DH5-alpha, HB101 or XL1-Blue are used as a host cell, the vector needs to have a promoter, for example, lacZ promoter (Ward et al., Nature 341: 544-6 (1989); FASEB J 6: 2422-7 (1989)), araB promoter (Better et al., Science 240: 1041-3 (1988)), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may contain a signal sequence for peptide secretion. An exemplary signal sequence that directs the peptide to be secreted to the periplasm of the *E. coli* is the pelB signal sequence (Lei et al., J Bacteriol 169: 4379 (1987)). Means for introducing the vectors into the target host cells include, for example, the calcium chloride method and the electroporation method.

In addition to *E. coli*, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vectors derived from yeast (e.g., "*Pichia* Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells such as CHO, COS or NIH3T3 cells, the vector needs to carry a promoter necessary for expression in such cells, for example, the SV40 promoter (Mulligan et al., Nature 277: 108 (1979)), the MMLV-LTR promoter, the EF1-alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

The embodiments of the present invention are exemplified below based on the above explanation; however, the present invention is not limited to these embodiments.

[1] A peptide of less than 15 amino acids having cytotoxic T cell (CTL)-inducing ability, which comprises the amino acid sequence selected from the group of:
  (a) the amino acid sequence selected from the group consisting of SEQ ID NOs: 5, 28, 30, 32, 61, 62, 63, 64, 67, 74, 77, 52, 79, 80, 85, 27, 86, 87, 90, 92, 46, 95 and 41; and
  (b) the amino acid sequence in which one, two or several amino acids are substituted, deleted, inserted and/or added to the amino acid sequence selected from the group consisting of SEQ ID NOs: 5, 28, 30, 32, 61, 62, 63, 64, 67, 74, 77, 52, 79, 80, 85, 27, 86, 87, 90, 92, 46, 95 and 41.

[2] The peptide of [1], which is selected from the group consisting of (i) to (iv) below:
  (i) a peptide comprising the amino acid sequence in which one or more substitution(s) selected from the group consisting of (a) to (d) below is introduced into the amino acid sequence selected from the group consisting of SEQ ID NOs: 5, 28, 30 and 32:
    (a) the second amino acid from the N terminus is substituted with an amino acid selected from the group consisting of threonine, valine, isoleucine, leucine, phenylalanine and tyrosine;
    (b) the third amino acid from the N terminus is substituted with an amino acid selected from the group consisting of leucine, phenylalanine, tyrosine, isoleucine and alanine;
    (c) the seventh amino acid from the N terminus is substituted with an amino acid selected from the group consisting of leucine, isoleucine, tyrosine, valine and phenylalanine; and
    (d) the C-terminal amino acid is substituted with an amino acid selected from the group consisting of lysine and arginine;
  (ii) a peptide comprising the amino acid sequence in which one or more substitution(s) selected from the group consisting of (a) to (c) below is introduced into the amino acid sequence selected from the group consisting of SEQ ID NOs: 61, 62, 63, 64, 67, 74, 77, 52, 79, 80 and 85:
    (a) the first amino acid from the N terminus is substituted with an amino acid selected from the group consisting of aspartic acid and glutamic acid;
    (b) the second amino acid from the N terminus is substituted with an amino acid selected from the group consisting of phenylalanine, tyrosine, alanine, isoleucine, leucine and valine; and
    (c) the C-terminal amino acid is substituted with an amino acid selected from the group consisting of arginine and lysine;
  (iii) a peptide comprising the amino acid sequence in which one or more substitution(s) selected from the group consisting of (a) to (b) below is introduced into the amino acid sequence selected from the group consisting of SEQ ID NOs: 27, 30 and 52:
    (a) the second amino acid from the N terminus is substituted with an amino acid selected from the group consisting of leucine, methionine, valine, alanine, isoleucine, serine and threonine; and
    (b) the C-terminal amino acid is substituted with an amino acid selected from the group consisting of arginine, lysine, tyrosine and phenylalanine; and
  (iv) a peptide comprising the amino acid sequence in which one or more substitution(s) selected from the group consisting of (a) to (c) below is introduced into the amino acid sequence selected from the group consisting of SEQ ID NOs: 86, 87, 90, 92, 46, 95 and 41:
    (a) the second amino acid from the N terminus is substituted with an amino acid selected from the group consisting of threonine and serine;
    (b) the third amino acid from the N terminus is substituted with an amino acid selected from the group consisting of aspartic acid and glutamic acid; and
    (c) the C-terminal amino acid is substituted with tyrosine.

[3] The peptide of [1], which consists of the amino acid sequence selected from the group consisting of SEQ ID NOs: 5, 28, 30, 32, 61, 62, 63, 64, 67, 74, 77, 52, 79, 80, 85, 27, 86, 87, 90, 92, 46, 95 and 41.

[4] A polynucleotide, which encodes the peptide of any one of [1] to [3].

[5] A composition comprising a pharmaceutically acceptable carrier and at least one ingredient selected from the group consisting of (a) to (e) below:
  (a) one or more types of peptides of any one of [1] to [3];
  (b) one or more types of polynucleotides encoding the peptide(s) of any one of [1] to [3] in an expressible form;
  (c) an antigen-presenting cell (APC) that presents on its cell surface a complex of the peptide of any one of [1] to [3] and an HLA antigen;
  (d) an exosome that presents on its cell surface a complex of the peptide of any one of [1] to [3] and an HLA antigen; and (e) a CTL that targets the peptide of any one of [1] to [3].
[6] The composition of [5], which is a composition for inducing a CTL(s), wherein the ingredient is at least one ingredient selected from the group consisting of (a) to (d) below:
  (a) one or more types of peptides of any one of [1] to [3];
  (b) one or more types of polynucleotides encoding the peptide(s) of any one of [1] to [3] in an expressible form;
  (c) an antigen-presenting cell (APC) that presents on its cell surface a complex of the peptide of any one of [1] to [3] and an HLA antigen; and
  (d) an exosome that presents on its cell surface a complex of the peptide of any one of [1] to [3] and an HLA antigen.
[7] The composition of [5], which is a pharmaceutical composition.
[8] The composition of [7], which is for one or more uses selected from the group consisting of (i) cancer treatment, (ii) cancer prevention (prophylaxis) and (iii) prevention (prophylaxis) of postoperative cancer recurrence.
[9] The composition of [7], which is for inducing an immune response against cancer.
[10] The composition of [8] or [9], wherein the cancer is selected from the group consisting of bladder cancer, cervical cancer, cholangiocellular cancer, chronic myeloid leukemia (CML), colon cancer, rectum cancer, esophagus cancer, diffuse gastric cancer, non-small-cell lung cancer, small-cell lung cancer, lymphoma, osteosarcoma, ovarian cancer, kidney cancer, head and neck cancer, soft tissue tumor and testis cancer.
[11] The composition of any one of [5] to [10], which is formulated for administration to a subject positive for at least one HLA selected from the group consisting of HLA-A11, HLA-A33, HLA-A03 and HLA-A01.
[12] A method of inducing an APC(s) having CTL-inducing ability, which comprises a step selected from the group consisting of (a) and (b) below:
  (a) contacting an APC(s) with the peptide of any one of [1] to [3] in vitro, ex vivo or in vivo; and
  (b) introducing a polynucleotide encoding the peptide of any one of [1] to [3] into an APC(s).
[13] A method of inducing a CTL(s), which comprises a step selected from the group consisting of (a) to (c) below:
  (a) co-culturing a CD8-positive T cell(s) with an APC(s) that presents on its surface a complex of an HLA antigen and the peptide of any one of [1] to [3];
  (b) co-culturing a CD8-positive T cell(s) with an exosome(s) that presents on its surface a complex of an HLA antigen and the peptide of any one of [1] to [3]; and
  (c) introducing into a CD8-positive T cell(s) a polynucleotide encoding each subunit of a T cell receptor (TCR) capable of binding to the peptide of any one of [1] to [3] presented by an HLA antigen on a cell surface.
[14] An APC that presents on its surface a complex of an HLA antigen and the peptide of any one of [1] to [3].
[15] The APC of [14], which is induced by the method of [12].
[16] A CTL that targets the peptide of any one of [1] to [3].
[17] The CTL of [16], which is induced by the method of [13].
[18] A method of inducing an immune response against cancer, which comprises administering to a subject at least one ingredient selected from the group consisting of (a) to (e) below:
  (a) one or more types of peptides of any one of [1] to [3];
  (b) one or more types of polynucleotides encoding the peptide(s) of any one of [1] to [3] in an expressible form;
  (c) an antigen-presenting cell (APC) that presents on its cell surface a complex of the peptide of any one of [1] to [3] and an HLA antigen;
  (d) an exosome that presents on its cell surface a complex of the peptide of any one of [1] to [3] and an HLA antigen; and
  (e) a CTL that targets the peptide of any one of [1] to [3].
[19] A method of treating and/or preventing cancer, and/or preventing postoperative recurrence thereof, which comprises administering to a subject at least one ingredient selected from the group consisting of (a) to (e) below:
  (a) one or more types of peptides of any one of [1] to [3];
  (b) one or more types of polynucleotides encoding the peptide(s) of any one of [1] to [3] in an expressible form;
  (c) an antigen-presenting cell (APC) that presents on its cell surface a complex of the peptide of any one of [1] to [3] and an HLA antigen;
  (d) an exosome that presents on its cell surface a complex of the peptide of any one of [1] to [3] and an HLA antigen; and
  (e) a CTL that targets the peptide of any one of [1] to [3].
[20] An antibody that binds to the peptide of any one of [1] to [3].
[21] A method of screening for a peptide having CTL-inducing ability, which comprises the steps of:
  (a) generating candidate sequences consisting of an amino acid sequence in which one, two or several amino acid residues are substituted, deleted, inserted and/or added to an original amino acid sequence consisting of the amino acid sequence selected from the group consisting of SEQ ID NOs: 5, 28, 30, 32, 61, 62, 63, 64, 67, 74, 77, 52, 79, 80, 85, 27, 86, 87, 90, 92, 46, 95 and 41;
  (b) selecting from among the candidate sequences generated in (a), a candidate sequence that does not have significant homology (sequence identity) with any known human gene product other than KOC1;
  (c) contacting an APC(s) with a peptide consisting of the candidate sequence selected in (b);
  (d) contacting the APC(s) of (c) with a CD8-positive T cell(s); and
  (e) selecting a peptide having an equal to or higher CTL-inducing ability than that of a peptide consisting of the original amino acid sequence.
[22] Use of at least one ingredient selected from the group consisting of (a) to (e) below in the manufacture of a composition for inducing an immune response against cancer:
  (a) one or more types of peptides of any one of [1] to [3];
  (b) one or more types of polynucleotides encoding the peptide(s) of any one of [1] to [3] in an expressible form;
  (c) an antigen-presenting cell (APC) that presents on its cell surface a complex of the peptide of any one of [1] to [3] and an HLA antigen;
  (d) an exosome that presents on its cell surface a complex of the peptide of any one of [1] to [3] and an HLA antigen; and
  (e) a CTL that targets the peptide of any one of [1] to [3].
[23] Use of at least one ingredient selected from the group consisting of (a) to (e) below in the manufacture of a pharmaceutical composition for treating and/or preventing cancer, and/or preventing postoperative recurrence thereof:

(a) one or more types of peptides of any one of [1] to [3];
(b) one or more types of polynucleotides encoding the peptide(s) of any one of [1] to [3] in an expressible form;
(c) an antigen-presenting cell (APC) that presents on its cell surface a complex of the peptide of any one of [1] to [3] and an HLA antigen;
(d) an exosome that presents on its cell surface a complex of the peptide of any one of [1] to [3] and an HLA antigen; and
(e) a CTL that targets the peptide of any one of [1] to [3].

[24] Use of at least one ingredient selected from the group consisting of (a) to (e) below for inducing an immune response against cancer:
(a) one or more types of peptides of any one of [1] to [3];
(b) one or more types of polynucleotides encoding the peptide(s) of any one of [1] to [3] in an expressible form;
(c) an antigen-presenting cell (APC) that presents on its cell surface a complex of the peptide of any one of [1] to [3] and an HLA antigen;
(d) an exosome that presents on its cell surface a complex of the peptide of any one of [1] to [3] and an HLA antigen; and
(e) a CTL that targets the peptide of any one of [1] to [3].

[25] Use of at least one ingredient selected from the group consisting of (a) to (e) below for treating and/or preventing cancer and/or preventing postoperative recurrence thereof:
(a) one or more types of peptides of any one of [1] to [3];
(b) one or more types of polynucleotides encoding the peptide(s) of any one of [1] to [3] in an expressible form;
(c) an antigen-presenting cell (APC) that presents on its cell surface a complex of the peptide of any one of [1] to [3] and an HLA antigen;
(d) an exosome that presents on its cell surface a complex of the peptide of any one of [1] to [3] and an HLA antigen; and
(e) a CTL that targets the peptide of any one of [1] to [3].

[26] A method of inducing cytotoxic activity against a KOC1-expressing cell(s), which comprises a step of administering to a subject at least one ingredient selected from the group consisting of (a) to (e) below:
(a) one or more types of peptides of any one of [1] to [3];
(b) one or more types of polynucleotides encoding the peptide(s) of any one of [1] to [3] in an expressible form;
(c) an antigen-presenting cell (APC) that presents on its cell surface a complex of the peptide of any one of [1] to [3] and an HLA antigen;
(d) an exosome that presents on its cell surface a complex of the peptide of any one of [1] to [3] and an HLA antigen; and
(e) a CTL that targets the peptide of any one of [1] to [3].

[27] A freeze-dried formulation comprising one or more types of peptides of any one of [1] to [3].

[28] A pharmaceutical composition, which is prepared by a method that comprises dissolving one or more types of peptides of any one of [1] to [3] in a water-soluble carrier, and performing filtration sterilization.

[29] A filtration-sterilized aqueous solution, which is an aqueous solution that comprises one or more types of peptides of any one of [1] to [3] and a water-soluble carrier.

[30] An emulsion comprising one or more types of peptides of any one of [1] to [3], a water-soluble carrier and an oil adjuvant.

[31] A kit comprising a container that houses the pharmaceutical composition of any one of [7] to [11] and a container that houses an adjuvant.

[32] A kit comprising a container that stores a freeze-dried formulation comprising the peptide of any one of [1] to [3], a container that stores an adjuvant, and a container that stores a re-dissolving solution the freeze-dried formulation.

The present invention is explained herein in detail with reference to its specific embodiments. However, it should be understood that the above explanation is in fact an illustrative and explanatory explanation, and is intended to explain the present invention and preferred embodiments thereof. Through routine experimentation, one skilled in the art will readily recognize that various changes and modifications can be made therein without departing from the spirit and scope of the present invention. Thus, the present invention is not confined to the above explanation, but is intended to be defined by the appended claims and equivalents thereto.

Hereinbelow, the present invention is described in more detail with reference to the Examples. Nevertheless, while the following materials, method and Examples may serve to assist one of ordinary skill in making and using certain embodiments of the present invention, there are only intended to illustrate aspects of the present invention and thus in no way to limit the scope of the present invention. One of ordinary skill in the art can use methods and materials similar or equivalent to those described herein in the practice or testing of the present invention.

All prior art documents cited herein are incorporated by reference in the present specification.

EXAMPLES

Example 1

Materials and Methods
Cell Lines
C1R, an HLA-A- and HLA-B-negative human B lymphoblastoid cell line, and COST, an African green monkey kidney cell line, were purchased from ATCC.

Generation of Stimulator Cells with Stable HLA-A*1101 Expression
C1R (C1R-A11) that stably expresses HLA-A*1101 was used as a stimulator cell. A cDNA encoding the open-reading frame of HLA-A*1101 was amplified by PCR and cloned into an expression vector. C1R cells were transfected with the expression vector, and then selected using G418 (Invitrogen) for two weeks. The G418-selected cells were seeded into wells containing G418-added culture medium in a 96-well plate, and further cultured for 30 days. The exogenous HLA-A*1101 expression in C1R cells was verified by flow cytometric analysis.

Selection of Candidate KOC1-Derived Peptides
KOC1-derived 9mer and 10mer peptides that bind to the HLA-A*1101 molecule were predicted using the binding prediction server "NetMHC 3.2" (www.cbs.dtu.dk/services/NetMHC/) (Buus et al., Tissue Antigens. 2003 November, 62(5): 378-84; Nielsen et al., Protein Sci. 2003 May, 12(5): 1007-17; Bioinformatics. 2004 Jun. 12: 20(9): 1388-97).

Peptide Synthesis
The peptides were synthesized by Biosynthesis (Lewisville, Tex.) according to a standard solid-phase synthesis method, and purified by reversed phase high-performance liquid chromatography (HPLC). The peptides were analyzed for their purity (>90%) and identity by analytical HPLC and mass spectrometry, respectively. The peptides were dissolved in dimethylsulfoxide at 20 mg/ml and stored at −80 degrees C.

In Vitro CTL Induction

Monocyte-derived dendritic cells (DCs) were used as the antigen-presenting cell to induce a cytotoxic T lymphocyte (CTL) response against peptides presented on human leukocyte antigens (HLAs). As described in the other sections, DCs were generated in vitro (Nakahara S et al., Cancer Res 2003, 63(14): 4112-8). Specifically, peripheral-blood mononuclear cells isolated from healthy volunteers (HLA-A*1101-positive) with the Ficoll-Paque plus solution (Pharmacia) were separated by attaching to plastic tissue culture dishes (Becton Dickinson) and concentrated as a monocyte fraction. The monocyte-concentrated population was cultured in the presence of 1000 IU/ml granulocyte macrophage colony-stimulating factor (R&D System) and 1000 IU/ml interleukin(IL)-4 (R&D System) in an AIM-V medium (Invitrogen) containing 2% heat-inactivated autologous serum (AS). After seven days of culturing, the cytokine-induced DCs were pulsed with 20 micro-g/ml each of the synthesized peptides in an AIM-V medium at 37 degrees C. for three hours in the presence of 3 micro-g/ml beta 2-microglobulin. The generated cells appeared to express on their cell surface DC-associated molecules such as CD80, CD83, CD86 and HLA class II (data not shown). Next, these peptide-pulsed DCs were inactivated by X-ray irradiation (20 Gy), and mixed in a 1:20 ratio with autologous CD8+ T cells obtained by positive selection using the CD8 Positive Isolation Kit (Dynal). These culture products were seeded in a 48-well plate (Corning). Each well was made to contain $1.5 \times 10^4$ peptide-pulsed DCs, $3 \times 10^5$ CD8+ T cells and 10 ng/ml IL-7 (R&D System) in 0.5 ml of the AIM-V/2% AS medium. Three days later, these culture products were added with a final concentration of 20 IU/ml IL-2 (CHIRON). On day 7 and day 14, T cells were further stimulated with peptide-pulsed autologous DCs. The DCs were prepared every time by the same method as above. On day 21, after the third peptide stimulation, CTLs were examined against the peptide-pulsed C1R-A11 by a human interferon (IFN)-gamma enzyme-linked immunospot (ELISPOT) assay (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

CTL Propagation Procedure

CTLs were propagated in culture using methods similar to those disclosed by Riddell et al. (Walter E A et al., N Engl J Med 1995, 333(16): 1038-44; Riddell S R et al., Nat Med 1996, 2(2): 216-23). The CTLs were co-cultured in a total of 25 ml AIM-V medium containing 5% AS (AIM-V/5% AS) and 40 ng/ml anti-CD3 antibody with two types of Mitomycin C-treated human B lymphoblastoid cell lines at $5 \times 10^6$ cells/flask. One day after beginning of the culturing, 120 IU/ml IL-2 was added to the culture. On days 5, 8 and 11, a fresh AIM-V/5% AS medium containing 30 IU/ml IL-2 was added to the culture (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Establishment of CTL Clones

Dilution of CTLs was carried out to make 0.3, 1 and 3 cells/well in 96 round-bottomed microtiter plates (Nalge Nunc International). The CTLs were co-cultured with two types of Mitomycin C-treated human B lymphoblastoid cell lines at $1 \times 10^4$ cells/well in a total of 150 micro-l/well AIM-V/5% AS medium with 30 ng/ml anti-CD3 antibody and 125 IU/ml IL-2. Ten days later, IL-2 was added to the medium at 50 micro-l/well to reach a final concentration of 125 IU/ml. On day 14, the CTL activity was tested, and the CTL clones were propagated using the same method as described above (Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Specific CTL Activity

To examine specific CTL activity, an IFN-gamma ELISPOT assay and an IFN-gamma enzyme-linked immunosorbent assay (ELISA) were performed. Specifically, peptide-pulsed C1R-A11 ($1 \times 10^4$ cells/well) was prepared as the stimulator cell. The induced CTLs, i.e., CTL lines and CTL clones, were used as the responder cell. The IFN-gamma ELISPOT assay and IFN-gamma ELISA were performed according to the manufacturer's manual.

Establishment of Target Cells Forcibly Expressing a Target Gene and HLA-A*1101

A cDNA encoding the open-reading frame of a target gene or HLA-A*1101 was amplified by PCR. The PCR-amplified product was cloned into an expression vector. Either or both of the target gene-expressing vector and the HLA-A*1101-expressing vector were transfected into COST, which is a cell line negative for the target gene and HLA, using Lipofectamine 2000 (Invitrogen) following the manufacturer's recommended protocol. Two days after transfection, the transfected cells were harvested using versene (Invitrogen), and used as the target cell for CTL activity assay ($5 \times 10^4$ cells/well).

Results

Prediction of KOC1-Derived HLA-A*1101-Binding Peptides

Tables 1a and 1b show KOC1-derived 9mer peptides and 10mer peptides that have been predicted to bind to HLA-A*1101 in the descending order of binding affinity. A total of 60 peptides that potentially have an HLA-A*1101-binding ability was selected and investigated to determine epitope peptides.

TABLE 1a

HLA-A11-binding 9mer peptides derived from KOC1

| Start position | Amino acid sequence | Kd (nM) | SEQ ID NO |
|---|---|---|---|
| 258 | KSILEIMHK | 16 | 1 |
| 121 | VVNVTYSSK | 18 | 2 |
| 465 | KAQGRIYGK | 32 | 3 |
| 517 | SSAEVVVPR | 45 | 4 |
| 415 | LSVGAIIGK | 76 | 5 |
| 28 | PVSGPFLVK | 85 | 6 |
| 52 | KAIEALSGK | 92 | 7 |
| 142 | FQLENFTLK | 150 | 8 |
| 215 | GATIRNITK | 293 | 9 |
| 338 | KAEEEIMKK | 297 | 10 |
| 497 | FAAGRVIGK | 405 | 11 |
| 15 | PSDLESIFK | 451 | 12 |

TABLE 1a-continued

HLA-A11-binding 9mer peptides derived from KOC1

| Start position | Amino acid sequence | Kd (nM) | SEQ ID NO |
|---|---|---|---|
| 536 | VVKITGHFY | 757 | 13 |
| 479 | FVSPKEEVK | 791 | 14 |
| 493 | RVPSFAAGR | 1100 | 15 |
| 272 | KFTEEIPLK | 1108 | 16 |
| 226 | QSKIDVHRK | 1125 | 17 |
| 330 | KGNVETCAK | 1835 | 18 |
| 544 | YACQVAQRK | 1841 | 19 |
| 220 | NITKQTQSK | 2617 | 20 |
| 301 | KIEQDTDTK | 2631 | 21 |
| 553 | IQEILTQVK | 3008 | 22 |
| 182 | QGSPGSVSK | 3293 | 23 |
| 559 | QVKQHQQQK | 3313 | 24 |
| 58 | SGKIELHGK | 4377 | 25 |
| 205 | QFVGAIIGK | 4472 | 26 |

TABLE 1b

HLA-A11-binding 10mer peptides derived from KOC1

| Start position | Amino acid sequence | Kd (nM) | SEQ ID NO |
|---|---|---|---|
| 120 | AVVNVTYSSK | 13 | 27 |
| 414 | ALSVGAIIGK | 33 | 28 |
| 456 | ITGPPEAQFK | 73 | 29 |
| 204 | TQFVGAIIGK | 86 | 30 |
| 73 | SVPKRQRIRK | 103 | 31 |
| 14 | APSDLESIFK | 152 | 32 |
| 183 | GSPGSVSKQK | 165 | 33 |
| 496 | SFAAGRVIGK | 168 | 34 |
| 516 | LSSAEVVVPR | 169 | 35 |
| 552 | KIQEILTQVK | 214 | 36 |
| 431 | LSRFAGASIK | 342 | 37 |
| 181 | RQGSPGSVSK | 368 | 38 |
| 124 | VTYSSKDQAR | 437 | 39 |
| 225 | TQSKIDVHRK | 478 | 40 |
| 535 | VVVKITGHFY | 678 | 41 |
| 224 | QTQSKIDVHR | 711 | 42 |
| 57 | LSGKIELHGK | 904 | 43 |
| 141 | GFQLENFTLK | 911 | 44 |
| 568 | ALQSGPPQSR | 1065 | 45 |

TABLE 1b-continued

HLA-A11-binding 10mer peptides derived from KOC1

| Start position | Amino acid sequence | Kd (nM) | SEQ ID NO |
|---|---|---|---|
| 312 | ISPLQELTLY | 1262 | 46 |
| 441 | IAPAEAPDAK | 1570 | 47 |
| 27 | IPVSGPFLVK | 1622 | 48 |
| 570 | QSGPPQSRRK | 1777 | 49 |
| 95 | EVLDSLLVQY | 2124 | 50 |
| 336 | CAKAEEEIMK | 2194 | 51 |
| 281 | ILAHNNFVGR | 2264 | 52 |
| 466 | AQGRIYGKIK | 2595 | 53 |
| 160 | AQQNPLQQPR | 2689 | 54 |
| 420 | IIGKQGQHIK | 2763 | 55 |
| 558 | TQVKQHQQQK | 2862 | 56 |
| 257 | CKSILEIMHK | 3467 | 57 |
| 291 | LIGKEGRNLK | 3795 | 58 |
| 263 | IMHKEAQDIK | 4083 | 59 |
| 569 | LQSGPPQSRR | 4107 | 60 |

Start position indicates the number of amino acid residue from the N-terminus of KOC1. The dissociation constant [Kd (nM)] is derived from "NetMHC3.2".

Induction of CTLs by the Predicted KOC1-Derived HLA-A*1101-Restricted Peptides

CTLs against the KOC1-derived peptides were generated according to the protocol described in "Materials and methods". The peptide-specific CTL activity was measured by an IFN-gamma ELISPOT assay (FIG. 1). In comparison with the control, CTLs in Well #6 with KOC1-A11-9-415 (SEQ ID NO: 5) (a), Well #4 with KOC1-A11-10-414 (SEQ ID NO: 28) (b), Well #5 with KOC1-A11-10-204 (SEQ ID NO: 30) (c), and Well #8 with KOC1-A11-10-14 (SEQ 1D NO: 32) (d) showed potent IFN-gamma production. Meanwhile, despite that other peptides shown in Tables 1a and 1b potentially have an HLA-A*1101-binding activity, specific CTL activity was not detected as a result of stimulation by those peptides. An example of typical negative data is that specific IFN-gamma production was not observed from CTLs stimulated with KOC1-A11-9-258 (SEQ ID NO: 1) (e). As a result, four types of KOC1-derived peptides were selected as peptides capable of inducing potent CTLs.

Figure 2:
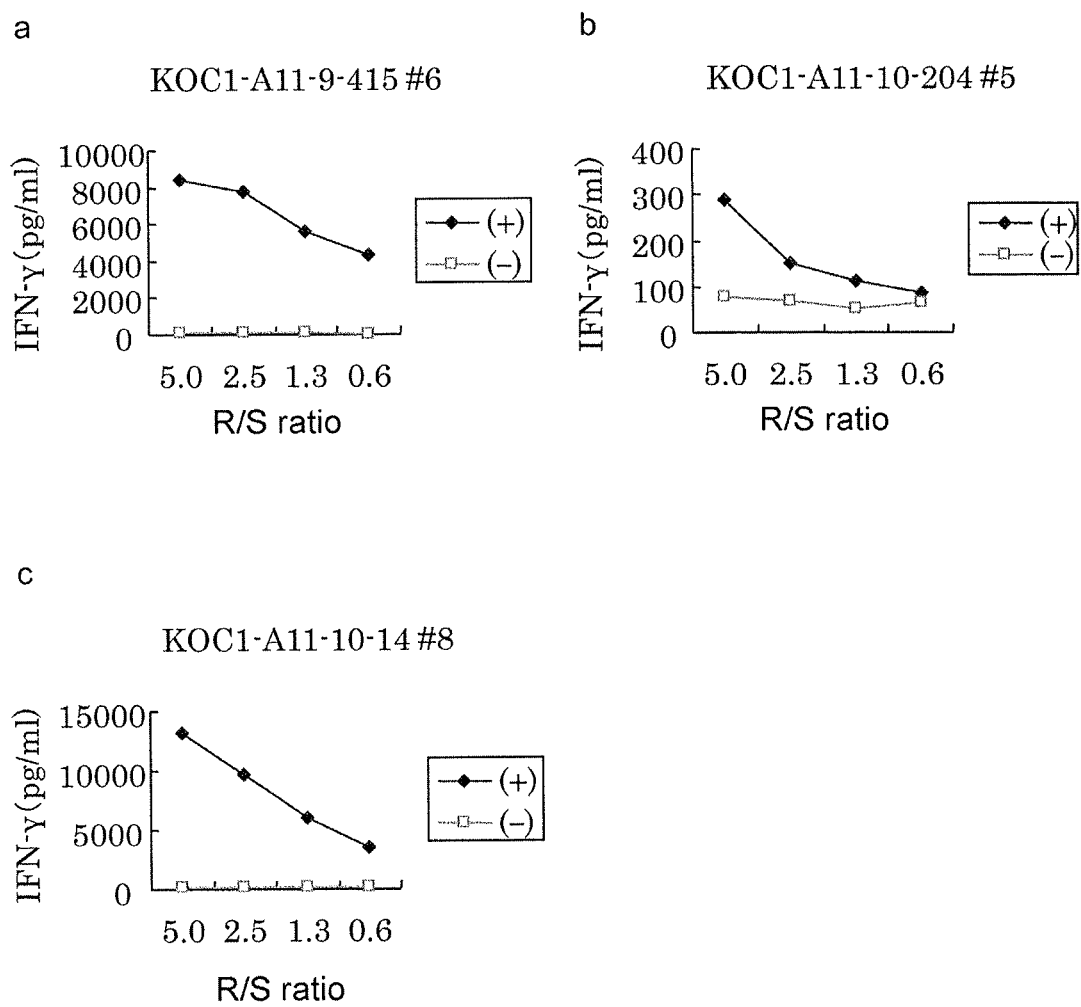
FIG. 2 consists of a series of line graphs (a) to (c) showing results of an IFN-gamma enzyme-linked immunosorbent assay (ELISA), confirming IFN-gamma production in CTL lines stimulated with KOC1-A11-9-415 (SEQ ID NO: 5) (a), KOC1-A11-10-204 (SEQ ID NO: 30) (b) or KOC1-A11-10-14 (SEQ ID NO: 32) (c). These results prove that the CTL lines established by stimulation with each of the peptides showed potent IFN-gamma production in comparison with the control. In the figure, "+" shows IFN-gamma production against target cells pulsed with an appropriate peptide; and "−" shows IFN-gamma production against target cells that have not been pulsed with any peptides. The R/S ratio indicates the ratio of the cell number of CTL line (Responder cells) and the cell number of target cells (Stimulator cells).
Figure 3:
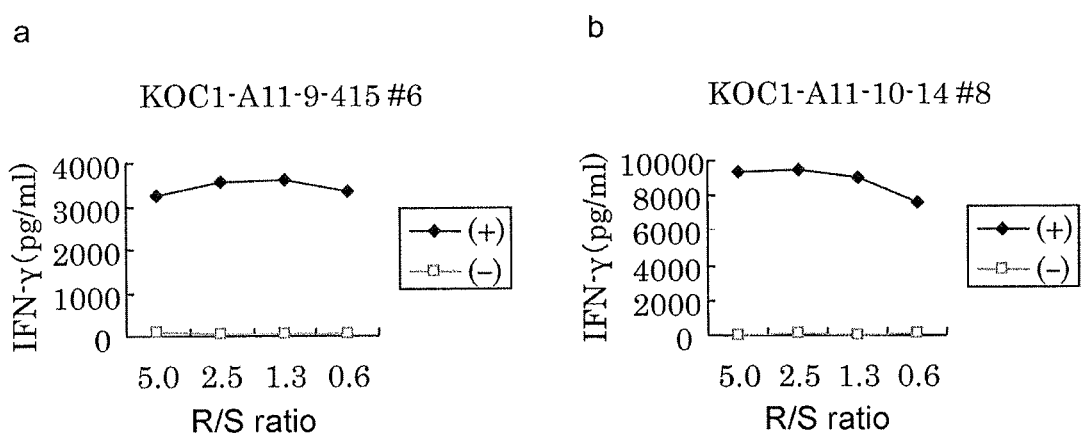
FIG. 3 consists of line graphs (a) and (b) showing IFN-gamma production in CTL clones established by limiting dilution from CTL lines stimulated with KOC1-A11-9-415 (SEQ ID NO: 5) or KOC1-A11-10-14 (SEQ ID NO: 32). These results prove that the CTL clones established by stimulation with each of the peptides showed potent IFN-gamma production in comparison with the control. In the figure, "+" shows IFN-gamma production against target cells pulsed with an appropriate peptide; and "−" shows IFN-gamma production against target cells that have not been pulsed with any peptides. The R/S ratio indicates the ratio of the cell number of CTL clone (Responder cells) and the cell number of target cells (Stimulator cells).

Establishment of CTL Lines and Clones Against the KOC1-Derived HLA-A*1101-Restricted Peptides CTL lines were established by propagating CTLs in Well #6 with KOC1-A11-9-415 (SEQ ID NO: 5) (a), Well #5 with KOC1-A11-10-204 (SEQ ID NO: 30) (b), and Well #8 with KOC1-A11-10-14 (SEQ ID NO: 32) (c), which showed peptide-specific CTL activity in the IFN-gamma ELISPOT assay. The CTL activity of these CTL lines was measured by IFN-gamma ELISA (FIG. 2). These CTL lines showed potent IFN-gamma production against target cells pulsed with the respective peptides, in comparison with target cells that have not been pulsed with the peptides. Further, CTL clones were established from the CTL lines by limiting dilution as described in the "Materials and methods" section above, and IFN-gamma production from the CTL clones against peptide-pulsed C1R-A11 was measured by IFN-gamma ELISA. Potent IFN-gamma production was observed in CTL clones stimulated with KOC1-A11-9-415 (SEQ ID NO: 5) (a) and KOC1-A11-10-14 (SEQ ID NO: 32) (b) (FIG. 3).

Specific CTL Activity Against Target Cells Expressing KOC1 and HLA-A*1101

Figure 4:
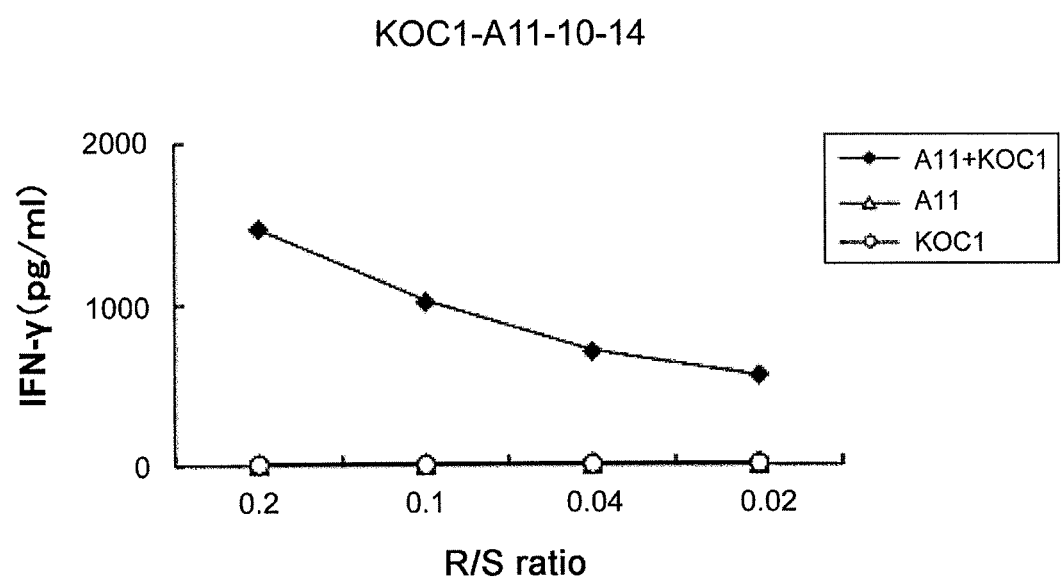
FIG. 4 is a line graph showing specific CTL activity against target cells expressing both KOC1 and HLA-A*1101. COS7 cells transfected with either HLA-A*1101 or the full-length KOC1 gene were prepared as the control. The CTL clone established using KOC1-A11-10-14 (SEQ ID NO: 32) demonstrated a specific CTL activity against COS7 cells transfected with both KOC1 and HLA-A*1101 (black diamond). On the other hand, a significant specific CTL activity was not shown against target cells transfected with either one of HLA-A*1101 (white triangle) and KOC1 (white circle).

The CTL clone established against KOC1-A11-10-14 (SEQ ID NO: 32) was investigated for its ability to recognize target cells expressing KOC1 and the HLA-A*1101 molecule. COS7 cells transfected with both full-length KOC1 and the HLA-A*1101 gene (a specific model of target cells expressing KOC1 and the HLA-A*1101 gene) were prepared as the target cell. COS7 cells transfected with either full-length KOC1 or HLA-A*1101 were prepared as the control. The KOC1-A11-10-14 (SEQ ID NO: 32)-stimulated CTL clone demonstrated a potent CTL activity against COS7 cells expressing both KOC1 and HLA-A*1101 (FIG. 4). On the other hand, a significant specific CTL activity was not detected against the control cells. These data clearly proved that KOC1-A11-10-14 (SEQ ID NO: 32) is a peptide generated from endogenous processing of KOC1, and is presented on target cells with the HLA-A*1101 molecule and recognized by CTLs. These results demonstrated the possibility that KOC1-A11-10-14 (SEQ ID NO: 32) may be suitable as a cancer vaccine for patients having a KOC1-expressing cancer.

Homology Analysis of Antigen Peptides

CTLs stimulated with KOC1-A11-9-415 (SEQ ID NO: 5), KOC1-A11-10-414 (SEQ ID NO: 28), KOC1-A11-10-204 (SEQ ID NO: 30), or KOC1-A11-10-14 (SEQ ID NO: 32) demonstrated a significant specific CTL activity. These results may be due to the fact that the KOC1-A11-9-415 (SEQ ID NO: 5), KOC1-A11-10-414 (SEQ ID NO: 28), KOC1-A11-10-204 (SEQ ID NO: 30), and KOC1-A11-10-14 (SEQ ID NO: 32) sequences are homologous to peptides derived from other molecules known for sensitizing the human immune system. In order to exclude this possibility, homology analysis was performed by querying these peptide sequences using the BLAST algorithm (blast.ncbi.nlm.nih.gov/Blast.cgi). This result showed that there is no sequence having a significant homology with the KOC1-A11-9-415 (SEQ ID NO: 5), KOC1-A11-10-414 (SEQ ID NO: 28), KOC1-A11-10-204 (SEQ ID NO: 30), and KOC1-A11-10-14 (SEQ ID NO: 32) sequences. On the other hand, KOC1-A11-10-204 (SEQ ID NO: 30) is identical to a peptide sequence identified in IMP-2 which is another IMP family. It has been previously reported that IMP-2 is not expressed in normal organs except testis and fetal liver (Hammer N A et al., Reproduction. 2005; 130(2): 203-12). It is involved in the proliferation of glioblastoma cancer stem cells (Janiszewska M et al., Genes Dev. 2012; 26(17): 1926-44). IMP-2 is promising as a target antigen for cancer immunotherapy. Therefore, to the knowledge of the present inventors, there is almost no possibility that these peptides would elicit an unintended immune response against other unrelated molecules. In conclusion, novel KOC1-derived HLA-A11-restricted epitope peptides were identified. It was demonstrated that the KOC1-derived epitope peptides are applicable for cancer immunotherapy.

Example 2

Materials and Methods
Cell Lines

C1R, an HLA-A- and HLA-B-negative human B lymphoblastoid cell line, and COS7, an African green monkey kidney cell line, were purchased from ATCC.

Generation of Stimulator Cells with Stable HLA-A*3303 Expression

C1R (C1R-A33) that stably expresses HLA-A*3303 was used as a stimulator cell. A cDNA encoding the open-reading frame of HLA-A*3303 was amplified by PCR and cloned into an expression vector. C1R cells were transfected with the expression vector, and then selected using G418 (Invitrogen) for two weeks. The G418-selected cells were seeded into wells containing G418-added culture medium in a 96-well plate, and further cultured for 30 days. The exogenous HLA-A*3303 expression in C1R cells was verified by flow cytometric analysis.

Selection of Candidate KOC1-Derived Peptides

KOC1-derived 9mer and 10mer peptides that bind to the HLA-A*3303 molecule were predicted using the binding prediction server "NetMHCpan2.8" (www.cbs.dtu.dk/services/NetMHCpan/) (Nielsen et al., PLoS One. 2007; 29; 2(8): e796; Hoof et al., Immunogenetics. 2009; 61(1): 1-13).

Peptide Synthesis

These peptides were synthesized by Biosynthesis (Lewisville, Tex.) according to a standard solid-phase synthesis method, and purified by reversed phase high-performance liquid chromatography (HPLC). The peptides were analyzed for their purity (>90%) and identity by analytical HPLC and mass spectrometry, respectively. The peptides were dissolved in dimethylsulfoxide at 20 mg/ml and stored at −80 degrees C.

In Vitro CTL Induction

Monocyte-derived dendritic cells (DCs) were used as the antigen-presenting cell to induce a cytotoxic T lymphocyte (CTL) response against peptides presented on human leukocyte antigens (HLAs). As described in the other sections, DCs were generated in vitro (Nakahara S et al., Cancer Res 2003, 63(14): 4112-8). Specifically, peripheral-blood mononuclear cells isolated from healthy volunteers (HLA-A*3303-positive) with the Ficoll-Paque plus solution (Pharmacia) were separated by attaching to plastic tissue culture dishes (Becton Dickinson) and concentrated as a monocyte fraction. The monocyte-concentrated population was cultured in the presence of 1000 IU/ml granulocyte macrophage colony-stimulating factor (R&D System) and 1000 IU/ml interleukin(IL)-4 (R&D System) in an AIM-V medium (Invitrogen) containing 2% heat-inactivated autologous serum (AS). After seven days of culturing, the cytokine-induced DCs were pulsed with 20 micro-g/ml each of the synthesized peptides in an AIM-V medium at 37 degrees C. for three hours in the presence of 3 micro-g/ml beta 2-microglobulin. The generated cells appeared to express on their cell surface DC-associated molecules such as CD80, CD83, CD86 and HLA class II (data not shown). Next, these peptide-pulsed DCs were inactivated by X-ray irradiation (20 Gy), and mixed in a 1:20 ratio with autologous CD8$^+$ T cells obtained by positive selection using the CD8 Positive Isolation Kit (Dynal). These culture products were seeded in a 48-well plate (Corning). Each well was made to contain 1.5×10$^4$ peptide-pulsed DCs, 3×10$^5$ CD8$^+$ T cells and 10 ng/ml IL-7 (R&D System) in 0.5 ml of the AIM-V/2% AS medium. Three days later, these culture products were added with a final concentration of 20 IU/ml IL-2 (CHIRON). On day 7 and day 14, T cells were further stimulated with peptide-pulsed autologous DCs. The DCs were prepared every time by the same method as above. On day 21, after the third peptide stimulation, CTLs were examined against the peptide-pulsed C1R-A33 cell by a human interferon (IFN)-gamma enzyme-linked immunospot (ELISPOT) assay (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

CTL Propagation Procedure

CTLs were propagated in culture using methods similar to those disclosed by Riddell et al. (Walter E A et al., N Engl J Med 1995, 333(16): 1038-44; Riddell S R et al., Nat Med 1996, 2(2): 216-23). The CTLs were co-cultured in a total of 25 ml AIM-V medium containing 5% AS (AIM-V/5% AS) and 40 ng/ml anti-CD3 antibody with two types of Mitomycin C-treated human B lymphoblastoid cell lines at $5 \times 10^6$ cells/flask. One day after beginning of the culturing, 120 IU/ml IL-2 was added to the culture. On days 5, 8 and 11, a fresh AIM-V/5% AS medium containing 30 IU/ml IL-2 was added to the culture (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Establishment of CTL Clones

Dilution of CTLs was carried out to make 0.3, 1 and 3 cells/well in 96 round-bottomed microtiter plates (Nalge Nunc International). The CTLs were co-cultured with two types of Mitomycin C-treated human B lymphoblastoid cell lines at $1 \times 10^4$ cells/well in a total of 150 micro-l/well AIM-V/5% AS medium with 30 ng/ml anti-CD3 antibody and 125 IU/ml IL-2. Ten days later, IL-2 was added to the medium at 50 micro-l/well to reach a final concentration of 125 IU/ml. On day 14, the CTL activity was tested, and the CTL clones were propagated using the same method as described above (Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Specific CTL Activity

To examine specific CTL activity, an IFN-gamma ELISPOT assay and an IFN-gamma enzyme-linked immunosorbent assay (ELISA) were performed. Specifically, peptide-pulsed C1R-A33 ($1 \times 10^4$ cells/well) was prepared as the stimulator cell. The induced CTLs, i.e., CTL lines and CTL clones, were used as the responder cell. The IFN-gamma ELISPOT assay and IFN-gamma ELISA were performed according to the manufacturer's manual.

Establishment of Target Cells Forcibly Expressing a Target Gene and HLA-A*3303

A cDNA encoding the open-reading frame of a target gene or HLA-A*3303 was amplified by PCR. The PCR-amplified product was cloned into an expression vector. Either or both of the target gene-expressing vector and the HLA-A*3303-expressing vector were transfected into COST, which is a cell line negative for the target gene and HLA, using Lipofectamine 2000 (Invitrogen) following the manufacturer's recommended protocol. Two days after transfection, the transfected cells were harvested using versene (Invitrogen), and used as the target cell for CTL activity assay ($5 \times 10^4$ cells/well).

Results

Prediction of KOC1-Derived HLA-A*3303-Binding Peptides

Tables 2a and 2b show KOC1-derived 9mer peptides and 10mer peptides that have been predicted to bind to HLA-A*3303 in the descending order of binding affinity. A total of 37 peptides that potentially have an HLA-A*3303-binding ability was selected and investigated to determine epitope peptides.

TABLE 2a

HLA-A33-binding 9mer peptides derived from KOC1

| Start position | Amino acid sequence | Kd (nM) | SEQ ID NO |
|---|---|---|---|
| 543 | FYACQVAQR | 98 | 61 |
| 517 | SSAEVVVPR | 105 | 4 |
| 282 | LAHNNFVGR | 140 | 62 |
| 493 | RVPSFAAGR | 182 | 15 |
| 317 | ELTLYNPER | 260 | 63 |
| 485 | EVKLEAHIR | 278 | 64 |
| 125 | TYSSKDQAR | 467 | 65 |
| 461 | EAQFKAQGR | 555 | 66 |
| 286 | NFVGRLIGK | 933 | 67 |
| 225 | TQSKIDVHR | 1039 | 68 |
| 69 | EVEHSVPKR | 1453 | 69 |
| 161 | QQNPLQQPR | 1485 | 70 |
| 406 | ETVHLFIPA | 2340 | 71 |
| 73 | SVPKRQRIR | 2969 | 72 |
| 570 | QSGPPQSRR | 3001 | 73 |
| 121 | VVNVTYSSK | 3272 | 2 |
| 465 | KAQGRIYGK | 3308 | 3 |
| 142 | FQLENFTLK | 4063 | 8 |
| 34 | LVKTGYAFV | 4107 | 74 |
| 211 | IGKEGATIR | 4197 | 75 |
| 307 | DTKITISPL | 4676 | 76 |

TABLE 2b

HLA-A33-binding 10mer peptides derived from KOC1

| Start position | Amino acid sequence | Kd (nM) | SEQ ID NO |
|---|---|---|---|
| 542 | HFYACQVAQR | 16 | 77 |
| 124 | VTYSSKDQAR | 201 | 39 |
| 224 | QTQSKIDVHR | 296 | 42 |
| 281 | ILAHNNFVGR | 320 | 52 |
| 72 | HSVPKRQRIR | 428 | 78 |
| 516 | LSSAEVVVPR | 467 | 35 |
| 496 | SFAAGRVIGK | 1710 | 34 |
| 543 | FYACQVAQRK | 2635 | 79 |
| 424 | QGQHIKQLSR | 2752 | 80 |

TABLE 2b-continued

HLA-A33-binding 10mer peptides derived from KOC1

| Start position | Amino acid sequence | Kd (nM) | SEQ ID NO |
|---|---|---|---|
| 190 | KQKPCDLPLR | 3492 | 81 |
| 431 | LSRFAGASIK | 3726 | 37 |
| 568 | ALQSGPPQSR | 4478 | 45 |
| 210 | IIGKEGATIR | 4831 | 82 |
| 478 | NFVSPKEEVK | 4831 | 83 |
| 77 | RQRIRKLQIR | 4883 | 84 |
| 285 | NNFVGRLIGK | 4883 | 85 |

Start position indicates the number of amino acid residue from the N-terminus of KOC1. The dissociation constant [Kd (nM)] is derived from "NetMHCpan 2.8".

Induction of CTLs by the Predicted KOC1-Derived HLA-A*3303-Restricted Peptides

Figure 5:
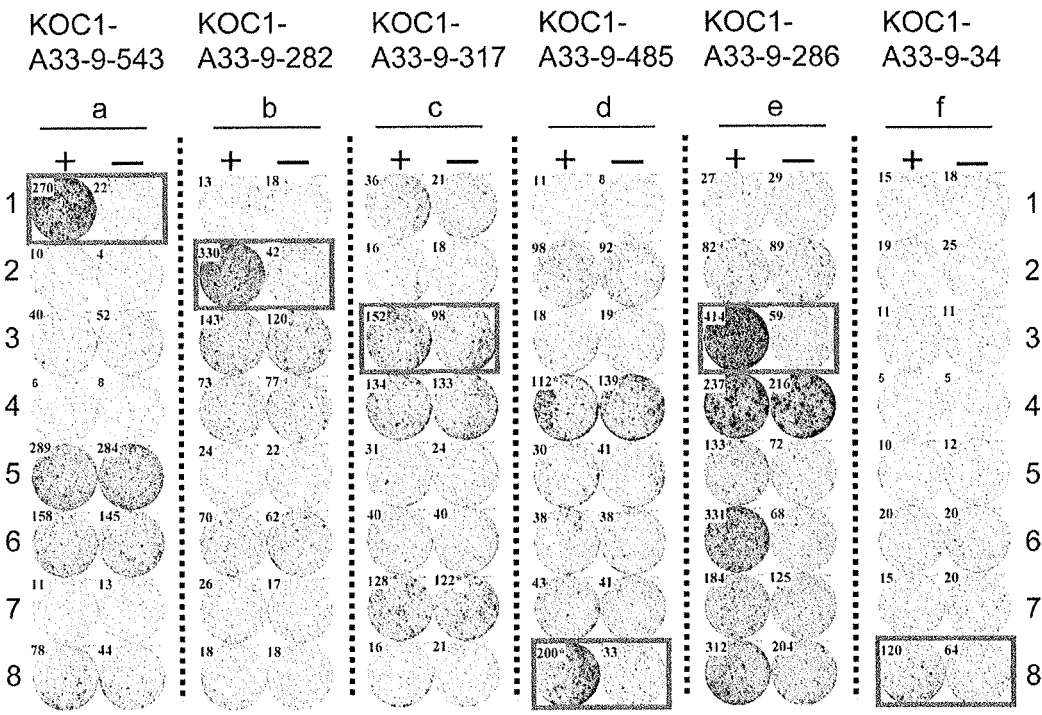
FIG. 5 consists of photos (a) to (1) showing results of an IFN-gamma ELISPOT assay in CTLs induced using peptides derived from KOC1. In comparison with the control, CTLs in Well #1 with KOC1-A33-9-543 (SEQ ID NO: 61) (a), Well #2 with KOC1-A33-9-282 (SEQ ID NO: 62) (b), Well #3 with KOC1-A33-9-317 (SEQ ID NO: 63) (c), Well #8 with KOC1-A33-9-485 (SEQ ID NO: 64) (d), Well #3 with KOC1-A33-9-286 (SEQ ID NO: 67) (e), Well #8 with KOC1-A33-9-34 (SEQ ID NO: 74) (f), Well #4 with KOC1-A33-10-542 (SEQ ID NO: 77) (g), Well #3 with KOC1-A33-10-281 (SEQ ID NO: 52) (h), Well #6 with KOC1-A33-10-543 (SEQ ID NO: 79) (i), Well #1 with KOC1-A33-10-424 (SEQ ID NO: 80) (j), and Well #5 with KOC1-A33-10-285 (SEQ ID NO: 85) (k) showed potent IFN-gamma production. In these photos, the square on the wells show that cells from the respective wells were propagated for the establishment of CTL lines. In contrast, KOC1-A33-9-517 (SEQ ID NO: 4) (1) is shown as an example of typical negative data where there was no specific IFN-gamma production. In the figure, "+" shows IFN-gamma production against target cells pulsed with an appropriate peptide; and "−" shows IFN-gamma production against target cells that have not been pulsed with any peptides.
Figure 5:
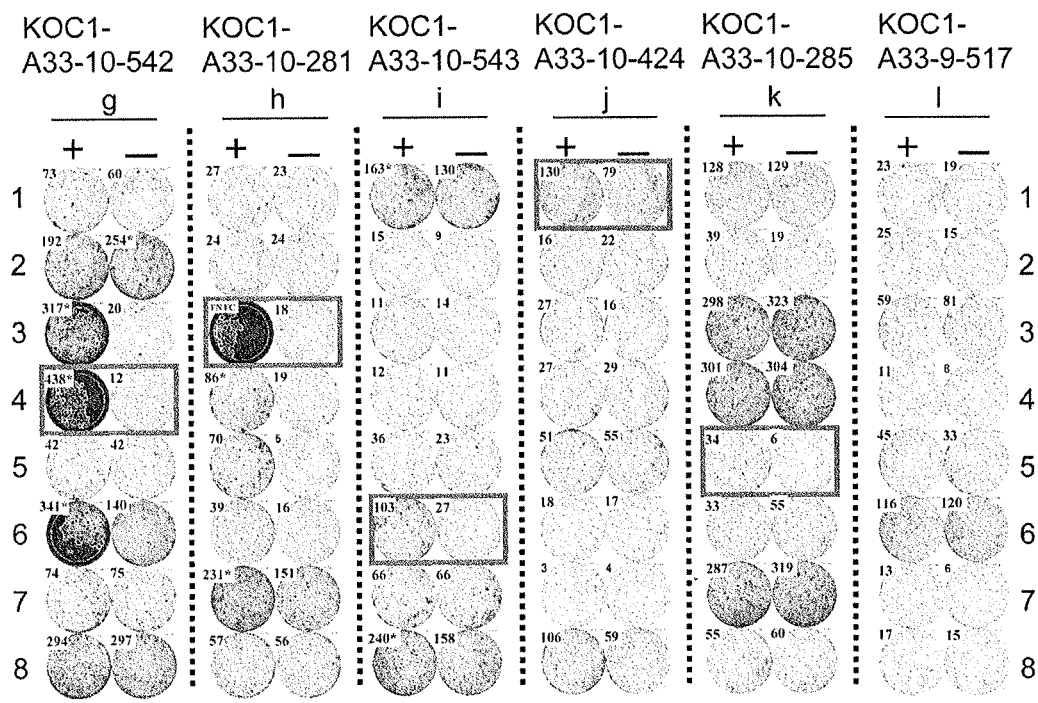

CTLs against the KOC1-derived peptides were generated according to the protocol described in "Materials and methods". The peptide-specific CTL activity was measured by an IFN-gamma ELISPOT assay (FIG. 5). In comparison with the control, CTLs in Well #1 with KOC1-A33-9-543 (SEQ ID NO: 61) (a), Well #2 with KOC1-A33-9-282 (SEQ ID NO: 62) (b), Well #3 with KOC1-A33-9-317 (SEQ ID NO: 63) (c), Well #8 with KOC1-A33-9-485 (SEQ ID NO: 64) (d), Well #3 with KOC1-A33-9-286 (SEQ ID NO: 67) (e), Well #8 with KOC1-A33-9-34 (SEQ ID NO: 74) (f), Well #4 with KOC1-A33-10-542 (SEQ ID NO: 77) (g), Well #3 with KOC1-A33-10-281 (SEQ ID NO: 52) (h), Well #6 with KOC1-A33-10-543 (SEQ ID NO: 79) (i), Well #1 with KOC1-A33-10-424 (SEQ ID NO: 80) (j), and Well #5 with KOC1-A33-10-285 (SEQ ID NO: 85) (k) showed potent IFN-gamma production. Meanwhile, despite that other peptides shown in Tables 2a and 2b potentially have an HLA-A*3303-binding activity, specific CTL activity was not detected as a result of stimulation by those peptides. An example of typical negative data is that specific IFN-gamma production was not observed from CTLs stimulated with KOC1-A33-9-517 (SEQ ID NO: 4) (l). As a result, eleven types of KOC1-derived peptides were selected as peptides capable of inducing potent CTLs.

Figure 6:
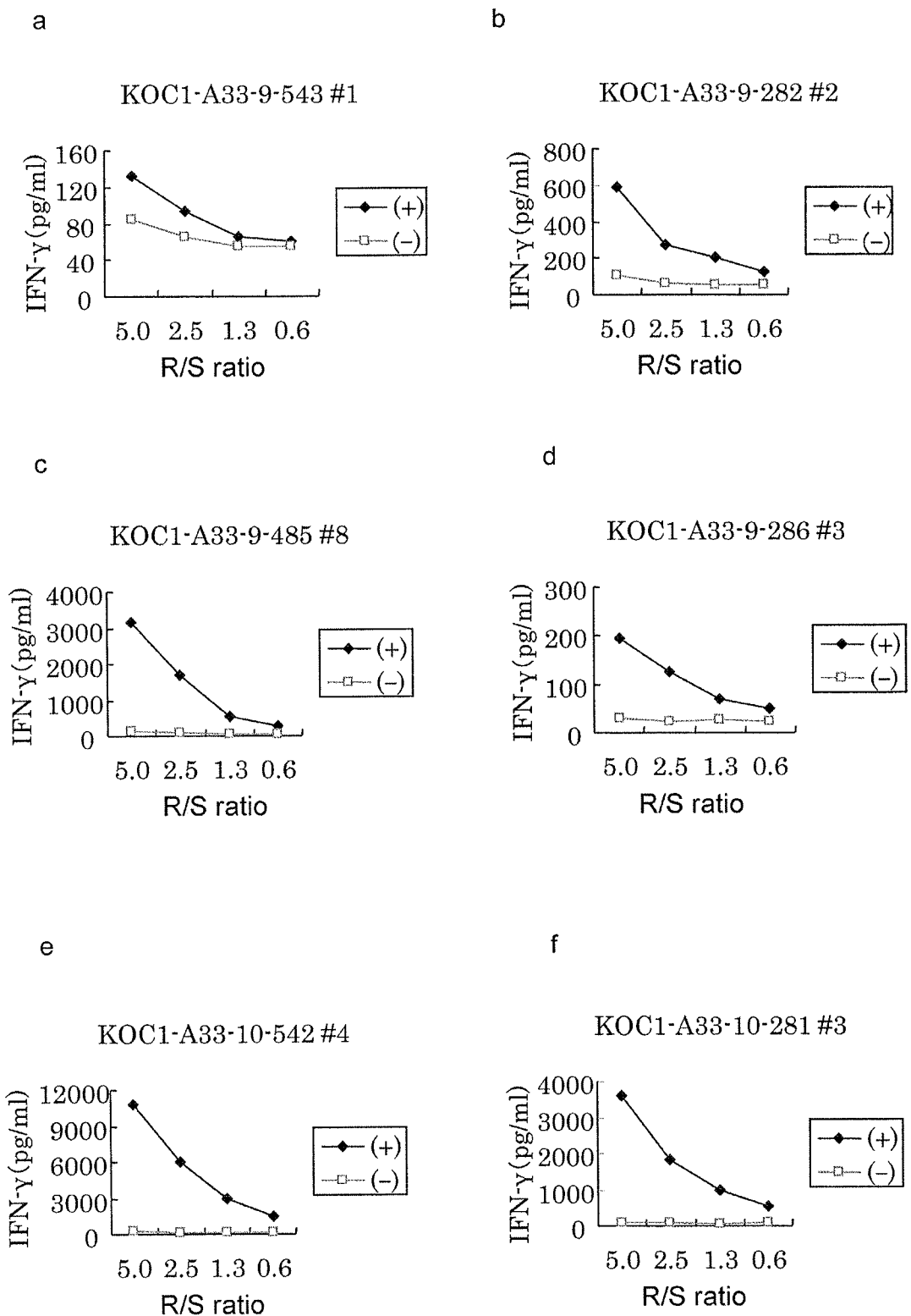
FIG. 6 consists of a series of line graphs (a) to (f) showing results of IFN-gamma ELISA, confirming IFN-gamma production in CTL lines stimulated with KOC1-A33-9-543 (SEQ ID NO: 61) (a), KOC1-A33-9-282 (SEQ ID NO: 62) (b), KOC1-A33-9-485 (SEQ ID NO: 64) (c), KOC1-A33-9-286 (SEQ ID NO: 67) (d), KOC1-A33-10-542 (SEQ ID NO: 77) (e), or KOC1-A33-10-281 (SEQ ID NO: 52) (f). These results prove that the CTL lines established by stimulation with each of the peptides showed potent IFN-gamma production in comparison with the control. In the figure, "+" shows IFN-gamma production against target cells pulsed with an appropriate peptide; and "−" shows IFN-gamma production against target cells that have not been pulsed with any peptides. The R/S ratio indicates the ratio of the cell number of CTL line (Responder cells) and the cell number of target cells (Stimulator cells).
Figure 7:
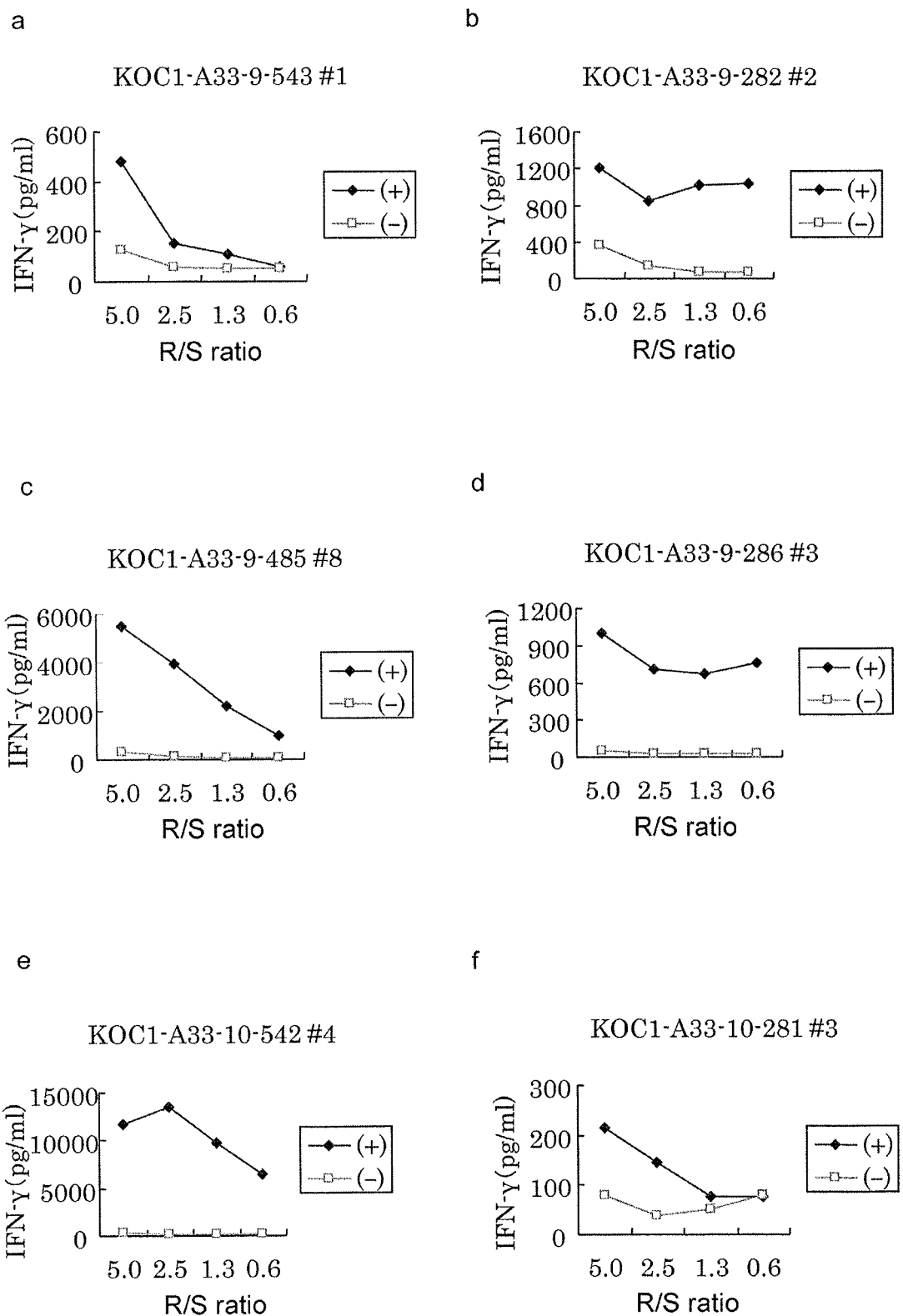
FIG. 7 consists of a series of line graphs (a) to (f) showing IFN-gamma production in CTL clones established by limiting dilution from CTL lines stimulated with KOC1-A33-9-543 (SEQ ID NO: 61) (a), KOC1-A33-9-282 (SEQ ID NO: 62) (b), KOC1-A33-9-485 (SEQ ID NO: 64) (c), KOC1-A33-9-286 (SEQ ID NO: 67) (d), KOC1-A33-10-542 (SEQ ID NO: 77) (e), or KOC1-A33-10-281 (SEQ ID NO: 52) (f). These results prove that the CTL clones established by stimulation with each of the peptides showed potent IFN-gamma production in comparison with the control. In the figure, "+" shows IFN-gamma production against target cells pulsed with an appropriate peptide; and "−" shows IFN-gamma production against target cells that have not been pulsed with any peptides. The R/S ratio indicates the ratio of the cell number of CTL clone (Responder cells) and the cell number of target cells (Stimulator cells).

Establishment of CTL Lines and Clones Against the KOC1-Derived HLA-A*3303-Restricted Peptides CTL lines were established by propagating CTLs in Well #1 with KOC1-A33-9-543 (SEQ ID NO: 61) (a), Well #2 with KOC1-A33-9-282 (SEQ ID NO: 62) (b), Well #8 with KOC1-A33-9-485 (SEQ ID NO: 64) (c), Well #3 with KOC1-A33-9-286 (SEQ ID NO: 67) (d), Well #4 with KOC1-A33-10-542 (SEQ ID NO: 77) (e), and Well #3 with KOC1-A33-10-281 (SEQ ID NO: 52) (0, which showed peptide-specific CTL activity in the IFN-gamma ELISPOT assay. The CTL activity of these CTL lines was measured by IFN-gamma ELISA (FIG. 6). These CTL lines showed potent IFN-gamma production against target cells pulsed with the respective peptides, in comparison with target cells that have not been pulsed with the peptides. Further, CTL clones were established from the CTL lines by limiting dilution as described in the "Materials and methods" section above, IFN-gamma production from the CTL clones against peptide-pulsed C1R-A33 was measured by IFN-gamma ELISA. Potent IFN-gamma production was observed in CTL clones stimulated with KOC1-A33-9-543 (SEQ ID NO: 61) (a), KOC1-A33-9-282 (SEQ ID NO: 62) (b), KOC1-A33-9-485 (SEQ ID NO: 64) (c), KOC1-A33-9-286 (SEQ ID NO: 67) (d), KOC1-A33-10-542 (SEQ ID NO: 77) (e), and KOC1-A33-10-281 (SEQ ID NO: 52) (f) (FIG. 7).

Specific CTL Activity Against Target Cells Expressing KOC1 and HLA-A*3303

Figure 8:
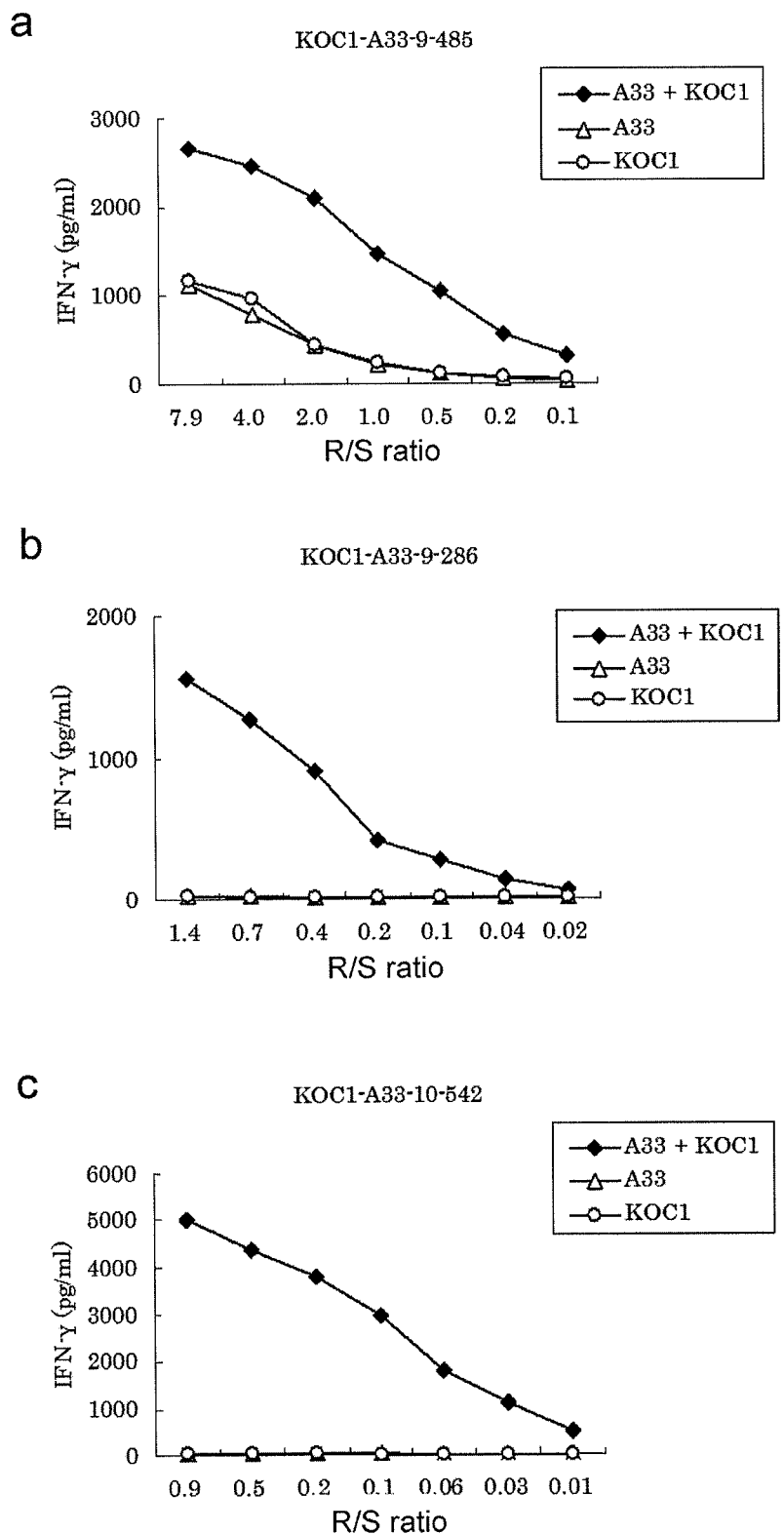
FIG. 8 consists of a series of line graphs (a) to (c) showing specific CTL activity against target cells expressing both KOC1 and HLA-A*3303. COS7 cells transfected with either HLA-A*3303 or the full-length KOC1 gene were prepared as the control. The CTL clones established using KOC1-A33-9-485 (SEQ ID NO: 64) (a), KOC1-A33-9-286 (SEQ ID NO: 67) (b), and KOC1-A33-10-542 (SEQ ID NO: 77) (c) demonstrated a specific CTL activity against COS7 cells transfected with both KOC1 and HLA-A*3303 (black diamond). On the other hand, a significant specific CTL activity was not shown against target cells transfected with either one of HLA-A*3303 (white triangle) and KOC1 (white circle).

The CTL lines and CTL clones established against KOC1-A33-9-485 (SEQ ID NO: 64) (a), KOC1-A33-9-286 (SEQ ID NO: 67) (b), and KOC1-A33-10-542 (SEQ ID NO: 77) (c) were investigated for their ability to recognize target cells expressing KOC1 and the HLA-A*3303 molecule. COS7 cells transfected with both full-length KOC1 and the HLA-A*3303 gene (a specific model of target cells expressing KOC1 and the HLA-A*3303 gene) were prepared as the target cell. COS7 cells transfected with either full-length KOC1 or HLA-A*3303 were prepared as the control. The CTL clones stimulated with KOC1-A33-9-485 (SEQ ID NO: 64) (a), KOC1-A33-9-286 (SEQ ID NO: 67) (b), or KOC1-A33-10-542 (SEQ ID NO: 77) (c) demonstrated potent CTL activities against COS7 cells expressing both KOC1 and HLA-A*3303 (FIG. 8). On the other hand, a significant specific CTL activity was not detected against the control cells. These data clearly proved that KOC1-A33-9-485 (SEQ ID NO: 64), KOC1-A33-9-286 (SEQ ID NO: 67), and KOC1-A33-10-542 (SEQ ID NO: 77) are peptides generated from endogenous processing of KOC1, and are presented on target cells with the HLA-A*3303 molecule and recognized by CTLs. These results demonstrated the possibility that KOC1-A33-9-485 (SEQ ID NO: 64), KOC1-A33-9-286 (SEQ ID NO: 67), and KOC1-A33-10-542 (SEQ ID NO: 77) may be suitable as a cancer vaccine for patients having a KOC1-expressing cancer.

Homology Analysis of Antigen Peptides

CTLs stimulated with KOC1-A33-9-543 (SEQ ID NO: 61), KOC1-A33-9-282 (SEQ ID NO: 62), KOC1-A33-9-317 (SEQ ID NO: 63), KOC1-A33-9-485 (SEQ ID NO: 64), KOC1-A33-9-286 (SEQ ID NO: 67), KOC1-A33-9-34 (SEQ ID NO: 74), KOC1-A33-10-542 (SEQ ID NO: 77), KOC1-A33-10-281 (SEQ ID NO: 52), KOC1-A33-10-543 (SEQ ID NO: 79), KOC1-A33-10-424 (SEQ ID NO: 80), or KOC1-A33-10-285 (SEQ ID NO: 85) demonstrated significant specific CTL activities. These results may be due to the fact that the KOC1-A33-9-543 (SEQ ID NO: 61), KOC1-A33-9-282 (SEQ ID NO: 62), KOC1-A33-9-317 (SEQ ID NO: 63), KOC1-A33-9-485 (SEQ ID NO: 64), KOC1-A33-9-286 (SEQ ID NO: 67), KOC1-A33-9-34 (SEQ ID NO: 74), KOC1-A33-10-542 (SEQ ID NO: 77), KOC1-A33-10-281 (SEQ ID NO: 52), KOC1-A33-10-543 (SEQ ID NO: 79), KOC1-A33-10-424 (SEQ ID NO: 80), and KOC1-A33-10-285 (SEQ ID NO: 85) sequences are homologous to peptides derived from other molecules known for sensitizing the human immune system. In order to exclude this possibility, homology analysis was performed by querying these peptide sequences using the BLAST algorithm (blast.ncbi.nlm.nih.gov/Blast.cgi). This result proved that the KOC1-A33-9-543 (SEQ ID NO: 61), KOC1-A33-9-317 (SEQ ID NO: 63), KOC1-A33-9-485 (SEQ ID NO: 64), KOC1-A33-9-34 (SEQ ID NO: 74), KOC1-A33-10-542 (SEQ ID NO: 77), KOC1-A33-10-543 (SEQ ID NO: 79), and KOC1-A33-10-424 (SEQ ID NO: 80) sequences are unique. On the other hand, KOC1-A33-9-282 (SEQ ID NO: 62), KOC1-A33-9-286 (SEQ ID NO: 67), KOC1-A33-10-281 (SEQ ID NO: 52), and KOC1-A33-10-285 (SEQ ID NO: 85) are identical to peptide sequences identified in IMP-1 which is another IMP family. KOC1-A33-9-485

(SEQ ID NO: 64) is identical to a peptide sequence identified in IMP-2. It has been previously reported that IMP-1 is not expressed in normal organs except testis, fetal liver and placenta (Hammer N A et al., Reproduction. 2005; 130(2): 203-12). It is reported to be associated with tumor progression in lung cancer patients (Kato T et al., Clin Cancer Res. 2007; 13: 434-42). It has been previously reported that IMP-2 is not expressed in normal organs except testis and fetal liver (Hammer N A et al., Reproduction. 2005; 130(2): 203-12). It is involved in the proliferation of glioblastoma cancer stem cells (Janiszewska Metal., Genes Dev. 2012; 26(17): 1926-44). IMP-1 and IMP-2 are promising as target antigens for cancer immunotherapy. Therefore, to the knowledge of the present inventors, there is almost no possibility that these peptides would elicit an unintended immune response against other unrelated molecules. In conclusion, novel KOC1-derived HLA-A33-restricted epitope peptides were identified. It was demonstrated that the KOC1-derived epitope peptides are applicable for cancer immunotherapy.

Example 3

Materials and Methods
Cell Lines

C1R, an HLA-A- and HLA-B-negative human B lymphoblastoid cell line, and COST, an African green monkey kidney cell line, were purchased from ATCC.
Generation of Stimulator Cells with Stable HLA-A*0301 Expression C1R (C1R-A03) that stably expresses HLA-A*0301 was used as a stimulator cell. A cDNA encoding the open-reading frame of HLA-A*0301 was amplified by PCR and cloned into an expression vector. C1R cells were transfected with the expression vector, and then selected using G418 (Invitrogen) for two weeks. The G418-selected cells were seeded into wells containing G418-added culture medium in a 96-well plate, and further cultured for 30 days. The exogenous HLA-A*0301 expression in C1R cells was verified by flow cytometric analysis.
Selection of Candidate KOC1-Derived Peptides KOC1-derived 9mer and 10mer peptides that bind to the HLA-A*0301 molecule were predicted using the binding prediction server "NetMHC 3.2" (www.cbs.dtu.dk/services/NetMHC/) (Buus et al., Tissue Antigens. 2003 November, 62(5): 378-84; Nielsen et al., Protein Sci. 2003 May, 12(5): 1007-17; Bioinformatics. 2004 Jun. 12: 20(9): 1388-97).
Peptide Synthesis The peptides were synthesized by Biosynthesis (Lewisville, Tex.) according to a standard solid-phase synthesis method, and purified by reversed phase high-performance liquid chromatography (HPLC). The peptides were analyzed for their purity (>90%) and identity by analytical HPLC and mass spectrometry, respectively. The peptides were dissolved in dimethylsulfoxide at 20 mg/ml and stored at −80 degrees C.
In Vitro CTL Induction Monocyte-derived dendritic cells (DCs) were used as the antigen-presenting cell to induce a cytotoxic T lymphocyte (CTL) response against peptides presented on human leukocyte antigens (HLAs). As described in the other sections, DCs were generated in vitro (Nakahara S et al., Cancer Res 2003, 63(14): 4112-8). Specifically, peripheral-blood mononuclear cells isolated from healthy volunteers (HLA-A*0301-positive) with the Ficoll-Paque plus solution (Pharmacia) were separated by attaching to plastic tissue culture dishes (Becton Dickinson) and concentrated as a monocyte fraction. The monocyte-concentrated population was cultured in the presence of 1000 IU/ml granulocyte macrophage colony-stimulating factor (R&D System) and 1000 IU/ml interleukin(IL)-4 (R&D System) in an AIM-V medium (Invitrogen) containing 2% heat-inactivated autologous serum (AS). After seven days of culturing, the cytokine-induced DCs were pulsed with 20 micro-g/ml each of the synthesized peptides in an AIM-V medium at 37 degrees C. for three hours in the presence of 3 micro-g/ml beta 2-microglobulin. The generated cells appeared to express on their cell surface DC-associated molecules such as CD80, CD83, CD86 and HLA class II (data not shown). Next, these peptide-pulsed DCs were inactivated by X-ray irradiation (20 Gy), and mixed in a 1:20 ratio with autologous CD8$^+$ T cells obtained by positive selection using the CD8 Positive Isolation Kit (Dynal). These culture products were seeded in a 48-well plate (Corning). Each well was made to contain $1.5 \times 10^4$ peptide-pulsed DCs, $3 \times 10^5$ CD8$^+$ T cells and 10 ng/ml IL-7 (R&D System) in 0.5 ml of the AIM-V/2% AS medium. Three days later, these culture products were added with a final concentration of 20 IU/ml IL-2 (CHIRON). On day 7 and day 14, T cells were further stimulated with peptide-pulsed autologous DCs. The DCs were prepared every time by the same method as above. On day 21, after the third peptide stimulation, CTLs were examined against the peptide-pulsed C1R-A03 by a human interferon (IFN)-gamma enzyme-linked immunospot (ELISPOT) assay (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).
CTL Propagation Procedure CTLs were propagated in culture using methods similar to those disclosed by Riddell et al. (Walter E A et al., N Engl J Med 1995, 333(16): 1038-44; Riddell S R et al., Nat Med 1996, 2(2): 216-23). The CTLs were co-cultured in a total of 25 ml AIM-V medium containing 5% AS (AIM-V/5% AS) and 40 ng/ml anti-CD3 antibody with two types of Mitomycin C-treated human B lymphoblastoid cell lines at $5 \times 10^6$ cells/flask. One day after beginning of the culturing, 120 IU/ml IL-2 was added to the culture. On days 5, 8 and 11, a fresh AIM-V/5% AS medium containing 30 IU/ml IL-2 was added to the culture (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).
Establishment of CTL Clones Dilution of CTLs was carried out to make 0.3, 1 and 3 cells/well in 96 round-bottomed microtiter plates (Nalge Nunc International). The CTLs were co-cultured with two types of Mitomycin C-treated human B lymphoblastoid cell lines at $1 \times 10^4$ cells/well in a total of 150 micro-1/well AIM-V/5% AS medium with 30 ng/ml anti-CD3 antibody and 125 IU/ml IL-2. Ten days later, IL-2 was added to the medium at 50 micro-1/well to reach a final concentration of 125 IU/ml. On day 14, the CTL activity was tested, and the CTL clones were propagated using the same method as described above (Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).
Specific CTL Activity To examine specific CTL activity, an IFN-gamma ELISPOT assay and an IFN-gamma enzyme-linked immunosorbent assay (ELISA) were performed. Specifically, peptide-pulsed C1R-A03 ($1 \times 10^4$ cells/well) was prepared as the stimulator cell. The induced CTLs, i.e., CTL lines and CTL clones, were used as the responder cell. The IFN-gamma ELISPOT assay and IFN-gamma ELISA were performed according to the manufacturer's manual.

Establishment of Target Cells Forcibly Expressing a Target Gene and HLA-A*0301

A cDNA encoding the open-reading frame of a target gene or HLA-A*0301 was amplified by PCR. The PCR-amplified product was cloned into an expression vector. Either or both of the target gene-expressing vector and the HLA-A*0301-expressing vector were transfected into COST, which is a cell line negative for the target gene and HLA, using Lipofectamine 2000 (Invitrogen) following the manufacturer's recommended protocol. Two days after transfection, the transfected cells were harvested using versene (Invitrogen), and used as the target cell for CTL activity assay ($5 \times 10^4$ cells/well).

Results

Prediction of KOC1-Derived HLA-A*0301-Binding Peptides

Tables 3a and 3b show KOC1-derived 9mer peptides and 10mer peptides that have been predicted to bind to HLA-A*0301 in the descending order of binding affinity. A total of 23 peptides that potentially have an HLA-A*0301-binding ability was selected and investigated to determine epitope peptides.

TABLE 3a

HLA-A3-binding 9mer peptides derived from KOC1

| Start position | Amino acid sequence | Kd (nM) | SEQ ID NO |
|---|---|---|---|
| 121 | VVNVTYSSK | 84 | 2 |
| 258 | KSILEIMHK | 124 | 1 |
| 52 | KAIEALSGK | 496 | 7 |
| 28 | PVSGPFLVK | 613 | 6 |
| 465 | KAQGRIYGK | 650 | 3 |
| 142 | FQLENFTLK | 752 | 8 |
| 415 | LSVGAIIGK | 764 | 5 |
| 497 | FAAGRVIGK | 927 | 11 |
| 559 | QVKQHQQQK | 1152 | 24 |

TABLE 3b

HLA-A3-binding 10mer peptides derived from KOC1

| Start position | Amino acid sequence | Kd (nM) | SEQ ID NO |
|---|---|---|---|
| 120 | AVVNVTYSSK | 17 | 27 |
| 414 | ALSVGAIIGK | 37 | 28 |
| 431 | LSRFAGASIK | 69 | 37 |
| 181 | RQGSPGSVSK | 104 | 38 |
| 456 | ITGPPEAQFK | 211 | 29 |
| 204 | TQFVGAIIGK | 211 | 30 |
| 496 | SFAAGRV1GK | 215 | 34 |

TABLE 3b-continued

HLA-A3-binding 10mer peptides derived from KOC1

| Start position | Amino acid sequence | Kd (nM) | SEQ ID NO |
|---|---|---|---|
| 552 | KIQEILTQVK | 365 | 36 |
| 281 | ILAHNNFVGR | 459 | 52 |
| 73 | SVPKRQRIRK | 521 | 31 |
| 535 | VVVKITGHFY | 682 | 41 |
| 420 | IIGKQGQHIK | 858 | 55 |
| 141 | GFQLENFTLK | 1112 | 44 |
| 14 | APSDLESIFK | 1275 | 32 |

Start position indicates the number of amino acid residue from the N-terminus of KOC1. The dissociation constant [Kd (nM)] is derived from "NetMHC3.2".

Induction of CTLs by the Predicted KOC1-Derived HLA-A*0301-Restricted Peptides

Figure 9:
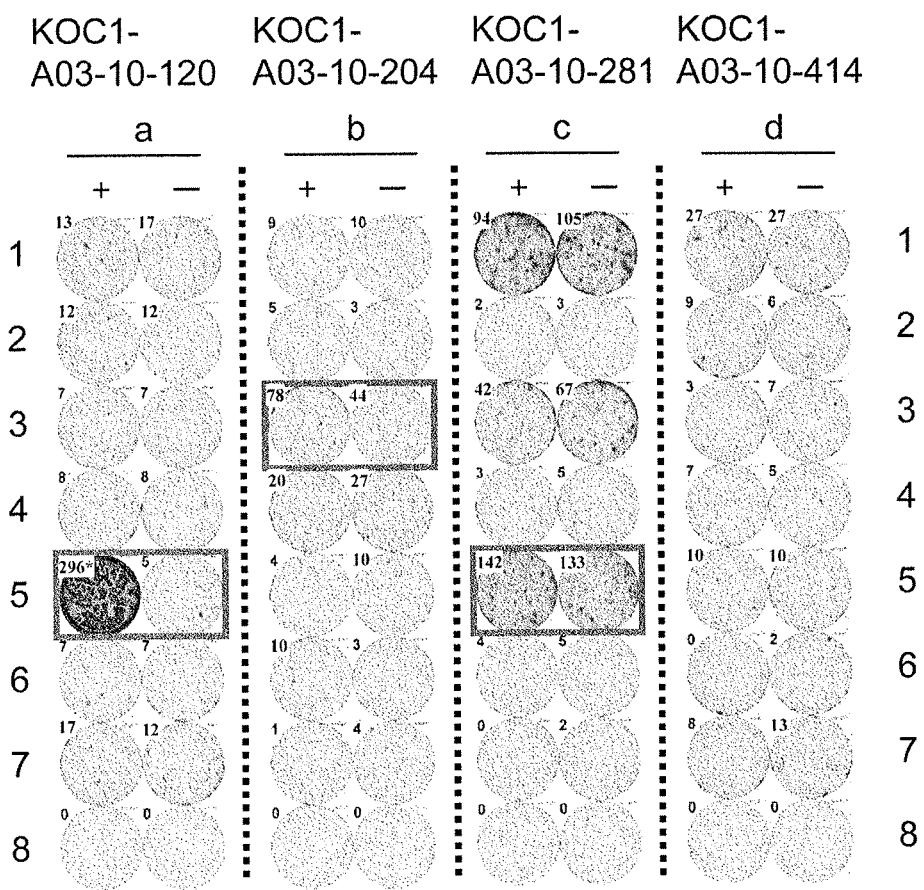
FIG. 9 consists of photos (a) to (d) showing results of an IFN-gamma ELISPOT assay in CTLs induced using peptides derived from KOC1. In comparison with the control, CTLs in Well #5 with KOC1-A03-10-120 (SEQ ID NO: 27) (a), Well #3 with KOC1-A03-10-204 (SEQ ID NO: 30) (b), and Well #5 with KOC1-A03-10-281 (SEQ ID NO: 52) (c) showed potent IFN-gamma production. In these photos, the square on the wells show that cells from the respective wells were propagated for the establishment of CTL lines. In contrast, KOC1-A03-10-414 (SEQ ID NO: 28) (d) is shown as an example of typical negative data where there was no specific IFN-gamma production. In the figure, "+" shows IFN-gamma production against target cells pulsed with an appropriate peptide; and "−" shows IFN-gamma production against target cells that have not been pulsed with any peptides.

CTLs against the KOC1-derived peptides were generated according to the protocol described in "Materials and methods". The peptide-specific CTL activity was measured by an IFN-gamma ELISPOT assay (FIG. 9). In comparison with the control, CTLs in Well #5 with KOC1-A03-10-120 (SEQ ID NO: 27) (a), Well #3 with KOC1-A03-10-204 (SEQ ID NO: 30) (b), and Well #5 with KOC1-A03-10-281 (SEQ ID NO: 52) (c) showed potent IFN-gamma production. Meanwhile, despite that other peptides shown in Tables 3a and 3b potentially have an HLA-A*0301-binding activity, specific CTL activity was not detected as a result of stimulation by those peptides. An example of typical negative data is that specific IFN-gamma production was not observed from CTLs stimulated with KOC1-A03-10-414 (SEQ ID NO: 28) (d). As a result, three types of KOC1-derived peptides were selected as peptides capable of inducing potent CTLs.

Figure 10:
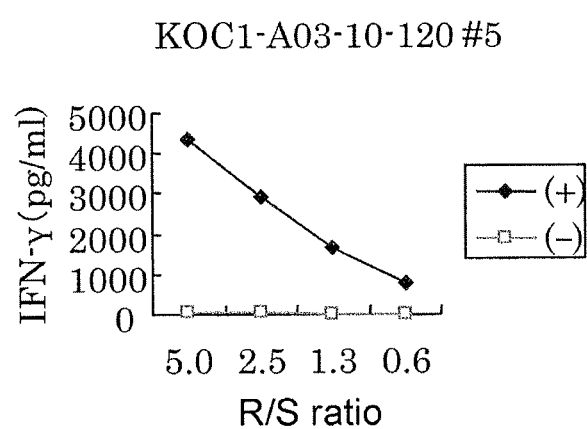
FIG. 10 is a line graph showing results of IFN-gamma ELISA, confirming IFN-gamma production in a CTL line stimulated with KOC1-A03-10-120 (SEQ ID NO: 27). These results prove that the CTL line established by stimulation with each of the peptides showed potent IFN-gamma production in comparison with the control. In the figure, "+" shows IFN-gamma production against target cells pulsed with an appropriate peptide; and "−" shows IFN-gamma production against target cells that have not been pulsed with any peptides. The R/S ratio indicates the ratio of the cell number of the CTL line (Responder cells) and the cell number of the target cells (Stimulator cells).
Figure 11:
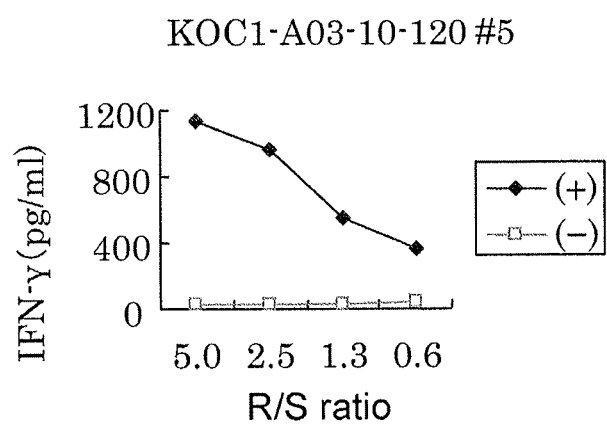
FIG. 11 is a line graph showing IFN-gamma production in a CTL clone established by limiting dilution from the CTL line stimulated with KOC1-A03-10-120 (SEQ ID NO: 27). These results prove that the CTL clone established by stimulation with each of the peptides showed potent IFN-gamma production in comparison with the control. In the figure, "+" shows IFN-gamma production against target cells pulsed with an appropriate peptide; and "−" shows IFN-gamma production against target cells that have not been pulsed with any peptides. The R/S ratio indicates the ratio of the cell number of the CTL clone (Responder cells) and the cell number of the target cells (Stimulator cells).

Establishment of CTL Lines and Clones Against the KOC1-Derived HLA-A*0301-Restricted Peptides CTL line was established by propagating CTLs in Well #5 with KOC1-A03-10-120 (SEQ ID NO: 27), which showed peptide-specific CTL activity in the IFN-gamma ELISPOT assay. The CTL activity of these CTL lines was measured by IFN-gamma ELISA (FIG. 10). These CTL lines showed potent IFN-gamma production against target cells pulsed with the respective peptides, in comparison with target cells that have not been pulsed with the peptides. Further, CTL clones were established from the CTL lines by limiting dilution as described in the "Materials and methods" section above, IFN-gamma production from the CTL clones against peptide-pulsed C1R-A03 was measured by IFN-gamma ELISA. Potent IFN-gamma production was observed in CTL clone stimulated with KOC1-A03-10-120 (SEQ ID NO: 27) (FIG. 11).

Specific CTL Activity Against Target Cells Expressing KOC1 and HLA-A*0301

The CTL clone established against KOC1-A03-10-120 (SEQ ID NO: 27) was investigated for their ability to recognize target cells expressing KOC1 and the HLA-A*0301 molecule. COS7 cells transfected with both full-length KOC1 and the HLA-A*0301 gene (a specific model of target cells expressing KOC1 and the HLA-A*0301 gene) were prepared as the target cell. COS7 cells transfected with either full-length KOC1 or HLA-A*0301 were prepared as the control. The CTL clone stimulated with KOC1-A03-10-

Figure 12:
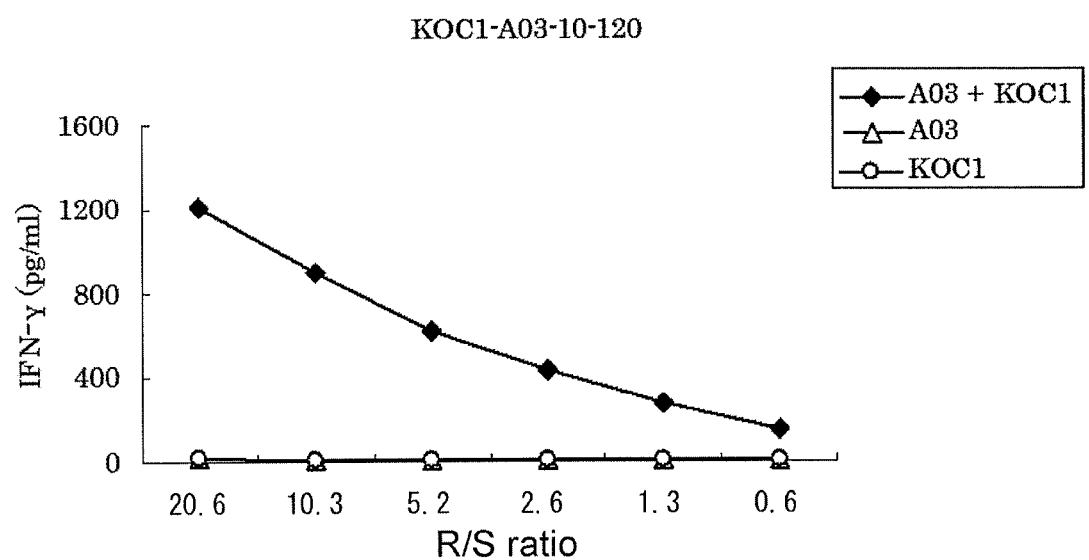
FIG. 12 is a line graph showing specific CTL activity against target cells expressing both KOC1 and HLA-A*0301. COS7 cells transfected with either HLA-A*0301 or the full-length KOC1 gene were prepared as the control. The CTL clone established using KOC1-A03-10-120 (SEQ ID NO: 27) demonstrated a specific CTL activity against COS7 cells transfected with both KOC1 and HLA-A*0301 (black diamond). On the other hand, a significant specific CTL activity was not shown against target cells transfected with either one of HLA-A*0301 (white triangle) and KOC1 (white circle).

120 (SEQ ID NO: 27) demonstrated potent CTL activities against COS7 cells expressing both KOC1 and HLA-A*0301 (FIG. 12). On the other hand, a significant specific CTL activity was not detected against the control cells. These data clearly proved that KOC1-A03-10-120 (SEQ ID NO: 27) is a peptide generated from endogenous processing of KOC1, and is presented on target cells with the HLA-A*0301 molecule and recognized by CTLs. These results demonstrated the possibility that KOC1-A03-10-120 (SEQ ID NO: 27) may be suitable as a cancer vaccine for patients having a KOC1-expressing cancer.

Homology Analysis of Antigen Peptides

CTLs stimulated with KOC1-A03-10-120 (SEQ ID NO: 27), KOC1-A03-10-204 (SEQ ID NO: 30), or KOC1-A03-10-281 (SEQ ID NO: 52) demonstrated significant specific CTL activities. These results may be due to the fact that the KOC1-A03-10-120 (SEQ ID NO: 27), KOC1-A03-10-204 (SEQ ID NO: 30) and KOC1-A03-10-281 (SEQ ID NO: 52) sequences are homologous to peptides derived from other molecules known for sensitizing the human immune system. In order to exclude this possibility, homology analysis was performed by querying these peptide sequences using the BLAST algorithm (blast.ncbi.nlm.nih.gov/Blast.cgi). This result showed that there is no sequence having a significant homology with the KOC1-A03-10-120 (SEQ ID NO: 27) sequence. On the other hand, KOC1-A03-10-204 (SEQ ID NO: 30) is identical to a peptide sequence identified in IMP-2 which is another IMP family. KOC1-A03-10-281 (SEQ ID NO: 52) is identical to a peptide sequence identified in IMP-1 which is another IMP family. It has been previously reported that IMP-1 is not expressed in normal organs except testis, fetal liver and placenta (Hammer N A et al., Reproduction. 2005; 130(2): 203-12). It is reported to be associated with tumor progression in lung cancer patients (Kato T et al., Clin Cancer Res. 2007; 13: 434-42). It has been previously reported that IMP-2 is not expressed in normal organs except testis and fetal liver (Hammer N A et al., Reproduction. 2005; 130(2): 203-12). It is involved in the proliferation of glioblastoma cancer stem cells (Janiszewska M et al., Genes Dev. 2012; 26(17): 1926-44). IMP-1 and IMP-2 are promising as target antigens for cancer immunotherapy. Therefore, to the knowledge of the present inventors, there is almost no possibility that these peptides would elicit an unintended immune response against other unrelated molecules. In conclusion, novel KOC1-derived HLA-A03-restricted epitope peptides were identified. It was demonstrated that the KOC1-derived epitope peptides are applicable for cancer immunotherapy.

Example 4

Materials and Methods
Cell Lines

C1R, an HLA-A- and HLA-B-negative human B lymphoblastoid cell line, and COS7, an African green monkey kidney cell line, were purchased from ATCC.

Generation of Stimulator Cells with Stable HLA-A*0101 Expression

CIR (C1R-A01) that stably expresses HLA-A*0101 was used as a stimulator cell. A cDNA encoding the open-reading frame of HLA-A*0101 was amplified by PCR and cloned into an expression vector. C1R cells were transfected with the expression vector, and then selected using G418 (Invitrogen) for two weeks. The G418-selected cells were seeded into wells containing G418-added culture medium in a 96-well plate, and further cultured for 30 days. The exogenous HLA-A*0101 expression in C1R cells was verified by flow cytometric analysis.

Selection of Candidate KOC1-Derived Peptides

KOC1-derived 9mer and 10mer peptides that bind to the HLA-A*0101 molecule were predicted using the binding prediction server "NetMHC 3.2" (www.cbs.dtu.dk/services/NetMHC/) (Buus et al., Tissue Antigens. 2003 November, 62(5):378-84; Nielsen et al., Protein Sci. 2003 May, 12(5): 1007-17; Bioinformatics. 2004 Jun. 12: 20(9): 1388-97).

Peptide Synthesis

The peptides were synthesized by American Peptide Company (Sunnyvale, Calif.) according to a standard solid-phase synthesis method, and purified by reversed phase high-performance liquid chromatography (HPLC). The peptides were analyzed for their purity (>90%) and identity by analytical HPLC and mass spectrometry, respectively. The peptides were dissolved in dimethylsulfoxide at 20 mg/ml and stored at −80 degrees C.

In Vitro CTL Induction

Monocyte-derived dendritic cells (DCs) were used as the antigen-presenting cell to induce a cytotoxic T lymphocyte (CTL) response against peptides presented on human leukocyte antigens (HLAs). As described in the other sections, DCs were generated in vitro (Nakahara S et al., Cancer Res 2003, 63(14): 4112-8). Specifically, peripheral-blood mononuclear cells isolated from healthy volunteers (HLA-A*0101-positive) with the Ficoll-Paque plus solution (Pharmacia) were separated by attaching to plastic tissue culture dishes (Becton Dickinson) and concentrated as a monocyte fraction. The monocyte-concentrated population was cultured in the presence of 1000 IU/ml granulocyte macrophage colony-stimulating factor (R&D System) and 1000 IU/ml interleukin(IL)-4 (R&D System) in an AIM-V medium (Invitrogen) containing 2% heat-inactivated autologous serum (AS). After seven days of culturing, the cytokine-induced DCs were pulsed with 20 micro-g/ml each of the synthesized peptides in an AIM-V medium at 37 degrees C. for three hours in the presence of 3 micro-g/ml beta 2-microglobulin. Next, these peptide-pulsed DCs were inactivated by X-ray irradiation (20 Gy), and mixed in a 1:20 ratio with autologous CD8+ T cells obtained by positive selection using the CD8 Positive Isolation Kit (Dynal). These culture products were seeded in a 48-well plate (Corning). Each well was made to contain $1.5 \times 10^4$ peptide-pulsed DCs, $3 \times 10^5$ CD8+ T cells and 10 ng/ml IL-7 (R&D System) in 0.5 ml of the AIM-V/2% AS medium. Three days later, these culture products were added with a final concentration of 20 IU/ml IL-2 (CHIRON). On day 7 and day 14, T cells were further stimulated with peptide-pulsed autologous DCs. The DCs were prepared every time by the same method as above. On day 21, after the third peptide stimulation, CTL activities were examined against the peptide-pulsed C1R-A01 cells (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

CTL Propagation Procedure

CTLs were propagated in culture using methods similar to those disclosed by Riddell et al. (Walter E A et al., N Engl J Med 1995, 333(16): 1038-44; Riddell S R et al., Nat Med 1996, 2(2): 216-23). The CTLs were co-cultured in a total of 25 ml AIM-V medium containing 5% AS and 40 ng/ml anti-CD3 antibody with two types of Mitomycin C-treated human B lymphoblastoid cell lines at $5 \times 10^6$ cells. One day after beginning of the culturing, 120 IU/ml IL-2 was added to the culture. On days 5, 8 and 11, a fresh AIM-V/5% AS medium containing 30 IU/ml IL-2 was added to the culture (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Establishment of CTL Clones

CTLs were seeded to make 1 or 10 cells/well in 96 round-bottomed microtiter plates (Nalge Nunc International). The CTLs were co-cultured with two types of Mitomycin C-treated human B lymphoblastoid cell lines at 1×10⁴ cells in a total of 150 micro-l/well 5% AS-containing AIM-V medium with 30 ng/ml anti-CD3 antibody and 125 IU/ml IL-2. Ten days later, 50 micro-1 of IL-2 was added to the medium to reach a final IL-2 concentration of 125 IU/ml. On day 14, the CTL activity was tested, and the CTL clones were propagated using the same method as described above (Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Specific CTL Activity

To examine specific CTL activity, an IFN-gamma ELISPOT assay and an IFN-gamma enzyme-linked immunosorbent assay (ELISA) were performed. Specifically, peptide-pulsed C1R-A01 (1×10⁴ cells/well) was prepared as the stimulator cell. The induced CTLs, i.e., CTL lines and CTL clones, were used as the responder cell. The IFN-gamma ELISPOT assay and IFN-gamma ELISA were performed according to the manufacturer's manual.

Establishment of Target Cells Forcibly Expressing a Target Gene and HLA-A*0101

A cDNA encoding the open-reading frame of a target gene or HLA-A*0101 was amplified by PCR. The PCR-amplified product was cloned into an expression vector. Expression vectors were transfected using Lipofectamine 2000 (Invitrogen) following the manufacturer's recommended protocol. Two days after transfection, the transfected cells were harvested using versene (Invitrogen), and used as the stimulator cell for CTL activity assay (5×10⁴ cells/well).

Results

Prediction of KOC1-Derived HLA-A*0101-Binding Peptides

Tables 4a and 4b show KOC1-derived 9mer peptides and 10mer peptides that have been predicted to bind to HLA-A*0101 in the descending order of binding affinity. A total of 27 peptides that potentially have an HLA-A*0101-binding ability was selected and investigated to determine epitope peptides.

TABLE 4a

HLA-A1-binding 9mer peptides derived from KOC1

| Start position | Amino acid sequence | Kd (nM) | SEQ ID NO |
|---|---|---|---|
| 96 | VLDSLLVQY | 56 | 86 |
| 118 | ETAVVNVTY | 57 | 87 |
| 114 | NTDSETAVV | 453 | 88 |
| 273 | FTEEIPLKI | 528 | 89 |
| 404 | ETETVHLFI | 1528 | 90 |
| 536 | VVKITGHFY | 5589 | 13 |

TABLE 4a-continued

HLA-A1-binding 9mer peptides derived from KOC1

| Start position | Amino acid sequence | Kd (nM) | SEQ ID NO |
|---|---|---|---|
| 15 | PSDLESIFK | 5882 | 12 |
| 143 | QLENFTLKV | 11578 | 91 |
| 402 | QSETETVHL | 13101 | 92 |
| 305 | DTDTKITIS | 13406 | 93 |
| 313 | SPLQELTLY | 21305 | 94 |
| 338 | KAEEEIMKK | 23866 | 10 |
| 301 | KIEQDTDTK | 24016 | 21 |
| 69 | EVEHSVPKR | 24734 | 69 |

TABLE 4b

HLA-A1-binding 10mer peptides derived from KOC1

| Start position | Amino acid sequence | Kd (nM) | SEQ ID NO |
|---|---|---|---|
| 312 | ISPLQELTLY | 146 | 46 |
| 95 | EVLDSLLVQY | 498 | 50 |
| 402 | QSETETVHLF | 1737 | 95 |
| 9 | LSENAAPSDL | 2164 | 96 |
| 535 | VVVKITGHFY | 3359 | 41 |
| 273 | FTEEIPLKIL | 4478 | 97 |
| 462 | AQFKAQGRIY | 6263 | 98 |
| 342 | EIMKKIRESY | 7665 | 99 |
| 252 | GTSAACKSIL | 9689 | 100 |
| 30 | SGPFLVKTGY | 17794 | 101 |
| 114 | NTDSETAVVN | 22411 | 102 |
| 305 | DTDTKITISP | 29728 | 103 |
| 17 | DLESIFKDAK | 35078 | 104 |

Start position indicates the number of amino acid residue from the N-terminus of KOC1. The dissociation constant [Kd (nM)] is derived from "NetMHC3.2".

Induction of CTLs by the Predicted KOC1-Derived HLA-A*0101-Restricted Peptides

Figure 13:
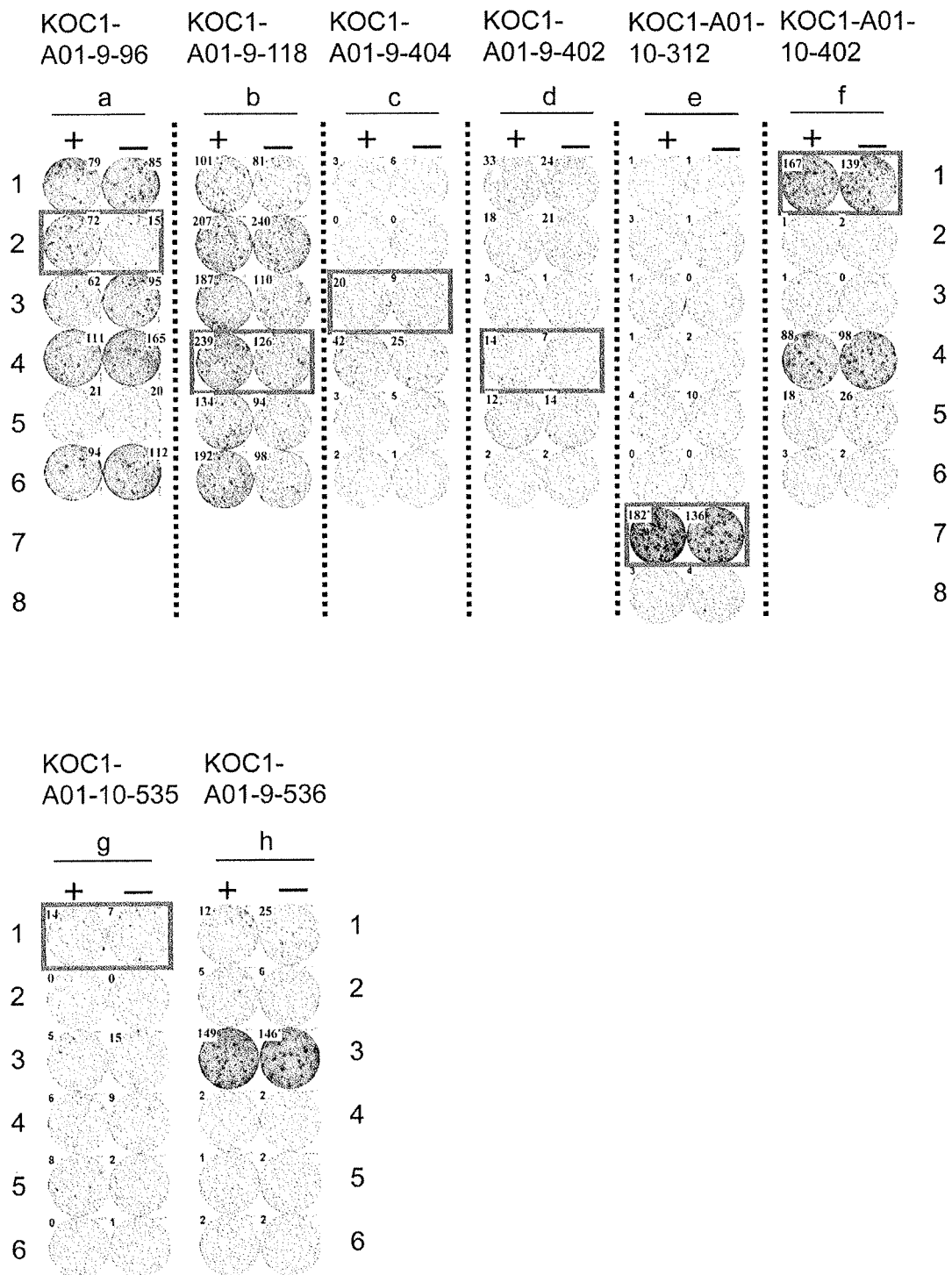
FIG. 13 consists of photos (a) to (h) showing results of an IFN-gamma ELISPOT assay in CTLs induced using peptides derived from KOC1. In comparison with the control, CTLs in Well #2 with KOC1-A01-9-96 (SEQ ID NO: 86) (a), Well #4 with KOC1-A01-9-118 (SEQ ID NO: 87) (b), Well #3 with KOC1-A01-9-404 (SEQ ID NO: 90) (c), Well #4 with KOC1-A01-9-402 (SEQ ID NO: 92) (d), Well 7# with KOC1-A01-10-312 (SEQ ID NO: 46) (e), Well #1 with KOC1-A01-10-402 (SEQ ID NO: 95) (0, and Well #1 with KOC1-A01-10-535 (SEQ ID NO: 41) (g) showed potent IFN-gamma production. In these photos, the square on the wells show that cells from the respective wells were propagated for establishment of CTL lines. In contrast, KOC1-A01-9-536 (SEQ ID NO: 13) (h) is shown as an example of typical negative data where there was no specific IFN-gamma production. In the figure, "+" shows IFN-gamma production against target cells pulsed with an appropriate peptide; and "−" shows IFN-gamma production against target cells that have not been pulsed with any peptides.

CTLs against the KOC1-derived peptides were generated according to the protocol described in "Materials and methods". The peptide-specific CTL activity was measured by an IFN-gamma ELISPOT assay (FIG. 13). In comparison with the control, CTLs in Well #2 with KOC1-A01-9-96 (SEQ ID NO: 86) (a), Well #4 with KOC1-A01-9-118 (SEQ ID NO: 87) (b), Well #3 with KOC1-A01-9-404 (SEQ ID NO: 90) (c), Well #4 with KOC1-A01-9-402 (SEQ ID NO: 92) (d), Well #7 with KOC1-A01-10-312 (SEQ ID NO: 46) (e), Well #1 with KOC1-A01-10-402 (SEQ ID NO: 95) (f) and Well #1 with KOC1-A01-10-535 (SEQ ID NO: 41) (g) showed potent IFN-gamma production. Meanwhile, despite that other peptides shown in Tables 4a and 4b potentially have an HLA-A*0101-binding activity, specific CTL activity was not detected as a result of stimulation by those peptides. An example of typical negative data is that specific IFN-gamma production was not observed from CTLs stimulated with KOC1-A01-9-536 (SEQ ID NO: 13) (h). As a result, seven types of KOC1-derived peptides were selected as peptides capable of inducing potent CTLs.

Establishment of CTL Lines and Clones Against the KOC1-Derived Peptides

Figure 14:
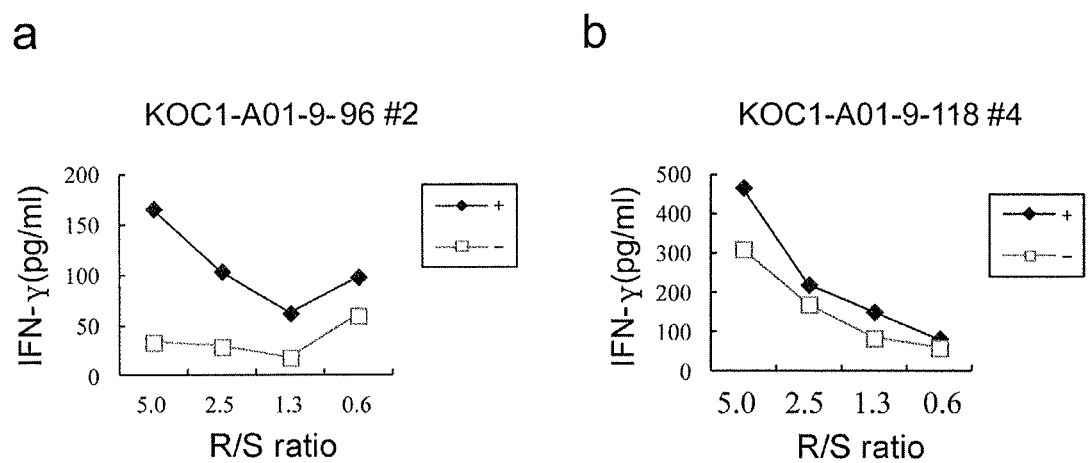
FIG. 14 consists of a series of line graphs (a) and (b) showing results of IFN-gamma ELISA, confirming IFN-gamma production in CTL lines stimulated with KOC1-A01-9-96 (SEQ ID NO: 86) (a) or KOC1-A01-9-118 (SEQ ID NO: 87) (b). These results prove that the CTL lines established by stimulation with each of the peptides showed potent IFN-gamma production in comparison with the control. In the figure, "+" shows IFN-gamma production against target cells pulsed with an appropriate peptide; and "−" shows IFN-gamma production against target cells that have not been pulsed with any peptides. The R/S ratio indicates the ratio of the cell number of CTL line (Responder cells) and the cell number of target cells (Stimulator cells).
Figure 15:
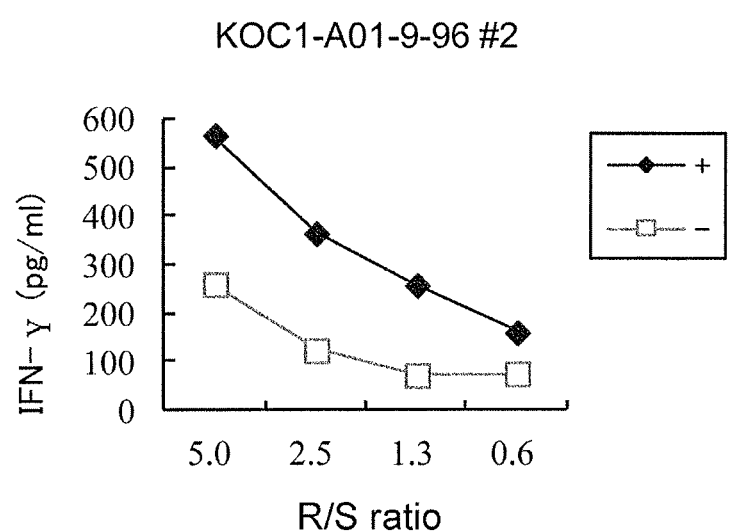
FIG. 15 is a line graph showing IFN-gamma production in a CTL clone established by limiting dilution from the CTL line stimulated with KOC1-A01-9-96 (SEQ ID NO: 86). These results prove that the CTL clone established by stimulation with each of the peptides showed potent IFN-gamma production in comparison with the control. In the figure, "+" shows IFN-gamma production against target cells pulsed with an appropriate peptide; and "−" shows IFN-gamma production against target cells that have not been pulsed with any peptides. The R/S ratio indicates the ratio of the cell number of the CTL clone (Responder cells) and the cell number of the target cells (Stimulator cells).

CTL lines were established by propagating CTLs in Well #2 with KOC1-A01-9-96 (SEQ ID NO: 86) (a) and Well #4 with KOC1-A01-9-118 (SEQ ID NO: 87) (b), which showed peptide-specific CTL activity in the IFN-gamma ELISPOT assay. The CTL activity of these CTL lines was measured by IFN-gamma ELISA (FIG. 14). These CTL lines showed potent IFN-gamma production against target cells pulsed with the respective peptides, in comparison with target cells that have not been pulsed with the peptides. Further, CTL clones were established from the CTL lines by limiting dilution as described in the "Materials and methods" section above, IFN-gamma production from the CTL clones against peptide-pulsed C1R-A01 cell was measured by IFN-gamma ELISA. Potent IFN-gamma production was observed in CTL clone stimulated with KOC1-A01-9-96 (SEQ ID NO: 86) (FIG. 15).

Figure 16:
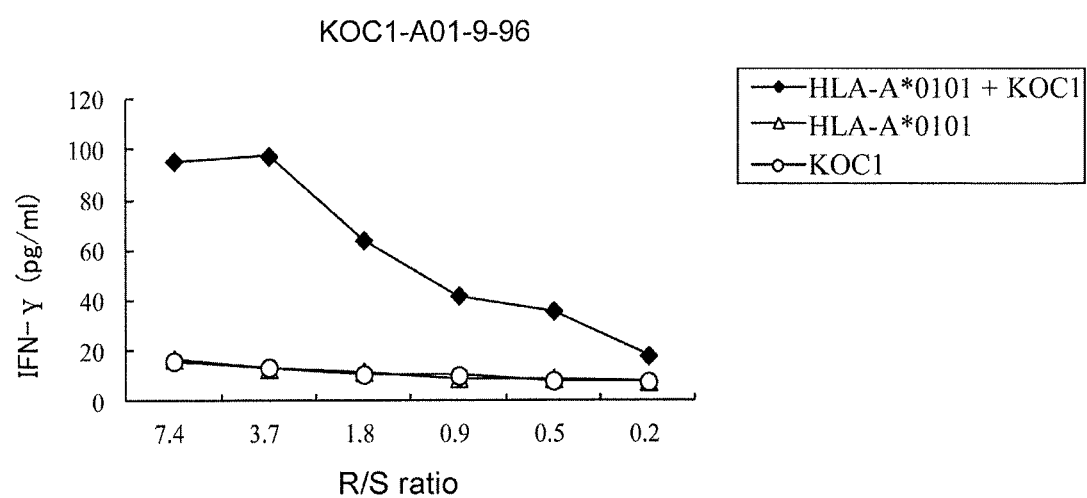
FIG. 16 is a line graph showing specific CTL activity against target cells expressing both KOC1 and HLA-A*0101. COS7 cells transfected with either HLA-A*0101 or the full-length KOC1 gene were prepared as the control. The CTL clone established using KOC1-A01-9-96 (SEQ ID NO: 86) demonstrated a specific CTL activity against COS7 cells transfected with both KOC1 and HLA-A*0101 (black diamond). On the other hand, a significant specific CTL activity was not shown against target cells transfected with either one of HLA-A*0101 (white triangle) and KOC1 (white circle).

Specific CTL Activity Against Target Cells Expressing KOC1 and HLA-A*0101 The CTL clone established against KOC1-A01-9-96 (SEQ ID NO: 86) was investigated for its ability to recognize target cells expressing KOC1 and the HLA-A*0101 molecule. COS7 cells transfected with both full-length KOC1 and the HLA-A*0101 gene (a specific model of target cells expressing KOC1 and the HLA-A*0101 gene) were prepared as the target cell. COS7 cells transfected with either full-length KOC1 or HLA-A*0101 were prepared as the control. The CTL clone stimulated with KOC1-A01-9-96 (SEQ ID NO: 86) demonstrated potent CTL activities against COS7 cells expressing both KOC1 and HLA-A*0101 (FIG. 16). On the other hand, a significant specific CTL activity was not detected against the control cells. These data clearly proved that KOC1-A01-9-96 (SEQ ID NO: 86) is a peptide generated from endogenous processing of KOC1, and is presented on target cells with the HLA-A*0101 molecule and recognized by CTLs. These results demonstrated the possibility that KOC1-A01-9-96 (SEQ ID NO: 86) may be suitable as a cancer vaccine for patients having a KOC1-expressing cancer.

Homology Analysis of Antigen Peptides

CTLs stimulated with KOC1-A01-9-96 (SEQ ID NO: 86), KOC1-A01-9-118 (SEQ ID NO: 87), KOC1-A01-9-404 (SEQ ID NO: 90), KOC1-A01-9-402 (SEQ ID NO: 92), KOC1-A01-10-312 (SEQ ID NO: 46), KOC1-A01-10-402 (SEQ ID NO: 95), or KOC1-A01-10-535 (SEQ ID NO: 41) demonstrated significant specific CTL activities. These results may be due to the fact that the KOC1-A01-9-96 (SEQ ID NO: 86), KOC1-A01-9-118 (SEQ ID NO: 87), KOC1-A01-9-404 (SEQ ID NO: 90), KOC1-A01-9-402 (SEQ ID NO: 92), KOC1-A01-10-312 (SEQ ID NO: 46), KOC1-A01-10-402 (SEQ ID NO: 95), and KOC1-A01-10-535 (SEQ ID NO: 41) sequences are homologous to peptides derived from other molecules known for sensitizing the human immune system. In order to exclude this possibility, homology analysis was performed by querying these peptide sequences using the BLAST algorithm (blast.ncbi.nlm.nih.gov/Blast.cgi). This result showed that there is no sequence having a significant homology with the KOC1-A01-9-96 (SEQ ID NO: 86), KOC1-A01-9-118 (SEQ ID NO: 87), KOC1-A01-9-404 (SEQ ID NO: 90), KOC1-A01-9-402 (SEQ ID NO: 92), KOC1-A01-10-312 (SEQ ID NO: 46), KOC1-A01-10-402 (SEQ ID NO: 95), and KOC1-A01-10-535 (SEQ ID NO: 41) sequences. On the other hand, KOC1-A01-9-118 (SEQ ID NO: 87) is identical to peptide sequences identified in IMP-1 and IMP-2 which are the other IMP families. It has been previously reported that IMP-1 is not expressed in normal organs except testis, fetal liver and placenta (Hammer N A et al., Reproduction. 2005; 130(2): 203-12). It is reported to be associated with tumor progression in lung cancer patients (Kato T et al., Clin Cancer Res. 2007; 13: 434-42). It has been previously reported that IMP-2 is not expressed in normal organs except testis and fetal liver (Hammer N A et al., Reproduction. 2005; 130(2): 203-12). It is involved in the proliferation of glioblastoma cancer stem cells (Janiszewska M et al., Genes Dev. 2012; 26(17): 1926-44). IMP-1 and IMP-2 are promising as target antigens for cancer immunotherapy. Therefore, to the knowledge of the present inventors, there is almost no possibility that these peptides would elicit an unintended immune response against other unrelated molecules. In conclusion, novel KOC1-derived HLA-A01-restricted epitope peptides were identified. It was demonstrated that the KOC1-derived epitope peptides are applicable for cancer immunotherapy.

Example 5

Preparation of Emulsion Formulations

A peptide was dissolved in an injection solvent or sterile physiological saline to become 1.0 mg/ml to 10.0 mg/ml, and collected into a syringe. This was connected via a connector to a syringe filled with an IFA in an amount equivalent to an injection solvent or sterile physiological saline, and mixed by alternately pushing the syringe plungers of the two connected syringes. After several minutes of mixing, completion of the emulsion was assessed by the drop test method. The drop test method can be performed by dropping one drop of the mixed sample on water. The emulsion is assessed as completed when the sample dropped on water does not immediately diffuse in water; and the emulsion is assessed as incompleted when the sample dropped on water diffuses right away in water. When the emulsion is assessed as incompleted, further mixing is carried out to complete the emulsion. The completed emulsion can be administered to a cancer patient by subcutaneous injection. The cancer patient subject to administration can be selected from patients affected by bladder cancer, cervical cancer, cholangiocellular cancer, chronic myeloid leukemia (CML), colon cancer, rectum cancer, esophagus cancer, diffuse gastric cancer, non-small-cell lung cancer, small-cell lung cancer, lymphoma, osteosarcoma, ovarian cancer, kidney cancer, head and neck cancer, soft tissue tumor, testis cancer or such.

Preparation of Freeze-Dried Formulations

A peptide was dissolved in an injection solvent to become 1.0 mg/ml to 10.0 mg/ml, and sterilized by filtration. This was filled into a sterilized vial, and half-capped with a sterilized rubber plug. After this vial was freeze-dried, it was completely capped and seamed with an aluminum cap to produce a freeze-dried formulation. When in use, an injection solvent or sterile physiological saline was injected into the vial to re-dissolve the freeze-dried powder. The re-dissolved solution in the vial was collected using a syringe, and the syringe was connected via a connector with a syringe filled with an IFA in an amount equivalent to the collected re-dissolved solution. The re-dissolved solution and IFA were mixed by alternately pushing the syringe plungers of the two connected syringes. After several minutes of mixing, completion of the emulsion was assessed by the drop test method. The completed emulsion can be administered to a cancer patient by subcutaneous injection. The cancer patient subject to administration can be selected from patients affected by bladder cancer, cervical cancer, cholangiocellular cancer, chronic myeloid leukemia (CML), colon cancer, rectum cancer, esophagus cancer, diffuse gastric cancer, non-small-cell lung cancer, small-cell lung cancer, lymphoma, osteosarcoma, ovarian cancer, kidney cancer, head and neck cancer, soft tissue tumor, testis cancer or such.

INDUSTRIAL APPLICABILITY

The present invention provides KOC1-derived novel HLA-A11-restricted, HLA-A33-restricted, HLA-A03-restricted and HLA-A01-restricted epitope peptides that induce a potent and specific anti-tumor immune response and thus have applicability for a wide range of cancer types. The peptides, compositions, APCs, and CTLs in the present invention can be used as a peptide vaccine for cancer expressing KOC1, for example, bladder cancer, cervical cancer, cholangiocellular cancer, chronic myeloid leukemia (CML), colon cancer, rectum cancer, esophagus cancer, diffuse gastric cancer, non-small-cell lung cancer, small-cell lung cancer, lymphoma, osteosarcoma, ovarian cancer, kidney cancer, head and neck cancer, soft tissue tumor, and testis cancer.

While the present invention is herein described in detail and with respect to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. A composition comprising a pharmaceutically acceptable carrier and a peptide consisting of the amino acid sequence selected from among SEQ ID NOS: 61, 62, 63, 64, 67, 74, 77, 79, 80, 85, 86, 87, 90, 92 and 95; in combination with an adjuvant in an amount effective to enhance an immune response.

2. An emulsion comprising one or more peptides consisting of the amino acid sequence selected from among SEQ ID NOS: 61, 62, 63, 64, 67, 74, 77, 79, 80, 85, 86, 87, 90, 92 and 95, a water-soluble carrier and an oil adjuvant.

3. A kit comprising a container that houses a composition comprising a pharmaceutically acceptable carrier and a peptide consisting of the amino acid sequence selected from among SEQ ID NOS: 61, 62, 63, 64, 67, 74, 77, 79, 80, 85, 86, 87, 90, 92 and 95; and a container that houses an adjuvant in an amount effective to enhance an immune response.

4. A method of inducing an APC(s) having CTL-inducing ability, the method comprising a step of
contacting an APC(s) with a peptide of in vitro, ex vivo or in vivo, wherein the peptide consists of the amino acid sequence selected from among SEQ ID NOS: 61, 62, 63, 64, 67, 74, 77, 79, 80, 85, 86, 87, 90, 92 and 95.

5. A method of inducing a CTL(s), the method which comprising a step of
co-culturing a CD8-positive T cell(s) with an APC(s) that presents on its surface a complex of an HLA antigen and a peptide consisting of the amino acid sequence selected from among SEQ ID NOS: 61, 62, 63, 64, 67, 74, 77, 79, 80, 85, 86, 87, 90, 92 and 95.

6. A method of inducing an immune response against cancer, the method comprising administering to a subject a peptide consisting of the amino acid sequence selected from among SEQ ID NOS: 61, 62, 63, 64, 67, 74, 77, 79, 80, 85, 86, 87, 90, 92 and 95.

7. A method of treating and/or preventing cancer, and/or preventing postoperative recurrence thereof, the method comprising administering to a subject a peptide consisting of the amino acid sequence selected from among SEQ ID NOS: 61, 62, 63, 64, 67, 74, 77, 79, 80, 85, 86, 87, 90, 92 and 95.

* * * * *

```
                          SEQUENCE LISTING

<160> NUMBER OF SEQ ID NOS: 111

<210> SEQ ID NO 1
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 1

Lys Ser Ile Leu Glu Ile Met His Lys
1               5

<210> SEQ ID NO 2
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 2

Val Val Asn Val Thr Tyr Ser Ser Lys
1               5

<210> SEQ ID NO 3
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 3

Lys Ala Gln Gly Arg Ile Tyr Gly Lys
1               5

<210> SEQ ID NO 4
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 4

Ser Ser Ala Glu Val Val Val Pro Arg
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 5

Leu Ser Val Gly Ala Ile Ile Gly Lys
1               5

<210> SEQ ID NO 6
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 6

Pro Val Ser Gly Pro Phe Leu Val Lys
1               5

<210> SEQ ID NO 7
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 7

Lys Ala Ile Glu Ala Leu Ser Gly Lys
1               5

<210> SEQ ID NO 8
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 8

Phe Gln Leu Glu Asn Phe Thr Leu Lys
1               5

<210> SEQ ID NO 9
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 9

Gly Ala Thr Ile Arg Asn Ile Thr Lys
1               5

<210> SEQ ID NO 10
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 10

Lys Ala Glu Glu Glu Ile Met Lys Lys
1               5
```

```
<210> SEQ ID NO 11
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 11

Phe Ala Ala Gly Arg Val Ile Gly Lys
1               5

<210> SEQ ID NO 12
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 12

Pro Ser Asp Leu Glu Ser Ile Phe Lys
1               5

<210> SEQ ID NO 13
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 13

Val Val Lys Ile Thr Gly His Phe Tyr
1               5

<210> SEQ ID NO 14
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 14

Phe Val Ser Pro Lys Glu Glu Val Lys
1               5

<210> SEQ ID NO 15
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 15

Arg Val Pro Ser Phe Ala Ala Gly Arg
1               5

<210> SEQ ID NO 16
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 16

Lys Phe Thr Glu Glu Ile Pro Leu Lys
1               5

<210> SEQ ID NO 17
```

```
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 17

Gln Ser Lys Ile Asp Val His Arg Lys
1               5

<210> SEQ ID NO 18
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 18

Lys Gly Asn Val Glu Thr Cys Ala Lys
1               5

<210> SEQ ID NO 19
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 19

Tyr Ala Cys Gln Val Ala Gln Arg Lys
1               5

<210> SEQ ID NO 20
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 20

Asn Ile Thr Lys Gln Thr Gln Ser Lys
1               5

<210> SEQ ID NO 21
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 21

Lys Ile Glu Gln Asp Thr Asp Thr Lys
1               5

<210> SEQ ID NO 22
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 22

Ile Gln Glu Ile Leu Thr Gln Val Lys
1               5

<210> SEQ ID NO 23
<211> LENGTH: 9
```

```
<212> TYPE: PRT
<213> ORGANISM: Artificial Sequence
<220> FEATURE:
<223> OTHER INFORMATION: a peptide derived from KOC1

<400> SEQUENCE: 23

Gln Gly Ser Pro Gly Ser Val Ser Lys
1               5

<210> SEQ ID NO 24
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 24

Gln Val Lys Gln His Gln Gln Gln Lys
1               5

<210> SEQ ID NO 25
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 25

Ser Gly Lys Ile Glu Leu His Gly Lys
1               5

<210> SEQ ID NO 26
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 26

Gln Phe Val Gly Ala Ile Ile Gly Lys
1               5

<210> SEQ ID NO 27
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 27

Ala Val Val Asn Val Thr Tyr Ser Ser Lys
1               5                   10

<210> SEQ ID NO 28
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 28

Ala Leu Ser Val Gly Ala Ile Ile Gly Lys
1               5                   10

<210> SEQ ID NO 29
<211> LENGTH: 10
<212> TYPE: PRT
```

```
<213> ORGANISM: Artificial Sequence
<220> FEATURE:
<223> OTHER INFORMATION: a peptide derived from KOC1

<400> SEQUENCE: 29

Ile Thr Gly Pro Pro Glu Ala Gln Phe Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 30

Thr Gln Phe Val Gly Ala Ile Ile Gly Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 31

Ser Val Pro Lys Arg Gln Arg Ile Arg Lys
1               5                   10

<210> SEQ ID NO 32
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 32

Ala Pro Ser Asp Leu Glu Ser Ile Phe Lys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 33

Gly Ser Pro Gly Ser Val Ser Lys Gln Lys
1               5                   10

<210> SEQ ID NO 34
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 34

Ser Phe Ala Ala Gly Arg Val Ile Gly Lys
1               5                   10

<210> SEQ ID NO 35
<211> LENGTH: 10
<212> TYPE: PRT
<213> ORGANISM: Artificial Sequence
```

```
<220> FEATURE:
<223> OTHER INFORMATION: a peptide derived from KOC1

<400> SEQUENCE: 35

Leu Ser Ser Ala Glu Val Val Pro Arg
1               5                   10

<210> SEQ ID NO 36
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 36

Lys Ile Gln Glu Ile Leu Thr Gln Val Lys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 37

Leu Ser Arg Phe Ala Gly Ala Ser Ile Lys
1               5                   10

<210> SEQ ID NO 38
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 38

Arg Gln Gly Ser Pro Gly Ser Val Ser Lys
1               5                   10

<210> SEQ ID NO 39
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 39

Val Thr Tyr Ser Ser Lys Asp Gln Ala Arg
1               5                   10

<210> SEQ ID NO 40
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 40

Thr Gln Ser Lys Ile Asp Val His Arg Lys
1               5                   10

<210> SEQ ID NO 41
<211> LENGTH: 10
<212> TYPE: PRT
<213> ORGANISM: Artificial Sequence
<220> FEATURE:
```

-continued

```
<223> OTHER INFORMATION: a peptide derived from KOC1

<400> SEQUENCE: 41

Val Val Val Lys Ile Thr Gly His Phe Tyr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 42

Gln Thr Gln Ser Lys Ile Asp Val His Arg
1               5                   10

<210> SEQ ID NO 43
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 43

Leu Ser Gly Lys Ile Glu Leu His Gly Lys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 44

Gly Phe Gln Leu Glu Asn Phe Thr Leu Lys
1               5                   10

<210> SEQ ID NO 45
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 45

Ala Leu Gln Ser Gly Pro Pro Gln Ser Arg
1               5                   10

<210> SEQ ID NO 46
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 46

Ile Ser Pro Leu Gln Glu Leu Thr Leu Tyr
1               5                   10

<210> SEQ ID NO 47
<211> LENGTH: 10
<212> TYPE: PRT
<213> ORGANISM: Artificial Sequence
<220> FEATURE:
<223> OTHER INFORMATION: a peptide derived from KOC1
```

```
<400> SEQUENCE: 47

Ile Ala Pro Ala Glu Ala Pro Asp Ala Lys
1               5                   10

<210> SEQ ID NO 48
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 48

Ile Pro Val Ser Gly Pro Phe Leu Val Lys
1               5                   10

<210> SEQ ID NO 49
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 49

Gln Ser Gly Pro Pro Gln Ser Arg Arg Lys
1               5                   10

<210> SEQ ID NO 50
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 50

Glu Val Leu Asp Ser Leu Leu Val Gln Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 51

Cys Ala Lys Ala Glu Glu Glu Ile Met Lys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 52

Ile Leu Ala His Asn Asn Phe Val Gly Arg
1               5                   10

<210> SEQ ID NO 53
<211> LENGTH: 10
<212> TYPE: PRT
<213> ORGANISM: Artificial Sequence
<220> FEATURE:
<223> OTHER INFORMATION: a peptide derived from KOC1
```

```
<400> SEQUENCE: 53

Ala Gln Gly Arg Ile Tyr Gly Lys Ile Lys
1               5                   10

<210> SEQ ID NO 54
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 54

Ala Gln Gln Asn Pro Leu Gln Gln Pro Arg
1               5                   10

<210> SEQ ID NO 55
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 55

Ile Ile Gly Lys Gln Gly Gln His Ile Lys
1               5                   10

<210> SEQ ID NO 56
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 56

Thr Gln Val Lys Gln His Gln Gln Gln Lys
1               5                   10

<210> SEQ ID NO 57
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 57

Cys Lys Ser Ile Leu Glu Ile Met His Lys
1               5                   10

<210> SEQ ID NO 58
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 58

Leu Ile Gly Lys Glu Gly Arg Asn Leu Lys
1               5                   10

<210> SEQ ID NO 59
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 59
```

```
Ile Met His Lys Glu Ala Gln Asp Ile Lys
1               5                   10

<210> SEQ ID NO 60
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 60

Leu Gln Ser Gly Pro Pro Gln Ser Arg Arg
1               5                   10

<210> SEQ ID NO 61
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 61

Phe Tyr Ala Cys Gln Val Ala Gln Arg
1               5

<210> SEQ ID NO 62
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 62

Leu Ala His Asn Asn Phe Val Gly Arg
1               5

<210> SEQ ID NO 63
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 63

Glu Leu Thr Leu Tyr Asn Pro Glu Arg
1               5

<210> SEQ ID NO 64
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 64

Glu Val Lys Leu Glu Ala His Ile Arg
1               5

<210> SEQ ID NO 65
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 65
```

Thr Tyr Ser Ser Lys Asp Gln Ala Arg
1               5

<210> SEQ ID NO 66
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 66

Glu Ala Gln Phe Lys Ala Gln Gly Arg
1               5

<210> SEQ ID NO 67
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 67

Asn Phe Val Gly Arg Leu Ile Gly Lys
1               5

<210> SEQ ID NO 68
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 68

Thr Gln Ser Lys Ile Asp Val His Arg
1               5

<210> SEQ ID NO 69
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 69

Glu Val Glu His Ser Val Pro Lys Arg
1               5

<210> SEQ ID NO 70
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 70

Gln Gln Asn Pro Leu Gln Gln Pro Arg
1               5

<210> SEQ ID NO 71
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 71

Glu Thr Val His Leu Phe Ile Pro Ala

```
1               5
```

<210> SEQ ID NO 72
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 72

```
Ser Val Pro Lys Arg Gln Arg Ile Arg
1               5
```

<210> SEQ ID NO 73
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 73

```
Gln Ser Gly Pro Pro Gln Ser Arg Arg
1               5
```

<210> SEQ ID NO 74
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 74

```
Leu Val Lys Thr Gly Tyr Ala Phe Val
1               5
```

<210> SEQ ID NO 75
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 75

```
Ile Gly Lys Glu Gly Ala Thr Ile Arg
1               5
```

<210> SEQ ID NO 76
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 76

```
Asp Thr Lys Ile Thr Ile Ser Pro Leu
1               5
```

<210> SEQ ID NO 77
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 77

```
His Phe Tyr Ala Cys Gln Val Ala Gln Arg
1               5                   10
```

```
<210> SEQ ID NO 78
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 78

His Ser Val Pro Lys Arg Gln Arg Ile Arg
1               5                   10

<210> SEQ ID NO 79
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 79

Phe Tyr Ala Cys Gln Val Ala Gln Arg Lys
1               5                   10

<210> SEQ ID NO 80
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 80

Gln Gly Gln His Ile Lys Gln Leu Ser Arg
1               5                   10

<210> SEQ ID NO 81
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 81

Lys Gln Lys Pro Cys Asp Leu Pro Leu Arg
1               5                   10

<210> SEQ ID NO 82
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 82

Ile Ile Gly Lys Glu Gly Ala Thr Ile Arg
1               5                   10

<210> SEQ ID NO 83
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 83

Asn Phe Val Ser Pro Lys Glu Glu Val Lys
1               5                   10
```

<210> SEQ ID NO 84
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 84

Arg Gln Arg Ile Arg Lys Leu Gln Ile Arg
1               5                   10

<210> SEQ ID NO 85
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 85

Asn Asn Phe Val Gly Arg Leu Ile Gly Lys
1               5                   10

<210> SEQ ID NO 86
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 86

Val Leu Asp Ser Leu Leu Val Gln Tyr
1               5

<210> SEQ ID NO 87
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 87

Glu Thr Ala Val Val Asn Val Thr Tyr
1               5

<210> SEQ ID NO 88
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 88

Asn Thr Asp Ser Glu Thr Ala Val Val
1               5

<210> SEQ ID NO 89
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 89

Phe Thr Glu Glu Ile Pro Leu Lys Ile
1               5

```
<210> SEQ ID NO 90
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 90

Glu Thr Glu Thr Val His Leu Phe Ile
1               5

<210> SEQ ID NO 91
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 91

Gln Leu Glu Asn Phe Thr Leu Lys Val
1               5

<210> SEQ ID NO 92
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 92

Gln Ser Glu Thr Glu Thr Val His Leu
1               5

<210> SEQ ID NO 93
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 93

Asp Thr Asp Thr Lys Ile Thr Ile Ser
1               5

<210> SEQ ID NO 94
<211> LENGTH: 9
<212> TYPE: PRT
<213> ORGANISM: Artificial Sequence
<220> FEATURE:
<223> OTHER INFORMATION: a peptide derived from KOC1

<400> SEQUENCE: 94

Ser Pro Leu Gln Glu Leu Thr Leu Tyr
1               5

<210> SEQ ID NO 95
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 95

Gln Ser Glu Thr Glu Thr Val His Leu Phe
1               5                   10

<210> SEQ ID NO 96
```

```
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 96

Leu Ser Glu Asn Ala Ala Pro Ser Asp Leu
1               5                   10

<210> SEQ ID NO 97
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 97

Phe Thr Glu Glu Ile Pro Leu Lys Ile Leu
1               5                   10

<210> SEQ ID NO 98
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 98

Ala Gln Phe Lys Ala Gln Gly Arg Ile Tyr
1               5                   10

<210> SEQ ID NO 99
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 99

Glu Ile Met Lys Lys Ile Arg Glu Ser Tyr
1               5                   10

<210> SEQ ID NO 100
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 100

Gly Thr Ser Ala Ala Cys Lys Ser Ile Leu
1               5                   10

<210> SEQ ID NO 101
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 101

Ser Gly Pro Phe Leu Val Lys Thr Gly Tyr
1               5                   10

<210> SEQ ID NO 102
<211> LENGTH: 10
```

```
<212> TYPE: PRT
<213> ORGANISM: Artificial Sequence
<220> FEATURE:
<223> OTHER INFORMATION: a peptide derived from KOC1

<400> SEQUENCE: 102

Asn Thr Asp Ser Glu Thr Ala Val Val Asn
1               5                   10

<210> SEQ ID NO 103
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 103

Asp Thr Asp Thr Lys Ile Thr Ile Ser Pro
1               5                   10

<210> SEQ ID NO 104
<211> LENGTH: 10
<212> TYPE: PRT
<213> ORGANISM: Artificial Sequence
<220> FEATURE:
<223> OTHER INFORMATION: a peptide derived from KOC1

<400> SEQUENCE: 104

Asp Leu Glu Ser Ile Phe Lys Asp Ala Lys
1               5                   10

<210> SEQ ID NO 105
<211> LENGTH: 22
<212> TYPE: DNA
<213> ORGANISM: Artificial Sequence
<220> FEATURE:
<223> OTHER INFORMATION: a PCR primer for the TCR analysis

<400> SEQUENCE: 105
gtctaccagg cattcgcttc at                                              22

<210> SEQ ID NO 106
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 106
tcagctggac cacagccgca gcgt                                            24

<210> SEQ ID NO 107
<211> LENGTH: 21
<212> TYPE: DNA
<213> ORGANISM: Artificial Sequence
<220> FEATURE:
<223> OTHER INFORMATION: a PCR primer for the TCR analysis

<400> SEQUENCE: 107
tcagaaatcc tttctcttga c                                               21

<210> SEQ ID NO 108
<211> LENGTH: 24
<212> TYPE: DNA
<213> ORGANISM: Artificial Sequence
<220> FEATURE:
<223> OTHER INFORMATION: a PCR primer for the TCR analysis
```

<400> SEQUENCE: 108

```
ctagcctctg gaatcctttc tctt                                                24
```

<210> SEQ ID NO 109
<211> LENGTH: 4168
<212> TYPE: DNA
<213> ORGANISM: Homo sapiens
<220> FEATURE:
<221> NAME/KEY: CDS
<222> LOCATION: (267)..(2006)

<400> SEQUENCE: 109

```
aagacttagg aagactggtg gatgcgtttg ggttgtagct aggcttttc ttttctttct         60 cttttaaaac acatctagac aaggaaaaaa caagcctcgg atctgatttt tcactcctcg       120
ttcttgtgct tggttcttac tgtgtttgtg tattttaaag gcgagaagac gaggggaaca       180
aaaccagctg gatccatcca tcaccgtggg tggttttaat tttcgtttt ttctcgttat        240 ttttttttaa acaaccactc ttcaca atg aac aaa ctg tat atc gga aac ctc       293
                              Met Asn Lys Leu Tyr Ile Gly Asn Leu
                                1               5 agc gag aac gcc gcc ccc tcg gac cta gaa agt atc ttc aag gac gcc        341
Ser Glu Asn Ala Ala Pro Ser Asp Leu Glu Ser Ile Phe Lys Asp Ala
 10                  15                  20                  25 aag atc ccg gtg tcg gga ccc ttc ctg gtg aag act ggc tac gcg ttc        389
Lys Ile Pro Val Ser Gly Pro Phe Leu Val Lys Thr Gly Tyr Ala Phe
                 30                  35                  40 gtg gac tgc ccg gac gag agc tgg gcc ctc aag gcc atc gag gcg ctt        437
Val Asp Cys Pro Asp Glu Ser Trp Ala Leu Lys Ala Ile Glu Ala Leu
             45                  50                  55 tca ggt aaa ata gaa ctg cac ggg aaa ccc ata gaa gtt gag cac tcg        485
Ser Gly Lys Ile Glu Leu His Gly Lys Pro Ile Glu Val Glu His Ser
         60                  65                  70 gtc cca aaa agg caa agg att cgg aaa ctt cag ata cga aat atc ccg        533
Val Pro Lys Arg Gln Arg Ile Arg Lys Leu Gln Ile Arg Asn Ile Pro
     75                  80                  85 cct cat tta cag tgg gag gtg ctg gat agt tta cta gtc cag tat gga        581
Pro His Leu Gln Trp Glu Val Leu Asp Ser Leu Leu Val Gln Tyr Gly
 90                  95                 100                 105 gtg gtg gag agc tgt gag caa gtg aac act gac tcg gaa act gca gtt        629
Val Val Glu Ser Cys Glu Gln Val Asn Thr Asp Ser Glu Thr Ala Val
                110                 115                 120 gta aat gta acc tat tcc agt aag gac caa gct aga caa gca cta gac        677
Val Asn Val Thr Tyr Ser Ser Lys Asp Gln Ala Arg Gln Ala Leu Asp
            125                 130                 135 aaa ctg aat gga ttt cag tta gag aat ttc acc ttg aaa gta gcc tat        725
Lys Leu Asn Gly Phe Gln Leu Glu Asn Phe Thr Leu Lys Val Ala Tyr
        140                 145                 150 atc cct gat gaa atg gcc gcc cag caa aac ccc ttg cag cag ccc cga        773
Ile Pro Asp Glu Met Ala Ala Gln Gln Asn Pro Leu Gln Gln Pro Arg
    155                 160                 165 ggt cgc cgg ggg ctt ggg cag agg ggc tcc tca agg cag ggg tct cca        821
Gly Arg Arg Gly Leu Gly Gln Arg Gly Ser Ser Arg Gln Gly Ser Pro
170                 175                 180                 185 gga tcc gta tcc aag cag aaa cca tgt gat ttg cct ctg cgc ctg ctg        869
Gly Ser Val Ser Lys Gln Lys Pro Cys Asp Leu Pro Leu Arg Leu Leu
                190                 195                 200 gtt ccc acc caa ttt gtt gga gcc atc ata gga aaa gaa ggt gcc acc        917
Val Pro Thr Gln Phe Val Gly Ala Ile Ile Gly Lys Glu Gly Ala Thr
            205                 210                 215
```

| | | | | | | | | | | | | | | | |
|---|---|---|---|---|---|---|---|---|---|---|---|---|---|---|---|
| att | cgg | aac | atc | acc | aaa | cag | acc | cag | tct | aaa | atc | gat | gtc | cac | cgt | 965 |
| Ile | Arg | Asn | Ile | Thr | Lys | Gln | Thr | Gln | Ser | Lys | Ile | Asp | Val | His | Arg | |
| | 220 | | | | | 225 | | | | | 230 | | | | | |

| | | | | | | | | | | | | | | | | |
|---|---|---|---|---|---|---|---|---|---|---|---|---|---|---|---|---|
| aaa | gaa | aat | gcg | ggg | gct | gct | gag | aag | tcg | att | act | atc | ctc | tct | act | 1013 |
| Lys | Glu | Asn | Ala | Gly | Ala | Ala | Glu | Lys | Ser | Ile | Thr | Ile | Leu | Ser | Thr | |
| | 235 | | | | 240 | | | | | 245 | | | | | | |

| | | | | | | | | | | | | | | | | |
|---|---|---|---|---|---|---|---|---|---|---|---|---|---|---|---|---|
| cct | gaa | ggc | acc | tct | gcg | gct | tgt | aag | tct | att | ctg | gag | att | atg | cat | 1061 |
| Pro | Glu | Gly | Thr | Ser | Ala | Ala | Cys | Lys | Ser | Ile | Leu | Glu | Ile | Met | His | |
| 250 | | | | | 255 | | | | 260 | | | | | 265 | | |

| | | | | | | | | | | | | | | | | |
|---|---|---|---|---|---|---|---|---|---|---|---|---|---|---|---|---|
| aag | gaa | gct | caa | gat | ata | aaa | ttc | aca | gaa | gag | atc | ccc | ttg | aag | att | 1109 |
| Lys | Glu | Ala | Gln | Asp | Ile | Lys | Phe | Thr | Glu | Glu | Ile | Pro | Leu | Lys | Ile | |
| | | | 270 | | | | | 275 | | | | | 280 | | | |

| | | | | | | | | | | | | | | | | |
|---|---|---|---|---|---|---|---|---|---|---|---|---|---|---|---|---|
| tta | gct | cat | aat | aac | ttt | gtt | gga | cgt | ctt | att | ggt | aaa | gaa | gga | aga | 1157 |
| Leu | Ala | His | Asn | Asn | Phe | Val | Gly | Arg | Leu | Ile | Gly | Lys | Glu | Gly | Arg | |
| | | 285 | | | | | 290 | | | | | 295 | | | | |

| | | | | | | | | | | | | | | | | |
|---|---|---|---|---|---|---|---|---|---|---|---|---|---|---|---|---|
| aat | ctt | aaa | aaa | att | gag | caa | gac | aca | gac | act | aaa | atc | acg | ata | tct | 1205 |
| Asn | Leu | Lys | Lys | Ile | Glu | Gln | Asp | Thr | Asp | Thr | Lys | Ile | Thr | Ile | Ser | |
| | | 300 | | | | | 305 | | | | | 310 | | | | |

| | | | | | | | | | | | | | | | | |
|---|---|---|---|---|---|---|---|---|---|---|---|---|---|---|---|---|
| cca | ttg | cag | gaa | ttg | acg | ctg | tat | aat | cca | gaa | cgc | act | att | aca | gtt | 1253 |
| Pro | Leu | Gln | Glu | Leu | Thr | Leu | Tyr | Asn | Pro | Glu | Arg | Thr | Ile | Thr | Val | |
| | 315 | | | | | 320 | | | | | 325 | | | | | |

| | | | | | | | | | | | | | | | | |
|---|---|---|---|---|---|---|---|---|---|---|---|---|---|---|---|---|
| aaa | ggc | aat | gtt | gag | aca | tgt | gcc | aaa | gct | gag | gag | gag | atc | atg | aag | 1301 |
| Lys | Gly | Asn | Val | Glu | Thr | Cys | Ala | Lys | Ala | Glu | Glu | Glu | Ile | Met | Lys | |
| 330 | | | | | 335 | | | | | 340 | | | | | 345 | |

| | | | | | | | | | | | | | | | | |
|---|---|---|---|---|---|---|---|---|---|---|---|---|---|---|---|---|
| aaa | atc | agg | gag | tct | tat | gaa | aat | gat | att | gct | tct | atg | aat | ctt | caa | 1349 |
| Lys | Ile | Arg | Glu | Ser | Tyr | Glu | Asn | Asp | Ile | Ala | Ser | Met | Asn | Leu | Gln | |
| | | | | 350 | | | | | 355 | | | | | 360 | | |

| | | | | | | | | | | | | | | | | |
|---|---|---|---|---|---|---|---|---|---|---|---|---|---|---|---|---|
| gca | cat | tta | att | cct | gga | tta | aat | ctg | aac | gcc | ttg | ggt | ctg | ttc | cca | 1397 |
| Ala | His | Leu | Ile | Pro | Gly | Leu | Asn | Leu | Asn | Ala | Leu | Gly | Leu | Phe | Pro | |
| | | | 365 | | | | | 370 | | | | | 375 | | | |

| | | | | | | | | | | | | | | | | |
|---|---|---|---|---|---|---|---|---|---|---|---|---|---|---|---|---|
| ccc | act | tca | ggg | atg | cca | cct | ccc | acc | tca | ggg | ccc | cct | tca | gcc | atg | 1445 |
| Pro | Thr | Ser | Gly | Met | Pro | Pro | Pro | Thr | Ser | Gly | Pro | Pro | Ser | Ala | Met | |
| | | 380 | | | | | 385 | | | | | 390 | | | | |

| | | | | | | | | | | | | | | | | |
|---|---|---|---|---|---|---|---|---|---|---|---|---|---|---|---|---|
| act | cct | ccc | tac | ccg | cag | ttt | gag | caa | tca | gaa | acg | gag | act | gtt | cat | 1493 |
| Thr | Pro | Pro | Tyr | Pro | Gln | Phe | Glu | Gln | Ser | Glu | Thr | Glu | Thr | Val | His | |
| | 395 | | | | | 400 | | | | | 405 | | | | | |

| | | | | | | | | | | | | | | | | |
|---|---|---|---|---|---|---|---|---|---|---|---|---|---|---|---|---|
| ctg | ttt | atc | cca | gct | cta | tca | gtc | ggt | gcc | atc | atc | ggc | aag | cag | ggc | 1541 |
| Leu | Phe | Ile | Pro | Ala | Leu | Ser | Val | Gly | Ala | Ile | Ile | Gly | Lys | Gln | Gly | |
| 410 | | | | | 415 | | | | | 420 | | | | | 425 | |

| | | | | | | | | | | | | | | | | |
|---|---|---|---|---|---|---|---|---|---|---|---|---|---|---|---|---|
| cag | cac | atc | aag | cag | ctt | tct | cgc | ttt | gct | gga | gct | tca | att | aag | att | 1589 |
| Gln | His | Ile | Lys | Gln | Leu | Ser | Arg | Phe | Ala | Gly | Ala | Ser | Ile | Lys | Ile | |
| | | | | 430 | | | | | 435 | | | | | 440 | | |

| | | | | | | | | | | | | | | | | |
|---|---|---|---|---|---|---|---|---|---|---|---|---|---|---|---|---|
| gct | cca | gcg | gaa | gca | cca | gat | gct | aaa | gtg | agg | atg | gtg | att | atc | act | 1637 |
| Ala | Pro | Ala | Glu | Ala | Pro | Asp | Ala | Lys | Val | Arg | Met | Val | Ile | Ile | Thr | |
| | | | 445 | | | | | 450 | | | | | 455 | | | |

| | | | | | | | | | | | | | | | | |
|---|---|---|---|---|---|---|---|---|---|---|---|---|---|---|---|---|
| gga | cca | cca | gag | gct | cag | ttc | aag | gct | cag | gga | aga | att | tat | gga | aaa | 1685 |
| Gly | Pro | Pro | Glu | Ala | Gln | Phe | Lys | Ala | Gln | Gly | Arg | Ile | Tyr | Gly | Lys | |
| | | 460 | | | | | 465 | | | | | 470 | | | | |

| | | | | | | | | | | | | | | | | |
|---|---|---|---|---|---|---|---|---|---|---|---|---|---|---|---|---|
| att | aaa | gaa | gaa | aac | ttt | gtt | agt | cct | aaa | gaa | gag | gtg | aaa | ctt | gaa | 1733 |
| Ile | Lys | Glu | Glu | Asn | Phe | Val | Ser | Pro | Lys | Glu | Glu | Val | Lys | Leu | Glu | |
| | 475 | | | | | 480 | | | | | 485 | | | | | |

| | | | | | | | | | | | | | | | | |
|---|---|---|---|---|---|---|---|---|---|---|---|---|---|---|---|---|
| gct | cat | atc | aga | gtg | cca | tcc | ttt | gct | gct | ggc | aga | gtt | att | gga | aaa | 1781 |
| Ala | His | Ile | Arg | Val | Pro | Ser | Phe | Ala | Ala | Gly | Arg | Val | Ile | Gly | Lys | |
| 490 | | | | | 495 | | | | | 500 | | | | | 505 | |

| | | | | | | | | | | | | | | | | |
|---|---|---|---|---|---|---|---|---|---|---|---|---|---|---|---|---|
| gga | ggc | aaa | acg | gtg | aat | gaa | ctt | cag | aat | ttg | tca | agt | gca | gaa | gtt | 1829 |
| Gly | Gly | Lys | Thr | Val | Asn | Glu | Leu | Gln | Asn | Leu | Ser | Ser | Ala | Glu | Val | |
| | | | 510 | | | | | 515 | | | | | 520 | | | |

| | | | | | | | | | | | | | | | | |
|---|---|---|---|---|---|---|---|---|---|---|---|---|---|---|---|---|
| gtt | gtc | cct | cgt | gac | cag | aca | cct | gat | gag | aat | gac | caa | gtg | gtt | gtc | 1877 |
| Val | Val | Pro | Arg | Asp | Gln | Thr | Pro | Asp | Glu | Asn | Asp | Gln | Val | Val | Val | |

-continued

|  |  |  |  |  |  |  |  |  |  |  |  |  |  |  |  |
|---|---|---|---|---|---|---|---|---|---|---|---|---|---|---|---|
| | | 525 | | | | 530 | | | | | 535 | | | | |

```
aaa ata act ggt cac ttc tat gct tgc cag gtt gcc cag aga aaa att    1925
Lys Ile Thr Gly His Phe Tyr Ala Cys Gln Val Ala Gln Arg Lys Ile
        540                 545                 550 cag gaa att ctg act cag gta aag cag cac caa caa cag aag gct ctg    1973
Gln Glu Ile Leu Thr Gln Val Lys Gln His Gln Gln Lys Ala Leu
            555                 560                 565 caa agt gga cca cct cag tca aga cgg aag taa aggctcagga aacagcccac  2026
Gln Ser Gly Pro Pro Gln Ser Arg Arg Lys
570                 575 cacagaggca gatgccaaac caaagacaga ttgcttaacc aacagatggg cgctgacccc   2086
ctatccagaa tcacatgcac aagtttttac ctagccagtt gtttctgagg accaggcaac   2146
ttttgaactc ctgtctctgt gagaatgtat actttatgct ctctgaaatg tatgacaccc   2206
agctttaaaa caaacaaaca aacaaacaaa aaaagggtgg gggagggagg gaaagagaag   2266
agctctgcac ttcccttgt tgtagtctca cagtataaca gatattctaa ttcttcttaa    2326
tattcccca taatgccaga aattggctta atgatgcttt cactaaattc atcaaataga    2386
ttgctcctaa atccaattgt taaaattgga tcagaataat tatcacagga acttaaatgt   2446
taagccatta gcatagaaaa actgttctca gttttatttt tacctaacac taacatgagt   2506
aacctaaggg aagtgctgaa tggtgttggc aggggtatta aacgtgcatt tttactcaac   2566
tacctcaggt attcagtaat acaatgaaaa gcaaaattgt tccttttttt tgaaaatttt   2626
atatacttta taatgataga agtccaaccg ttttttaaaa aataaattta aaatttaaca   2686
gcaatcagct aacaggcaaa ttaagatttt tacttctggc tggtgacagt aaagctggaa   2746
aattaatttc agggttttt gaggcttttg acacagttat tagttaaatc aaatgttcaa    2806
aaaatacggag cagtgcctag tatctggaga gcagcactac catttattct ttcatttata  2866
gttgggaaag tttttgacgg tactaacaaa gtggtcgcag gagattttgg aacggctggt   2926
ttaaatggct tcaggagact tcagttttt gtttagctac atgattgaat gcataataaa    2986
tgctttgtgc ttctgactat caatacctaa agaaagtgca tcagtgaaga gatgcaagac   3046
tttcaactga ctggcaaaaa gcaagcttta gcttgtctta taggatgctt agtttgccac   3106
tacacttcag accaatggga cagtcataga tggtgtgaca gtgtttaaac gcaacaaaag   3166
gctacatttc catggggcca gcactgtcat gagcctcact aagctatttt gaagattttt   3226
aagcactgat aaattaaaaa aaaaaaatta gactccacct taagtagtaa agtataacag   3286
gatttctgta tactgtgcaa tcagttcttt gaaaaaaaag tcaaaagata gagaatacaa   3346
gaaaagtttt tgggatataa tttgaatgac tgtgaaaaca tatgaccttt gataacgaac   3406
tcatttgctc actccttgac agcaaagccc agtacgtaca attgtgttgg gtgtgggtgg   3466
tctccaaggc cacgctgctc tctgaattga tttttgagt tttgtttgta agatgatcac    3526
agtcatgtta cactgatcta aaggacatat atataaccct ttaaaaaaaa aatcactgcc   3586
tcattcttat ttcaagatga atttctatac agactagatg tttttctgaa gatcaattag   3646
acatttgaa aatgatttaa agtgttttcc ttaatgttct ctgaaaacaa gtttcttttg    3706
tagtttaaac caaaaaagtg ccctttttgt cactggattc tcctagcatt catgattttt   3766
ttttcataca atgaattaaa attgctaaaa tcatggactg gctttctggt tggatttcag   3826
gtaagatgtg tttaaggcca gagctttttct cagtatttga ttttttttccc caatatttga  3886
ttttttaaaa atatacacat aggtgctgca tttatatctg ctggtttaaa ttctgtcata   3946
tttcacttct agccttttag tatggcaaat catatttac ttttacttaa gcatttgtaa    4006
```
tttggagtat ctggtactag ctaagaaata attctataat tgagttttgt actcaccata        4066
tatggatcat tcctcatgta taatgtgccc caaatgcagc ttcattttcc agataccttg        4126
acgcagaata aattttttca tcatttaggt gcaaaaaaaa aa        4168

<210> SEQ ID NO 110
<211> LENGTH: 579
<212> TYPE: PRT
<213> ORGANISM: Homo sapiens

<400> SEQUENCE: 110

Met Asn Lys Leu Tyr Ile Gly Asn Leu Ser Glu Asn Ala Ala Pro Ser
1               5                   10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Met Ala Ala
145                 150                 155                 160

Gln Gln Asn Pro Leu Gln Pro Arg Gly Arg Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
        195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
            260                 265                 270

Phe Thr Glu Glu Ile Pro Leu Lys Ile Leu Ala His Asn Asn Phe Val
        275                 280                 285

Gly Arg Leu Ile Gly Lys Glu Gly Arg Asn Leu Lys Lys Ile Glu Gln
    290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Glu Ile Met Lys Lys Ile Arg Glu Ser Tyr Glu

```
                   340                 345                 350
Asn Asp Ile Ala Ser Met Asn Leu Gln Ala His Leu Ile Pro Gly Leu
            355                 360                 365

Asn Leu Asn Ala Leu Gly Leu Phe Pro Pro Thr Ser Gly Met Pro Pro
            370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Leu Phe Ile Pro Ala Leu Ser
            405                 410                 415

Val Gly Ala Ile Ile Gly Lys Gln Gly Gln His Ile Lys Gln Leu Ser
            420                 425                 430

Arg Phe Ala Gly Ala Ser Ile Lys Ile Ala Pro Ala Glu Ala Pro Asp
            435                 440                 445

Ala Lys Val Arg Met Val Ile Ile Thr Gly Pro Pro Glu Ala Gln Phe
            450                 455                 460

Lys Ala Gln Gly Arg Ile Tyr Gly Lys Ile Lys Glu Glu Asn Phe Val
465                 470                 475                 480

Ser Pro Lys Glu Glu Val Lys Leu Glu Ala His Ile Arg Val Pro Ser
            485                 490                 495

Phe Ala Ala Gly Arg Val Ile Gly Lys Gly Gly Lys Thr Val Asn Glu
            500                 505                 510

Leu Gln Asn Leu Ser Ser Ala Glu Val Val Pro Arg Asp Gln Thr
            515                 520                 525

Pro Asp Glu Asn Asp Gln Val Val Val Lys Ile Thr Gly His Phe Tyr
            530                 535                 540

Ala Cys Gln Val Ala Gln Arg Lys Ile Gln Glu Ile Leu Thr Gln Val
545                 550                 555                 560

Lys Gln His Gln Gln Gln Lys Ala Leu Gln Ser Gly Pro Pro Gln Ser
            565                 570                 575

Arg Arg Lys

<210> SEQ ID NO 111
<211> LENGTH: 4
<212> TYPE: PRT
<213> ORGANISM: Artificial Sequence
<220> FEATURE:
<223> OTHER INFORMATION: a linker peptide

<400> SEQUENCE: 111

Asn Lys Arg Lys
1
```

UNITED STATES PATENT AND TRADEMARK OFFICE
CERTIFICATE OF CORRECTION

PATENT NO. : 11,547,723 B2
APPLICATION NO. : 16/773487
DATED : January 10, 2023
INVENTOR(S) : Takuya Tsunoda et al.

It is certified that error appears in the above-identified patent and that said Letters Patent is hereby corrected as shown below:

In the Claims

In Claim 5, Column 126, Line 1, delete "which".

Signed and Sealed this
Twenty-seventh Day of June, 2023

Katherine Kelly Vidal
*Director of the United States Patent and Trademark Office*